(12) United States Patent
Wulff et al.

(10) Patent No.: US 8,067,460 B2
(45) Date of Patent: *Nov. 29, 2011

(54) 5-PHENOXYALKOXYPSORALENS AND METHODS FOR SELECTIVE INHIBITION OF THE VOLTAGE GATED KV1.3 POTASSIUM CHANNEL

(75) Inventors: Heike Wulff, Davis, CA (US); Ananthakrishnan Sankaranarayanan, Davis, CA (US); Wolfram Haensel, Kronshagen (DE); Alexander Schmitz, Kiel (DE); Kristina Schmidt-Lassen, Kiel (DE)

(73) Assignee: The Regents of the University of Califonia, Oakland, CA (US)

( * ) Notice: Subject to any disclaimer, the term of this patent is extended or adjusted under 35 U.S.C. 154(b) by 132 days.

This patent is subject to a terminal disclaimer.

(21) Appl. No.: 12/498,334

(22) Filed: Jul. 6, 2009

(65) Prior Publication Data
US 2010/0121059 A1    May 13, 2010

Related U.S. Application Data

(63) Continuation of application No. 10/958,997, filed on Oct. 4, 2004, now Pat. No. 7,557,138.

(51) Int. Cl.
*A61K 31/37* (2006.01)
*C07D 493/04* (2006.01)
(52) U.S. Cl. ........................................ 514/455; 549/282
(58) Field of Classification Search .................. 549/282; 514/455
See application file for complete search history.

(56) References Cited

OTHER PUBLICATIONS

Vennekamp et al, Molecular Pharmacology, vol. 65, No. 9, p. 1364-1374 (2004).*

* cited by examiner

*Primary Examiner* — Bernard Dentz
(74) *Attorney, Agent, or Firm* — Robert D. Buyan; Stout, Uxa, Buyan & Mullins

(57) ABSTRACT

Compositions of matter comprising 5-phenoxyalkoxypsoralen compounds and their method of synthesis and use. The compounds are useable to treat diseases or disorders in human or animal subjects, including autoimmune diseases. The compounds inhibit potassium channels, including the Kv1.3 channel and at least some of the therapeutic effects of such compounds may be due at least in part to potassium channel inhibition. In some embodiments, the compounds are more selective for certain potassium channels (e.g., Kv1.3 channels) than other potassium channels (e.g., Kv1.5 channels).

10 Claims, No Drawings

# 5-PHENOXYALKOXYPSORALENS AND METHODS FOR SELECTIVE INHIBITION OF THE VOLTAGE GATED KV1.3 POTASSIUM CHANNEL

RELATED APPLICATION

This patent application is a continuation of copending U.S. patent application Ser. No. 10/958,997 filed Oct. 4, 2004, the entire disclosure of which is expressly incorporated herein by reference.

FIELD OF THE INVENTION

The present invention provides a) novel compositions of matter comprising or consisting of 5-phenoxyalkoxypsoralens, b) methods for treating and/or preventing diseases or disorders in human or animal subjects, c) methods and kits for in vivo and/or in vitro inhibition of the selected types of potassium channels and d) the use of 5-phenoxyalkoxypsoralen compositions in the manufacture of pharmaceutical preparations for the treatment and/or prevention of diseases or disorders in human or animal subjects.

BACKGROUND OF THE INVENTION

T Cells and Their Functions

T cells are lymphocytes that have receptors capable of recognizing protein fragments (antigens) derived from foreign, potentially harmful proteins or organisms such as bacteria and viruses or from proteins present in the body of the host. Each T cell receptor recognizes a different string of amino acids, which comprise the antigen. Essentially there will always be at least one T cell receptor in the total repertoire of T cells, which will recognize any given antigen, which is in the body.

There are two main types of T cells, namely CD4+ helper T cells and CD8+ killer T cells. Helper T Cells (Th) carry receptors that engage antigens present on the surfaces of an antigen-presenting cell (APC) such as dendritic cells and sometimes macrophages. It is only by engagement with an antigen present on an APC and a subsequent process known as co-stimulation that a Th cell can become activated so that it may attack that specific antigen. Before the Th cell has become activated it is known as a "naïve" T cell. After the Th cell has become activated it becomes an "effector" T cell and wages an immune attack against the particular antigen. After cells containing the antigen have been destroyed, most of the effector T cells die. However, some effector T cells remain in a resting or quiescent state and are then known as "memory T cells." At least two types of Memory T cells exist, each having different migratory characteristics and effector functions. The first type of memory T cells are known as "effector memory T cells" ($T_{EM}$) and produce IFN-γ, TNF-α and IL-2 or pre-stored perforin (in the case of CD8s) when they encouner an antigen. The second type of memory T cells, known as "central memory T cells" ($T_{CM}$), express the chemokine receptor CCR7 similar to naïve T cells and lack immediate effector function. When $T_{EM}$ cells encounter the same antigen that initially caused their activation, they quickly convert back to effector T cells without the need for co-stimulation. Such rapid redeployment of effector T cells without the need for co-stimulation allows the immune system to attack the antigen in a very efficient manner.

Ion Channels: Molecular Targets for Pharmacologic Intervention

Ion channels are proteins embedded within the cell membrane that control the selective flux of ions across the membrane, thereby allowing the rapid movement of ions during electrical signaling processes. Because ion concentrations are directly involved in the electrical activity of excitable cells (e.g., neurons), the functioning (or malfunctioning) of ion channels can substantially control the electrical properties and behavior of such cells. Indeed, a variety of disorders, broadly termed as "channelopathies," are believed to be linked to ion channel insufficiencies or dysfunctions.

Ion channels are referred to as "gated" if they can be opened or closed. The basic types of gated ion channels include a) ligand-gated channels, b) mechanically gated channels and c) voltage-gated channels. In particular, voltage-gated channels are found in neurons and muscle cells. They open or close in response to changes in the potential differences across the plasma membrane.

In recent years, drug development efforts have included work aimed at identifying and characterizing various ion channels and designing agents that increase or decrease the flux of ions through those ion channels to bring about desired therapeutic effects.

Kv1.3 Channels and Their Roll in T Cell Physiology.

The predominant voltage-gated potassium ion channel in human T-lymphocytes is encoded by Kv1.3, a Shaker-related gene. Kv1.3 channels have been characterized extensively at the molecular and physiological level and are known to play a vital role in controlling T-lymphocyte proliferation, mainly by maintaining the membrane potential of resting T-lymphocytes. For example, encephalitogenic and arthritogenic rat T cells that have been chronically activated with myelin antigens have been shown to express a unique channel phenotype (high Kv1.3 channels and low IKCa1 channels), distinct from that seen in quiescent and acutely activated T cells (Beeton et al., 2001, Selective blockade of T lymphocyte K(+) channels ameliorates experimental autoimmune encephalomyelitis, a model for multiple sclerosis. Proc. Natl. Acad. Sci. USA 98:13942) and such findings have been confirmed in myelin antigen specific T cells from human patients suffering from multiple sclerosis (MS). Contrary to myelin-reactive T cells from healthy controls and to mitogen or control antigen activated T cells from MS patients, myelin reactive T cells from MS patients predominantly expressed surface markers of terminally differentiated effector memory T cells (CCR7⁻ CD45RA⁻) and exhibited the $Kv1.3^{high}IKCa1^{low}$ phenotype (Wulff et al., The voltage-gated Kv1.3 K(+) channel in effector memory T cells as new target for MS. 2003, J. Clin. Invest. 111:1703). In the same study, it was shown that this special K⁺ channel phenotype made the proliferation of effector memory T cells highly sensitive to inhibition by Kv1.3 blockers. Naïve and central memory T cells were only affected at 10-fold higher concentrations of Kv1.3 blockers and could escape Kv1.3 inhibition during subsequent stimulation through the up-regulation of the calcium-activated potassium channel IKCa1. Thus, it may be possible to develop a selective potassium channel blocker that will target the disease-inducing effector memory T cell population without affecting the normal immune response.

Kv1.3 and IKCa1 Expression and Functional Roles in Naïve and Memory T-cells

Naïve, central memory ($T_{CM}$) and effector memory T ($T_{EM}$) cells are classified based on the expression of the chemokine receptor CCR7 and the phosphatase CD45RA. Naïve (CCR7⁺CD45RA⁺) and $T_{CM}$ (CCR7⁺CD45RA⁻) cells migrate to the lymph node using CCR7 as an entry code, before migrating to sites of inflammation. In contrast, $T_{EM}$ cells have the ability to home directly to sites of inflammation, where they can secrete high amounts of interferon (IFN-γ) and tumor necrosis factor-α (TNF-α) and exhibit immediate effector function. The expression patterns of Kv1.3 and IKCa1 change dramatically as naïve cells become memory cells. At rest, CD4+ and CD8+ T-cells of all three subsets exhibit ~200 to 400 Kv1.3 channels, and 0 to 30 IKCa1 channels (Wulff et al., *The voltage-gated Kv1.3 K(+) channel in effector memory T cells as new target for MS*. 2003, J. Clin. Invest. 111:1703). Activation has diametrically opposite effects on channel expression; as naïve and $T_{CM}$ cells move from resting to proliferating blast cells, they transcriptionally up-regulate IKCa1 to ~500 channels per cell. In contrast, activation of $T_{EM}$ cells enhances Kv1.3 expression without any change in IKCa1 levels (Wulff et al., 2003, J. Clin. Invest. 111:1703). Functional Kv1.3 expression increases dramatically within 15 h of activation to a level of 1500 Kv1.3 channels/cell, remains elevated for the following 48 to 72 h, and then returns to baseline over the next five days (Beeton et al., A novel fluorescent toxin to detect and investigate Kv1.3 channel up-regulation in chronically activated T lymphocytes. 2003, J. Biol. Chem. 278:9928)

The subset-specific channel expression has important functional consequences, since Kv1.3 and IKCa1 regulate $Ca^{2+}$ entry into T-cells through $Ca^{2+}$-release-activated $Ca^{2+}$ channels that exhibit 'upside-down' voltage-dependence compared with voltage-gated $Ca^{2+}$ channels. A negative membrane potential drives $Ca^{2+}$ entry through these channels. The electrochemical gradient supporting $Ca^{2+}$ entry is initially large, resulting in significant $Ca^{2+}$ influx. However, $Ca^{2+}$ entry results in depolarization of the plasma membrane, limiting further influx. To maintain $Ca^{2+}$ entry over the time scale required for gene transcription, a balancing cation efflux is necessary; this is provided by the efflux of $K^+$ ions through Kv1.3 and/or IKCa1 channels, which supply the electrochemical driving force for $Ca^{2+}$ entry via membrane hyperpolarization.

Depolarization resulting from Kv1.3 and IKCa1 blockade is inhibitory for $Ca^{2+}$ influx, signaling and lymphocyte activation. As Kv1.3 channels predominate in resting T-cells of the three subsets, the Kv1.3 blocker ShK, but not the IKCa1 blocker TRAM-34, suppress antigen or mitogen-driven activation. However, ShK is 10-fold more effective on $T_{EM}$ cells than on naïve and $T_{CM}$ cells ($IC_{50}$ values of 400 pM and 4 nM, respectively), due to the fact that the latter cells rapidly up-regulate IKCa1 after stimulation and become less sensitive to Kv1.3 inhibitors (Wulff et al., The voltage-gated Kv1.3 K(+) channel in effector memory T cells as new target for MS. 2003, J. Clin. Invest. 111:1703). Once IKCa1 is up-regulated in naïve and $T_{CM}$ cells, the reactivation of these cells is sensitive to IKCa1 but not Kv1.3 blockade. Naïve and $T_{CM}$ cells can up-regulate IKCa1 following mitogen or antigen stimulation, even if their initial activation is suppressed by Kv1.3 blockade; and can consequently escape further inhibition by Kv1.3 inhibitors (Wulff et al., 2003, J. Clin. Invest. 111: 1703). Early in vivo studies support these in vitro findings. The Kv1.3 blockers MgTX (Koo et al., Blockade of the voltage-gated potassium channel Kv1.3 inhibits immune responses in vivo. 1997, J. Immunol. 158:1520) and correolide (Koo et al., Correolide and derivatives are novel immunosuppressants blocking the lymphocyte Kv1.3 potassium channels. 1999, Cell Immunol. 197:99) effectively suppress the primary delayed-type hypersensitivity (DTH) response in mini-pigs, but are much less effective in suppressing the secondary DTH response, presumably due to the fact that the activated naïve or $T_{CM}$ cells involved have up-regulated IKCa1 expression. In contrast, $T_{EM}$ cells exclusively up-regulate Kv1.3 channels, and are persistently suppressed by Kv1.3 inhibitors.

Kv1.3 and IKCa1 Expression and Functional Roles in Naïve and Memory B-cells

A similar change in potassium channel expression takes place during the differentiation from naïve into class-switched memory B cells. While naïve ($IgD^+CD27^-$) and "early" memory B cells ($IgD^+CD27^+$) rely on IKCa1 for their proliferation, class-switched ($IgD^-CD27^+$) memory B cells rely on Kv1.3 and their proliferation is therefore potently inhibited by the Kv1.3 blockers ShK and Psora-4 (Wulff et al. K + channel expression during B cell differentiation: implications for immunomodulation and autoimmunity. 2004. J. Immunol. 173:776-86). Thus, Kv1.3 blockers selectively target "late" memory responses in both the T- and B-cell lineage should be useful for the treatment of autoimmune disorders.

Kv1.5 Channels and Regulation/Deregulation of Cardiac Rhythm

Ion flux through voltage gated potassium channels also plays a role in regulation of cardiac rhythms. Atrial fibrillation (AF) is a common cardiac rhythm disturbance. AF can be treated or prevented by agents that prolong the atrial action potential duration and refractoriness. Indeed, drugs such as dofetilide, almokalant, amiodarone and d-sotalol can effectively suppress AF. However, such drugs may also prolong the ventricular action potential duration, thereby giving rise to life threatening or lethal ventricular arrhythmias. This potential for antiarrhythmic drugs to actually cause certain types of arrhythmias while preventing others is sometimes referred to as the drug's "proarrhythmic potential." Proarrhythmic potential is an important dose-limiting factor in the use of antiarrhythmic drugs. In fact, a common proarrhythmic event reported to result from the use of traditional antiarrhythmic drugs that prolong ventricular repolarization (QT interval) to treat AF is a condition known as torsades de pointes, which is a rapid polymorphic ventricular tachycardia.

Because voltage gated Kv1.5 potassium channels are predominantly located in atrial tissue, drugs that inhibit Kv1.5 channels are being developed for the treatment of AF (Brendel, J. and Peukert, S.; *Blockers of the Kv1.5 Channel for the Treatment of Atrial Arrhythmias*; Current Medicinal Chemistry—Cardiovascular & Hematological Agents, Volume 1, No. 3, 273-287 (2003)). Drugs that selectively inhibit Kv1.5 channels could prove to be a viable new approach for the treatment of AF with minimal or no proarrhythmic potential. However, it is also possible that, untoward inhibition of Kv1.5 channels in patients who have normal heart rhythms could induce an electrical imbalance and actually cause arrhythmias in such patients. Thus, when developing drugs that are intended to inhibit potassium channels other than Kv1.5 (e.g., drugs intended to inhibit Kv1.3 channels to treat T cell mediated diseases), it may be desirable to design these drugs to display selectivity for the target potassium channels (e.g., Kv1.3 channels) over the heart-affecting Kv1.5 channels.

In view of the foregoing, there remains a need for the synthesis and development of new potassium channel inhibitors that are specific for certain potassium channels over other potassium channels, thereby providing specific therapeutic effects with minimal side effects.

SUMMARY OF THE INVENTION

The present invention provides 5-Phenoxyalkoxypsoralens, a new class of small-molecules that block the Kv1.3 channel in the low nanomolar range and preferentially suppress the proliferation of effector memory T cells and affect naïve and central memory T cells only at much higher concentrations. Given the known in vitro and in vivo effects of peptide and non-peptide inhibitors of the Kv1.3 channel, the present invention further comprises the therapeutic and/or diagnostic use of these 5-phenoxyalkoxypsoralens for any diagnosis or treatment that results from or is facilitated by blocking or inhibiting of the Kv1.3 channel, including but not limited to the use of 5-phenoxyalkoxypsoralens as immunosuppressants and/or for the treatment of multiple sclerosis, rheumatoid arthritis, graft rejection and/or any autoimmune disorders.

In accordance with the invention there are provided compositions of matter comprising or consisting of 5-phenoxyalkoxypsoralens of general Formula I, as follows:

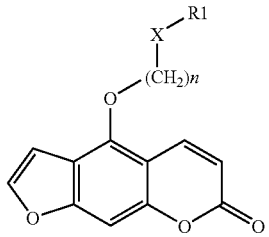

General Formula 1 wherein:

n is 1 through 10, cyclic or acyclic and optionally substituted or unsubstituted;

X is O, S, N, C Si or P; and

R1 is aryl, heterocyclyl or cycloalkyl and is optionally substituted with one or more substituents selected from alkyl, alkoxy, amino and its alkyl derivatives, acylamino, carboxyl and its alkyl ester, cyano, halo, hydroxy, nitro and sulfonamido groups.

Further in accordance with the present invention, there are provided pharmaceutical preparations for administration to human or veterinary patients, said preparations comprising a 5-Phenoxyalkoxypsoralen of General Formula I above or a pharmaceutically acceptable salt thereof alone or in combination with pharmaceutically acceptable carriers, excipients and other ingredients commonly used in pharmaceutical preparations for oral, rectal, intravenous, intraarterial, intradermal, subcutaneous, intramuscular, intrathecal, sublingual, bucal, intranasal, trans-mucosal, trans-dermal, topical, other enteral, other parenteral and/or other possible route(s) of administration.

Still further in accordance with the invention, there are provided methods for treating or preventing diseases or disorders in human or animal subjects by administering to the subject a therapeutic or preventative amount of a composition of General Formula I above or a pharmaceutically acceptable salt or derivative thereof. Various diseases and disorders may be treated or prevented by inhibiting selected types of potassium channels. For example, compositions of the present invention that inhibit Kv1.3 channels on human T cells may be used to treat or prevent T cell mediated diseases or disorders, such as various autoimmune diseases and disorders. The following are some non-limiting examples of some T cell mediated autoimmune diseases or disorders that may be prevented or treated by the methods of the present invention, categorized with respect to the target organ that is principally affected by each such disease:

Nervous System:

Multiple sclerosis
Myasthenia gravis
Autoimmune neuropathies
such as Guillain-Barré
Autoimmune uveitis
Ophthalmologic:

Uveitis
Blood:

Autoimmune hemolytic anemia
Pernicious anemia
Autoimmune
thrombocytopenia
Vascular:

Temporal arteritis
Anti-phospholipid syndrome
Vasculitides such as
Wegener's granulomatosis
Behcet's disease
Skin:

Psoriasis
Dermatitis herpetiformis
Pemphigus vulgaris
Vitiligo
Pemphigus Vulgaris
Mycosis Fungoides
Allergic Contact Dermatitis,
Atopic Dermatitis
Lichen Planus
PLEVA (Pityriasis lichenoides
et varioliforms acuta),
Gastrointestinal Tract:

Crohn's Disease
Ulcerative colitis
Primary biliary cirrhosis
Autoimmune hepatitis
Endocrine:

Type 1 diabetes mellitus
Addison's Disease
Grave's Disease
Hashimoto's thyroiditis
Autoimmune oophoritis and
orchitis
Autoimmune Thyroiditis
Multiple Organs and/or
Musculoskeletal System:

Rheumatoid arthritis
Systemic lupus erythematosus
Scleroderma
Polymyositis
Dermatomyositis
Spondyloarthropathies such as
ankylosing spondylitis
Sjogren's Syndrome Irrespective of the particular organ(s) affected, T-lymphocytes are believed to contribute to the development of autoimmune diseases. The currently available therapies for these diseases are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506. Also, another T cell mediated disorder that may be prevented or treated by the methods of the present invention is graft vs. host disease and/or rejection of transplanted organs. T-lymphocytes play a central role in the immune response and they are responsible, in large measure, for the rejection of many transplanted organs. They are also responsible for the so-called graft-versus host disease in which transplanted bone marrow cells recognize and destroy MHC-mismatched host tissues. Accordingly, drugs such as cyclosporin and FK506 that suppress T-cell immunity are used to prevent transplant rejection and graft-versus-host disease. However, immunosuppressive therapy with cyclosporin A is limited by severe side effects such as liver and renal damage. Selective inhibitors of the Kv1.3 potassium channel, such as the 5-Phenoxyalkoxypsoralens of General Formula I above, may be less likely to cause such side effects and, thus, may be used alone or in combination with other agents (e.g., cyclosporin and/or FK506) to treat or prevent rejection of transplanted tissues or organs and/or graft vs. host disease. Also, inhibitors of the voltage gated Kv1.3 potassium channel have been shown to be especially effective in suppressing effector memory T cells and, thus, the methods of present invention may be particularly effective in preventing or treating diseases that are associated with effector memory T cells, such as; bone resorption and periodontal disease, psoriasis, rheumatoid arthritis, type-1 diabetes mellitus and multiple sclerosis. In addition to T cell mediated diseases, the Kv1.3 channel has been determined to regulate energy homeostasis, body weight and peripheral insulin sensitivity. Thus, the methods of the present invention may be used to treat other diseases and disorders that involve abnormal homeostasis, body weight and peripheral insulin sensitivity by inhibiting Kv1.3 channels on cell membranes, such other diseases and disorders include but are not necessarily limited to bone resorption in periodontal disease, Type 2 diabetes, metabolic syndrome and obesity. Additionally, for Multiple Sclerosis in particular, the current therapy with interferon-beta and copaxone only benefits about 60% of patients. The appearance of neutralizing antibodies in around 40% of patients treated with interferon-beta makes interferon-beta treatment less effective over time in the responsive patients. Thus, the 5-Phenoxyalkoxypsoralens disclosed herein may provide substantial improvements in the treatment of MS.

Still further in accordance with the present invention, there are provided methods for causing a desired inhibition of a first type of potassium channel (e.g., Kv1.3 channels) while not causing undesired inhibition of a second type of potassium channel (e.g., Kv1.5 channels) in a human or animal subject. Such methods generally comprise the step of administering to the human or animal subject a compound of General Formula I in an amount and form that a) causes the desired inhibition of potassium channels of the first type but b) does not cause the undesired inhibition of potassium channels of the second type. The "desired inhibition of a first type of potassium channel" can be, for example, any inhibition of any type of potassium channel that causes an intended therapeutic or preventative effect, such as inhibition of Kv1.3 potassium channels to treat or prevent a T cell mediated disorder in the human or animal subject. The "undesired inhibition of a second type of potassium channel" can be, for example, any inhibition of any type of potassium channel that causes a side effect, untoward effect or any effect other than the desired therapeutic or preventative effect, such as the inhibition of Kv1.5 potassium channels in a way that causes a proarrhythmic effect or increases the potential for cardiac arrhythmia in the human or animal subject.

Still further in accordance with the present invention, there are provided methods for inhibiting potassium channels in vitro by contacting cells with one or more compounds of General Formula I. Such methods may be useful in pharmacologic research and/or for screening of drug candidates. Specific compounds of General Formula I may be selected for use in these methods on the basis of their relative inhibitory selectivity for certain type(s) of potassium channels over other type(s) of potassium channels.

Still further aspects, objects and advantages of the invention will become apparent to persons of skill in the art upon reading and understanding of the detailed descriptions of the preferred embodiments set forth herebelow.

DETAILED DESCRIPTION AND EXAMPLES

The following detailed description and the accompanying drawings are intended to describe some, but not necessarily all, examples or embodiments of the invention only and does not limit the scope of the invention in any way.

Set forth herebelow are some examples of substituted 5-phenoxyalkoxypsoralens of the present invention that inhibit the Kv1.3 channel and suppress the proliferation of effector memory T cells in the low nanomolar concentrations.

Example 1

5-(4-Phenoxybutoxy)psoralen (PAP 1)

4-(4-Phenoxybutoxy)-7H-furo[3,2-g][1]benzopyran-7-on

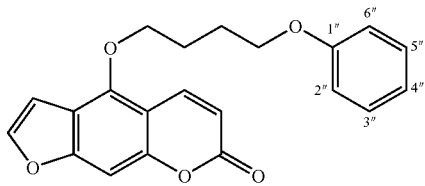

700 mg (3.462 mmol) of 5-hydroxypsoralen (crystallized) and 600 mg (3.462 mmol) of 4-phenoxybutyl bromide was refluxed in 30 ml of 2-butanone in the presence of an excess (2 g) of anhydrous potassium carbonate and catalytic amounts of potassium iodide for 24 hours. The progress of the reaction was monitored by thin layer chromatography. After 24 hours the reaction mixture was concentrated under reduced pressure. The oily residue was cooled and diluted with water. The aqueous solution was then acidified with concentrated hydrochloric acid to pH 1. The slurry was stirred for 15-20 min and extracted with 3×100 ml of dichloromethane. The dichloromethane layer was extracted with 25 ml of 1% sodium hydroxide to separate the un-reacted 5-hydroxypsoralen. The dichloromethane layer was washed with 30 ml of 2% hydrochloric acid, dried over anhydrous sodium sulfate and concentrated. The solid residue was dissolved in a methanol-acetone mixture, treated with charcoal and re-crystallized from a methanol-acetone (80:20) mixture.

Yield: 733.6 mg (60.48%)

Melting point: 104° C.

$^1$H-NMR (500 MHz, CDCl$_3$): δ [ppm]=8.13 (d, 1H, $^3$J=9.7 Hz, 3-H), 7.59 (d, 1H, $^3$J=2.0 Hz, 2'-H), 7.30 (m, 5H, 5-OCH$_2$CH$_2$CH$_2$CH$_2$OC$_6$H$_5$), 7.15 (s, 1H, 8-H), 6.91 (d, 1H, $^3$J=2.0 Hz, 3'-H), 6.25 (d, 1H, $^3$J=9.8 Hz, 4-H), 4.56 (t, 2H, $^3$J=6.14 Hz, 5-OCH$_2$CH$_2$CH$_2$CH$_2$OC$_6$H$_5$), 4.09 (t, 2H, $^3$J=5.80 Hz, 5-OCH$_2$CH$_2$CH$_2$CH$_2$OC$_6$H$_5$), 2.09 (m, 4H, $^3$J=4.21 Hz, 5-OCH$_2$CH$_2$CH$_2$CH$_2$OC$_6$H$_5$).

$^{13}$C-NMR (DMSO-d$_6$, 75 MHz): δ [ppm]=25.26 and 26.18 (5-O—CH$_2$(CH$_2$)$_2$CH$_2$—O—C$_6$H$_5$); 66.91 and 72.29 (5-O—CH$_2$(CH$_2$)$_2$CH$_2$—O—C$_6$H$_5$); 93.18 (C-8); 105.62 (C-4'); 105.98 (C-4a); 112.29 (C-3); 112.92 (C-6); 114.39

(C-3" and C-5"); 120.39 (C-4"); 129.41 (C-2" and C-6"); 139.44 (C-4); 145.89 (C-5'); 148.72 (C-5); 152.11 (C-8a); 157.63 (C-1"); 158.48 (C-7); 160.07 (C-2).

MS (70 eV) m/z: 350 (20%, M$^+$), 202 (9%, [M-C$_{10}$H$_{12}$O]$^+$), 201 (5%), 174 (13%, [202-CO]$^+$), 173 (4%), 150 (11%), 149 (100%), 145 (8%), 107 (100%, [149-C$_3$H$_6$]$^+$), 94 (9%, C$_6$H$_6$O), 89 (4%), 77 (37%, C$_6$H$_5$), 65 (6%, C$_5$H$_5$).

Combustion analysis: (FW: 350.37) % C, 71.92; % H, 5.08. (Calc. % C, 71.99; % H, 5.18)

Example 2

5-(3-Phenoxypropoxy)psoralen (PAP 3)

4-(3-Phenoxypropoxy)-7H-furo[3,2-g][1]benzopyran-7-on

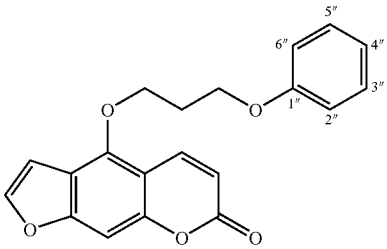

700 mg (3.5 mmol) of 5-hydroxypsoralen and 750 mg (3.5 mmol) of 3-phenoxypropyl bromide were refluxed in 30 ml of 2-butanone in the presence of an excess of anhydrous potassium carbonate (3.0 g) and catalytic amounts of potassium iodide for 36 hours. The progress of the reaction was monitored by thin layer chromatography. After 36 hours the reaction mixture was concentrated under reduced pressure. The oily residue was cooled and diluted with water. The aqueous solution was then acidified with concentrated hydrochloric acid to pH 1. The slurry was stirred for 15-20 min and extracted with 3×30 ml of dichloromethane. The dichloromethane layer was extracted with 25 ml of 1% sodium hydroxide to separate the un-reacted 5-hydroxypsoralen. The dichloromethane layer was washed with 30 ml of 2% hydrochloric acid, dried over anhydrous sodium sulfate and concentrated. The resulting oily residue was dissolved in methanol, treated with charcoal and re-crystallized from a methanol-ethyl acetate (10:90) mixture.

Yield: 390 mg (33.48%).

Melting point: 108.4° C.

$^1$H-NMR (500 MHz, CDCl$_3$): δ [ppm]=8.13 (d, 1H, $^3$J=9.8 Hz, 3-H), 7.59 (d, 1H, $^3$J=2.3 Hz, 2'-H), 7.31 (t, 3H, 3"-H, 4"-H, 5"-H), 7.16 (s, 1H, 8-H), 6.99 (d, 1H, $^3$J=2.4 Hz, 3'-H), 6.93 (d, 2H, 2"-H, 6"-H), 6.24 (d, 1H, $^3$J=9.5 Hz, 4-H), 4.66 (t, 2H, $^3$J=5.9 Hz, 5-OCH$_2$CH$_2$CH$_2$OC$_6$H$_5$), 4.26 (t, 2H, $^3$J=6.0 Hz, 5-OCH$_2$CH$_2$CH$_2$OC$_6$H$_5$), 2.38 (p, 2H, $^3$J=6.0 Hz, 5-OCH$_2$CH$_2$OC$_6$H$_5$).

MS (70 eV) m/z: 336 (91%, M$^+$), 203 (7%), 202 (57%, [M-C$_9$H$_{10}$O]$^+$), 201 (11%), 174 (16%, [202-CO]$^+$), 173 (11%), 145 (14%), 135 (90%), 134 (9%), 108 (8%), 107 (100%), 95 (8%), 89 (9%), 77 (62%, C$_6$H$_5$), 65 (9%, C$_5$H$_5$).

Combustion analysis: (FW: 336.35) % C, 71.09; % H, 4.74 (Calc. % C, 71.42; % H, 4.79)

Example 3

5-(2-Benzyloxyethoxy)psoralen (PAP 5)

4-(2-Benzyloxyethoxy)-7H-furo[3,2-g][1]benzopyran-7-on

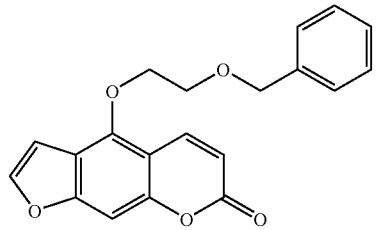

600 mg (2.967 mmol) of 5-hydroxypsoralen and 1.0 g (4.649 mmol) of benzyl-2-bromoethyl ether were refluxed in 30 ml of 2-butanone in the presence of an excess of anhydrous potassium carbonate (2.0 g) and catalytic amounts of potassium iodide for 16 hours. The progress of the reaction was monitored by thin layer chromatography. After 16 hours the reaction mixture was concentrated under reduced pressure. The oily residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 25 ml of 1% sodium hydroxide to separate the un-reacted 5-hydroxypsoralen. The dichloromethane layer was washed with 30 ml of 2% hydrochloric acid, dried over anhydrous sodium sulfate and concentrated. The resulting oily residue was dissolved in methanol, treated with charcoal and re-crystallized from 70% methanol.

Yield: 123 mg (12.33%)

Melting point: 90.9° C.

$^1$H-NMR (500 MHz, CDCl$_3$): δ [ppm]=8.19 (d, 1H, $^3$J=9.7 Hz, 3-H), 7.59 (d, 1H, $^3$J=2.2 Hz, 2'-H), 7.37 (m, 5H, 5-OCH$_2$CH$_2$OCH$_2$C$_6$H$_5$), 7.19 (s, 1H, 8-H), 6.95 (d, 1H, $^3$J=2.0 Hz, 3'-H), 6.25 (d, 1H, $^3$J=9.7 Hz, 4-H), 4.64 (s, 2H, 5-OCH$_2$CH$_2$OCH$_2$C$_6$H$_5$), 4.58 (t, 2H, $^3$J=4.62 Hz, 5-OCH$_2$CH$_2$OCH$_2$C$_6$H$_5$), 3.88 (t, 2H, $^3$J=4.56 Hz, 5-OCH$_2$CH$_2$OCH$_2$C$_6$H$_5$).

MS (70 eV) m/z: 336 (35%, M$^+$), 105 (5%), 91 (100%, [C$_7$H$_7$]$^+$).

Combustion analysis: (FW: 336.35) % C, 70.65; % H, 4.73 (Calc. % C, 71.42; % H, 4.79)

Example 4

5-(4-Benzyloxybutoxy)psoralen (PAP 6)

4-(4-Benzyloxybutoxy)-7H-furo[3,2-g][1]benzopyran-7-on

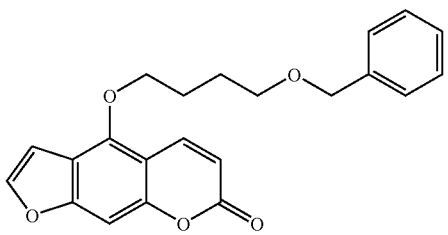

700 mg (3.5 mmol) of 5-hydroxypsoralen and 850.5 mg (3.5 mmol) of benzyl-4-bromobutyl ether was refluxed in 30 ml of 2-butanone in the presence of an excess of anhydrous potassium carbonate (2.0 g) and catalytic amounts of potassium iodide for 24 hours. The progress of the reaction was monitored by thin layer chromatography. After 24 hours the reaction mixture was concentrated under reduced pressure. The oily residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 25 ml of 1% sodium hydroxide to separate the un-reacted 5-hydroxypsoralen. The dichloromethane layer was washed with 30 ml of 2% hydrochloric acid, dried over anhydrous sodium sulfate and concentrated. The oily residue was dissolved in methanol, treated with charcoal and re-crystallized from 80% methanol.

Yield: 171 mg (13.41%)

Melting point: 78.4° C.

$^1$H-NMR (500 MHz, CDCl$_3$): δ [ppm]=8.14 (d, 1H, $^3$J=9.8 Hz, 3-H), 7.55 (d, 1H, $^3$J=2.5 Hz, 2'-H), 7.34 (m, 5H, 5-OCH$_2$CH$_2$CH$_2$CH$_2$OCH$_2$C$_6$H$_5$), 7.13 (s, 1H, 8-H), 6.91 (d, 1H, $^3$J=2.4 Hz, 3'-H), 6.25 (d, 1H, $^3$J=9.8 Hz, 4-H), 4.54 (s, 2H, 5-OCH$_2$CH$_2$CH$_2$CH$_2$OCH$_2$C$_6$H$_5$), 4.49 (t, 2H, $^3$J=6.5 Hz, 5-OCH$_2$CH$_2$CH$_2$CH$_2$OCH$_2$C$_6$H$_5$), 3.59 (t, 2H, $^3$J=6.1 Hz, 5-OCH$_2$CH$_2$CH$_2$CH$_2$OCH$_2$C$_6$H$_5$), 2.00 (p, 2H, $^3$J=6.9 Hz, 5-OCH$_2$CH$_2$CH$_2$CH$_2$OCH$_2$C$_6$H$_5$), 1.87 (p, 2H, $^3$J=6.8 Hz, 5-OCH$_2$CH$_2$CH$_2$CH$_2$OCH$_2$ $_{C_6}$H$_5$).

MS (70 eV) m/z: 364 (37%, M$^+$), 292 (10%), 202 (7%, [M-C$_{11}$H$_{14}$O]$^+$), 174 (6%, [202-CO]$^+$), 163 (12%), 91 (100%, C$_7$H$_7$), 71 (8%).

Combustion analysis: (FW: 364.40) % C, 72.36; % H, 5.46 (Calc. % C, 72.51; % H, 5.53)

Example 5

5-(3-Benzyloxypropoxy)psoralen (PAP 7)

4-(3-Benzyloxypropoxy)-7H-furo[3,2-g][1]benzopyran-7-on

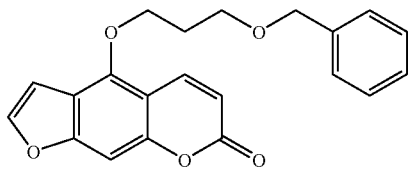

1.0 g (4.946 mmol) of 5-hydroxypsoralen and 1.36 g (5.936 mmol) of benzyl-3-bromopropyl ether were refluxed in 30 ml of 2-butanone in the presence of an excess of anhydrous potassium carbonate (3.4 g) and catalytic amounts of potassium iodide for 24 hours. The progress of the reaction was monitored by thin layer chromatography. After 24 hours the reaction mixture was concentrated under reduced pressure. The oily residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 25 ml of 1% sodium hydroxide to separate the un-reacted 5-hydroxypsoralen. The dichloromethane layer was washed with 30 ml of 2% hydrochloric acid solution, dried over anhydrous sodium sulfate and concentrated. The resulting oily residue was dissolved in methanol, treated with charcoal and re-crystallized from 70% methanol-water mixture.

Yield: 700 mg (40.39%)

Melting point: 75.2° C.

$^1$H-NMR (500 MHz, CDCl$_3$): δ [ppm]=8.06 (d, 1H, $^3$J=9.7 Hz, 3-H), 7.57 (d, 1H, $^3$J=2.2 Hz, 2'-H), 7.29 (m, 5H, $^3$J=6.3 Hz, 5-OCH$_2$CH$_2$CH$_2$OCH$_2$C$_6$H$_5$), 7.15 (s, 1H, 8-H), 6.98 (d, 1H, $^3$J=2.2 Hz, 3'-H), 6.21 (d, 1H, $^3$J=9.8 Hz, 4-H), 4.58 (t, 2H, $^3$J=6.1 Hz, 5-OCH$_2$CH$_2$CH$_2$OCH$_2$C$_6$H$_5$), 4.55 (s, 2H, 5-OCH$_2$CH$_2$CH$_2$OCH$_2$C$_6$H$_5$), 3.73 (t, 2H, $^3$J=5.7 Hz, 5-OCH$_2$CH$_2$CH$_2$OCH$_2$C$_6$H$_5$), 2.18 (p, 2H, $^3$J=6.1 Hz, 5-OCH$_2$CH$_2$CH$_2$OCH$_2$C$_6$H$_5$).

MS (70 eV) m/z: 350 (25%, M$^+$), 202 (9%, [M-C$_{10}$H$_{12}$O]$^+$), 174 (5%, [202-CO]$^+$), 91 (100%, [C$_7$H$_7$]$^+$).

Combustion analysis: (FW: 350.37) % C, 71.64; % H, 5.34 (Calc. % C, 71.99; % H, 5.18)

Example 6

5-(4-Chlorobutoxy)psoralen (I 1)

4-(4-Chlorobutoxy)-7H-furo[3,2-g][1]benzopyran-7-on

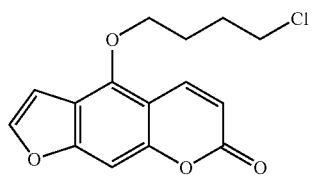

817 mg (4.041 mmol) of 5-hydroxypsoralen and 1.413 g (6.47 mmol) of 4-chlorobutyl iodide were refluxed in 80 ml of acetone in the presence of an excess of (3.0 g) anhydrous potassium carbonate for 30 hours. The progress of the reaction was monitored by thin layer chromatography. After 30 hours the reaction mixture was concentrated under reduced pressure and distilled off the solvent almost completely. The oily residue was cooled and diluted with water. The aqueous solution was then acidified with concentrated hydrochloric acid to pH 1. The slurry was stirred for 15-20 min and extracted with 3×100 ml of dichloromethane. The dichloromethane layer was extracted with 1×25 ml of 1% sodium hydroxide to separate trace amounts of un-reacted 5-hydroxypsoralen. The dichloromethane layer was washed with 30 ml of 2% hydrochloric acid and further washed with water to neutral pH. The dichloromethane layer was dried over anhydrous sodium sulfate and concentrated to dryness. The resulting residue was then suspended in petroleum ether and filtered to wash out the excess 4-chlorobutyl iodide. The resulting 5-(4-chlorobutoxy)psoralen was used for the synthesis of various derivatives without further purification.

Yield: 1.10 g (92.98%)

Melting point: 115.4-115.6° C.

$^1$H-NMR (500 MHz, CDCl$_3$): δ [ppm]=8.15 (d, 1H, $^3$J=9.75 Hz, 3-H), 7.60 (d, 1H, $^3$J=2.62 Hz, 2'-H), 7.17 (s, 1H, 8-H), 6.95 (d, 1H, $^3$J=2.15 Hz, 3'-H), 6.29 (d, 1H, $^3$J=9.79 Hz, 4-H), 4.52 (t, 2H, $^3$J=5.44 Hz, 5-OCH$_2$CH$_2$CH$_2$CH$_2$Cl), 3.68 (t, 2H, $^3$J=5.89 Hz, 5-OCH$_2$CH$_2$CH$_2$CH$_2$Cl), 2.08 (p, 4H, $^3$J=3.06 Hz, 5-OCH$_2$CH$_2$CH$_2$CH$_2$Cl).

Example 7

5-(4-{2"-Methoxy-4"-nitrophenoxy}butoxy)psoralen (PAP 10)

4-(4-{2"-Methoxy-4"-nitrophenoxy}butoxy)-7H-furo[3,2-g][1]benzopyran-7-on

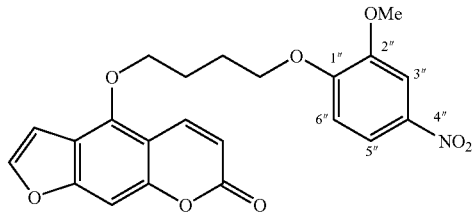

500 mg (1.708 mmol) of 5-(4-chlorobutoxy)psoralen, 741.41 mg (4.946 mmol) of sodium iodide were refluxed in 15 ml of anhydrous acetonitrile for 60 min to obtain the iodo derivative. To this solution were added 837 mg (4.946 mmol) of 4-nitroguaicol, an excess (3.0 g) of anhydrous potassium carbonate, 10 ml of anhydrous acetonitrile and the resulting mixture was refluxed for 72 hours. The progress of the reaction was monitored by thin layer chromatography. After 72 hours the reaction mixture was concentrated under reduced pressure. The residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 2×35 ml of 1% sodium hydroxide to separate the excess of 4-nitroguaicol. The dichloromethane layer was washed with 30 ml of 2% hydrochloric acid, dried over anhydrous sodium sulfate and concentrated. The resulting solid was dissolved in methanol-acetone mixture, treated with charcoal and re-crystallized from a methanol-acetone (80:20) mixture.

Yield: 381.9 mg (52.56%)
Melting point: 170.5° C.
$^1$H-NMR (500 MHz, CDCl$_3$): δ [ppm]=8.15 (d, 1H, $^3$J=9.8 Hz, 3-H), 7.91 (d, 1H, $^4$J=2.6 Hz, 3"-H), 7.75 (dd, 1H, $^3$J=2.65 Hz, 5"-H), 7.60 (d, 1H, $^3$J=2.2 Hz, 2'-H), 7.16 (s, 1H 8-H), 6.98 (d, 1H, $^3$J=2.4 Hz, 3'-H), 6.93 (d, 1H, $^3$J=2.2 Hz, 6"-H), 6.26 (d, 1H, $^3$J=9.7 Hz, 4-H), 4.59 (t, 2H, $^3$J=6.0 Hz, 5-OCH$_2$CH$_2$CH$_2$CH$_2$OC$_6$H$_3$[4-NO$_2$-2-CH$_3$O]), 4.23 (t, 2H, $^3$J=5.7 Hz, 5-OCH$_2$CH$_2$CH$_2$CH$_2$OC$_6$H$_3$[4-NO$_2$-2-CH$_3$O]), 3.915 (s, 3H, 2"-OCH$_3$), 2.14 (m, 4H, 5-OCH$_2$CH$_2$CH$_2$CH$_2$OC$_6$H$_3$[4-NO$_2$-2-CH$_3$O]).

Example 8

5-(4-{4"-Methyl-2"-nitrophenoxy}butoxy)psoralen (PAP 11)

4-(4-{4"-Methyl-2"-nitrophenoxy}butoxy)-7H-furo[3,2-g][1]benzopyran-7-on

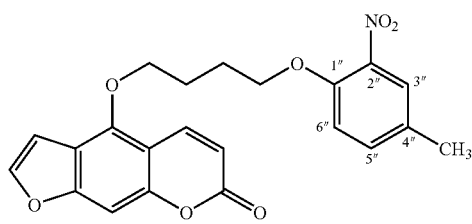

500 mg (1.708 mmol) of 5-(4-chlorobutoxy)psoralen, and 741 mg (4.946 mmol) of sodium iodide were refluxed in 15 ml of anhydrous acetonitrile for 60 min to obtain the iodo derivative. To this solution were added 523.2 mg (3.416 mmol) of 2-nitro-p-cresol, an excess of anhydrous potassium carbonate (4.0 g), 10 ml anhydrous acetonitrile and the resulting mixture was refluxed for 69 hours. The progress of the reaction was monitored by thin layer chromatography. After 69 hours the reaction mixture was concentrated under reduced pressure. The residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 2×30 ml of 1% sodium hydroxide to separate the excess of 2-nitro-p-cresol. The dichloromethane layer was washed with 30 ml of 2% hydrochloric acid, dried over anhydrous sodium sulfate and concentrated. The resulting residue was dissolved in methanol-acetone mixture, treated with charcoal and re-crystallized from a methanol-acetone (80:20) mixture.

Yield: 447.2 mg (63.95%)
Melting point: 124.5° C.
$^1$H-NMR (500 MHz, CDCl$_3$): δ [ppm]=8.14 (d, 1H, $^3$J=9.7 Hz, 3-H), 7.63 (d, 1H, $^4$J=1.8 Hz, 3"-H), 7.59 (d, 1H, $^3$J=2.4 Hz, 2'-H), 7.31 (d, 1H, $^3$J=8.2 Hz, 5"-H), 7.14 (s, 1H, 8-H), 6.98 (d, 1H, $^3$J=2.5 Hz, 3'-H), 6.96 (d, 1H, $^3$J=8.76 Hz, 6"-H), 6.26 (d, 1H, $^3$J=9.8 Hz, 4-H), 4.56 (t, 2H, $^3$J=5.7 Hz, 5-OCH$_2$CH$_2$CH$_2$CH$_2$OC$_6$H$_3$[4-CH$_3$-2-NO$_2$]), 4.17 (t, 2H, $^3$J=6.0 Hz, 5-OCH$_2$CH$_2$CH$_2$CH$_2$OC$_6$H$_3$[4-CH$_3$-2-NO$_2$]), 2.34 (s, 3H, 4"-CH$_3$), 2.05 (m, 4H, $^3$J=4.216 Hz, 5-OCH$_2$CH$_2$CH$_2$CH$_2$OC$_6$H$_3$[4-CH$_3$-2-NO$_2$]).

Example 9

5-(4-{2"-Nitrophenoxy}butoxy)psoralen (PAP 12)

4-(4-{2"-Nitrophenoxy}butoxy)-7H-furo[3,2-g][1]benzopyran-7-on

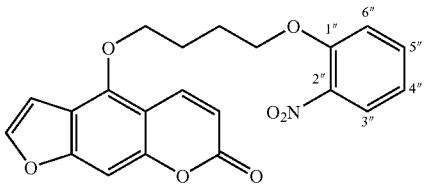

500 mg (1.708 mmol) of 5-(4-chlorobutoxy)psoralen, and 512 mg (3.416 mmol) of sodium iodide were refluxed in 15 ml of anhydrous acetonitrile for 60 min to obtain the iodo derivative. To this solution were added 475 mg (3.416 mmol) of 2-nitrophenol, an excess (4.0 g) of anhydrous potassium carbonate, 15 ml of anhydrous acetonitrile and the resulting mixture was refluxed for 29 hours. The progress of the reaction was monitored by thin layer chromatography. After 29 hours the reaction mixture was concentrated under reduced pressure. The residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 2×20 ml of 1% sodium hydroxide solution to separate the excess of 2-nitrophenol. The dichloromethane layer was washed with 30 ml of 2% hydrochloric acid solution, dried over anhydrous sodium sulfate and concentrated. The solid residue obtained was dissolved in methanol-acetone mixture, treated with charcoal and re-crystallized from a methanol-acetone (80:20) mixture.

Yield: 380.3 mg (56.32%)

Melting point: 121.6-121.8° C.

$^1$H-NMR (500 MHz, CDCl$_3$): δ [ppm]=8.14 (d, 1H, $^3$J=9.7 Hz, 3-H), 7.82-7.86 (overlapping dd, 2H, $^4$J=1.6 Hz, $^3$J=8.3 Hz, $^3$J=7.91 Hz, 3"-H, 6"-H), 7.60 (d, 1H, $^3$J=2.5 Hz, 2'-H), 7.52-7.55 (t, 2H, $^3$J=7.57 Hz, $^4$J=1.0 Hz, 3"-H, 4"-H), 7.15 (s, 1H, 8-H), 6.99 (d, 1H, $^3$J=2.35 Hz, 3'-H), 6.26 (d, 1H, $^3$J=9.7 Hz, 4-H), 4.57 (t, 2H, $^3$J=5.8 Hz, 5-OCH$_2$CH$_2$CH$_2$CH$_2$OC$_6$H$_4$[2-NO$_2$]), 4.23 (t, 2H, $^3$J=2.74 Hz, 5-OCH$_2$CH$_2$CH$_2$CH$_2$O C$_6$H$_4$[2-NO$_2$]), 2.09-2.16 (m, 4H, 5-OCH$_2$CH$_2$CH$_2$CH$_2$OC$_6$H$_4$[2-NO$_2$]).

Example 10

5-(4-{3"-Nitrophenoxy}butoxy)psoralen (PAP 13)

4-(4-{3"-Nitrophenoxy}butoxy)-7H-furo[3,2-g][1]benzopyran-7-on

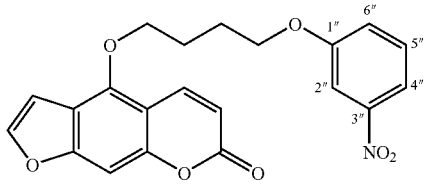

500 mg (1.708 mmol) of 5-(4-chlorobutoxy)psoralen and 512 mg (3.416 mmol) of sodium iodide were refluxed in 15 ml of anhydrous acetonitrile for 60 min to obtain the iodo derivative. To this solution were added 475 mg (3.416 mmol) of 3-nitrophenol, an excess (4.0 g) of anhydrous potassium carbonate, 15 ml anhydrous acetonitrile and the resulting mixture was refluxed for 29 hours. The progress of the reaction was monitored by thin layer chromatography. After 29 hours the reaction mixture was concentrated under reduced pressure. The residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 2×20 ml of 1% sodium hydroxide to separate the excess of 3-nitrophenol. The dichloromethane layer was washed with 30 ml of 2% hydrochloric acid, dried over anhydrous sodium sulfate and concentrated. The resulting residue was dissolved in methanol-acetone mixture, treated with charcoal and re-crystallized from a methanol-acetone (80:20) mixture.

Yield: 286.4 mg (42.41%)

Melting point: 140.3° C.

$^1$H-NMR (500 MHz, CDCl$_3$): δ [ppm]=8.15 (d, 1H, $^3$J=9.7 Hz, 3-H), 7.84 (dd, 1H, $^3$J=8.1 Hz, $^4$J=1.6 Hz, 4"-H), 7.61 (d, 1H, $^3$J=2.3 Hz, 2'-H), 7.42 (t, 1H, $^3$J=8.3 Hz, 5"-H), 7.41 (t, 1H, $^4$J=2.2 Hz, 2"-H), 7.22 (dd, 1H, $^3$J=8.1 Hz, $^4$J=2.3 Hz, 6"-H) 7.16 (s, 1H, 8-H), 6.97 (d, 1H, $^3$J=2.2 Hz, 3'-H), 6.27 (d, 1H, $^3$J=9.8 Hz, 4-H), 4.56 (t, 2H, $^3$J=5.8 Hz, 5-OCH$_2$CH$_2$CH$_2$OC$_6$H$_4$[3-NO$_2$]), 4.16 (t, 2H, $^3$J=5.6 Hz, 5-OCH$_2$CH$_2$CH$_2$ CH$_2$OC$_6$H$_4$[3-NO$_2$]), 2.12 (m, 4H, 5-OCH$_2$CH$_2$CH$_2$CH$_2$OC$_6$H$_4$[3-NO$_2$]).

Example 11

5-(4-{2",4"-Dinitrophenoxy}butoxy)psoralen (PAP 14)

4-(4-{2",4"-Dinitrophenoxy}butoxy)-7H-furo[3,2-g][1]benzopyran-7-on

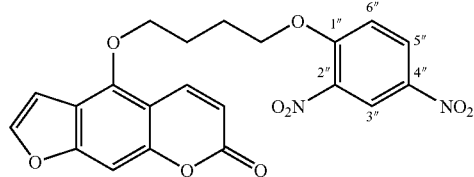

500 mg (1.708 mmol) of 5-(4-chlorobutoxy)psoralen, 512 mg (3.416 mmol) of sodium iodide and 629 mg (3.416 mmol) of 2,4-dinitrophenol were refluxed in 30 ml of anhydrous acetonitrile in the presence of an excess (3 g) of anhydrous potassium carbonate for 50 hours. The progress of the reaction was monitored by thin layer chromatography. After 50 hours the reaction mixture was concentrated under reduced pressure. The residue was cooled and diluted with water. The aqueous solution was then acidified with concentrated hydrochloric acid to pH 1. The slurry was stirred for 15-20 min and extracted with 3×50 ml of dichloromethane. The dichloromethane layer was extracted with 2×35 ml of 1% sodium hydroxide to separate the excess of 2,4-dinitrophenol. The dichloromethane layer was washed with 30 ml of 2% hydrochloric acid, dried over anhydrous sodium sulfate and concentrated. The solid residue obtained was dissolved in methanol-acetone mixture, treated with charcoal and re-crystallized from a methanol-acetone (80:20) mixture.

Yield: 82.4 mg (10.96%)

Melting point: 134.2° C.

$^1$H-NMR (500 MHz, CDCl$_3$): δ [ppm]=8.78 (d, 1H, $^4$J=2.8 Hz, 3"-H), 8.45 (dd, 1H, $^3$J=9.0 Hz, $^4$J=2.8 Hz, 5"-H), 8.15 (d, 1H, $^3$J=9.7 Hz, 3-H), 7.61 (d, 1H, $^3$J=2.0 Hz, 2'-H), 7.22 (d, 1H, $^3$J=9.5 Hz, 6"-H), 7.17 (s, 1H, 8-H), 6.98 (d, 1H, $^3$J=2.1 Hz, 3'-H), 6.29 (d, 1H, $^3$J=9.8 Hz, 4-H), 4.57 (t, 2H, $^3$J=5.3 Hz, 5-OCH$_2$CH$_2$CH$_2$CH$_2$OC$_6$H$_3$[2,4-(NO$_2$)$_2$]), 4.36 (t, 2H, $^3$J=5.1 Hz, 5-OCH$_2$CH$_2$CH$_2$CH$_2$OC$_6$H$_3$[2,4-(NO$_2$)$_2$]), 2.2 (m, 4H, 5-OCH$_2$CH$_2$CH$_2$CH$_2$OC$_6$H$_3$[2,4-(NO$_2$)$_2$]).

The following Examples 12-47 describe compounds that may be synthesized by methods that are similar to those described above with respect to Examples 1-11 and, thus, only physical data is being provided for the compounds of Examples 12-47.

Example 12

5-(4-[4-Methoxyphenoxy]butoxy)psoralen (AS67)

4-(4-[4-Methoxyphenoxy]butoxy)-7H-furo[3,2-g][1]benzopyran-7-on

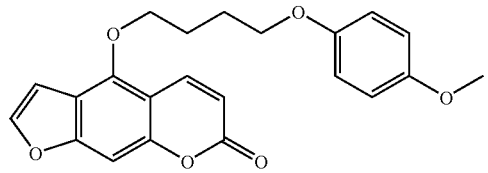

Melting point: 111.5° C.

Combustion analysis: C$_{22}$H$_{20}$O$_6$ (380.4)

| calculated: | C | 69.46 | H | 5.30 |
| found: | C | 69.52 | H | 5.39 |

$^1$H-NMR (DMSO-d$_6$, 300 MHz): δ/ppm (TMS)=1.91-1.99 (m, 4H, 5-O—CH$_2$(CH$_2$)$_2$CH$_2$—O—C$_6$H$_4$—OCH$_3$); 3.69 (s, 3H, —OCH$_3$); 4.00 (t, 2H, $^3$J=5.8 Hz, 5-O—CH$_2$(CH$_2$)$_2$CH$_2$—O—C$_6$H$_4$—OCH$_3$); 4.57 (t, 2H, $^3$J=5.7 Hz, 5-O—CH$_2$(CH$_2$)$_2$CH$_2$—O—C$_6$H$_4$—OCH$_3$); 6.30 (d, 1H, $^3$J=9.8 Hz, H-3); 6.81-6.87 (m, 4H, 5-O—CH$_2$(CH$_2$)$_2$CH$_2$—O—C$_6$H$_4$—OCH$_3$); 7.32-7.34 (m, 2H, H-8 and)H-4'); 8.03 (d, 1H, $^3$J=2.3 Hz, H-5'); 8.18 (d, 1H, $^3$J=9.8 Hz, H-4).

$^{13}$C-NMR (DMSO-d$_6$, 75 MHz): δ/ppm (TMS)=25.30 and 26.18 (5-O—CH$_2$(CH$_2$)$_2$CH$_2$—O—C$_6$H$_5$); 55.3 (—OCH$_3$); 67.49 and 72.29 (5-O—CH$_2$(CH$_2$)$_2$CH$_2$—O—C$_6$H$_5$); 93.17 (C-8); 105.61 (C-4'); 105.97 (C-4a); 112.27 (C-3); 112.91 (C-6); 114.54 and 115.29 (C-2", C-3", C-5" and C-6"); 139.42 (C-4); 145.88 (C-5'); 148.71 (C-5); 152.10 (C-8a); 152.47 and 153.25 (C-1" and C-4"); 157.62 (C-7); 160.06 (C-2).

IR (KBr): ν/cm$^{-1}$=3126, 2958, 1722, 1626, 1508, 1233, 1130.

MS (EI): m/z (%)=380 M$^+$ (14), 257 (8), 215 (7), 202 [M-C$_{11}$H$_{14}$O$_2$]$^+$ (5), 179 [C$_{11}$H$_{15}$O$_2$]$^+$ (69), 145 (6), 137 [CH$_3$—O—C$_6$H$_4$—CH$_2$]$^+$ (100), 109 (29), 107 [C$_6$H$_5$O—CH$_2$]$^+$ (18), 77 [C$_6$H$_5$]$^+$ (23), 55 [C$_4$H$_7$]$^+$ (61), 41 (15).

Example 13

5-(4-[3-Methoxyphenoxy]butoxyl)soralen (AS68)

4-(4-[3-Methoxyphenoxy]butoxy)-7H-furo[3,2-g][1]benzopyran-7-on

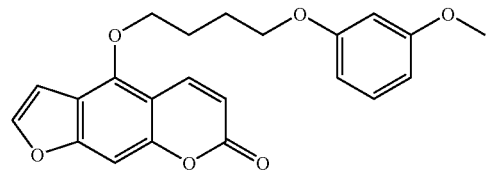

Melting point: 102.5° C.
Combustion analysis: C$_{22}$H$_{20}$O$_6$ (380.4)

| calculated: | C | 69.46 | H | 5.30 |
| found: | C | 68.89 | H | 5.38 |

$^1$H-NMR (DMSO-d$_6$, 300 MHz): δ/ppm (TMS)=1.91-1.99 (m, 4H 5-O—CH$_2$(CH$_2$)$_2$CH$_2$—O—C$_6$H$_4$—OCH$_3$); 3.71 (s, 3H, —OCH$_3$); 4.05 (t, 2H, $^3$J=5.4 Hz, 5-O—CH$_2$(CH$_2$)$_2$CH$_2$—O—C$_6$H$_4$—OCH$_3$); 4.58 (t, 2H, $^3$J=5.4 Hz, 5-O—CH$_2$(CH$_2$)$_2$CH$_2$—O—C$_6$H$_4$—OCH$_3$); 6.29 (d, 1H, $^3$J=9.8 Hz, H-3); 6.45-6.51 (m, 3H, H-2", H-4" and H-6"); 7.15 (t, 1H, $^3$J=8.14 Hz, H-5"); 7.33 (s, 2H, H-8 and H-4'); 8.02 (d, 1H, $^3$J=1.9 Hz, H-5"); 8.18 (d, 1H, $^3$J=9.8 Hz, H-4).

$^{13}$C-NMR (DMSO-d$_6$, 75 MHz): δ/ppm (TMS)=25.21 and 26.17 (5-O—CH$_2$(CH$_2$)$_2$CH$_2$—O—C$_6$H$_4$—OCH$_3$); 54.98 (—OCH$_3$); 67.04 and 72.24 (5-O—CH$_2$(CH$_2$)$_2$CH$_2$—O—C$_6$H$_4$—OCH$_3$); 93.15 (C-8); 100.62 (C-5"); 105.61 (C-4'); 105.95 (C-4a); 106.14 and 106.57 (C-4" and C-6"); 112.25 (C-3); 112.89 (C-6); 129.86 (C-2"); 139.42 (C-4); 145.86 (C-5'); 148.69 (C-5); 152.09 (C-8a); 157.61 (C-7); 159.73 and 160.44 (C-1" and C-3"); 160.05 (C-2).

IR (KBr): ν/cm$^{-1}$=3128, 2948, 1728, 1626, 1604, 1454, 1348, 1154.

MS (EI): m/z (%)=380 M$^+$ (14), 257 (8), 202 [M-C$_{11}$H$_{14}$O$_2$]$^+$ (5), 179 [C$_{11}$H$_{15}$O$_2$]$^+$ (84), 145 (6), 137 [CH$_3$—O—C$_6$H$_4$—CH$_2$]$^+$ (100), 109 (14), 107 [C$_6$H$_5$O—CH$_2$]$^+$ (32), 77 [C$_6$H$_5$]$^+$ (27), 55 [C$_4$H$_7$]$^+$ (63), 41 (12).

Example 14

5-(4-[3,5-Dimethoxyphenoxy]butoxy)psoralen (AS69)

4-(4-[3,5-Dimethoxyphenoxy]butoxy)-7H-furo[3,2-g][1]benzopyran-7-on

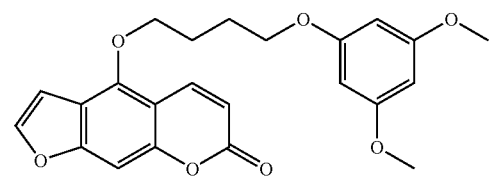

Melting point: 139° C.
Combustion analysis: C$_{23}$H$_{22}$O$_7$ (410.43)

| calculated: | C | 67.31 | H | 5.40 |
| found: | C | 66.92 | H | 5.60 |

$^1$H-NMR (DMSO-d$_6$, 300 MHz): δ/ppm (TMS)=1.93-1.97 (m, 4H, 5-O—CH$_2$(CH$_2$)$_2$CH$_2$—O—C$_6$H$_3$—(OCH$_3$)$_2$); 3.69 (s, 3H, —(OCH$_3$)$_2$); 4.05 (t, 2H, $^3$J=5.4 Hz, 5-O—CH$_2$(CH$_2$)$_2$CH$_2$—O—C$_6$H$_3$—(OCH$_3$)$_2$); 4.58 (t, 2H, $^3$J=5.4 Hz, 5-O—CH$_2$(CH$_2$)$_2$CH$_2$—O—C$_6$H$_3$—(OCH$_3$)$_2$); 6.07 (s, 3H, H-2", H-4" and H-6"); 6.31 (d, 1H, $^3$J=9.8 Hz, H-3); 7.34 (s, 2H, H-8 and H-4'); 8.03 (d, 1H, $^3$J=2.1 Hz, H-5'); 8.19 (d, 1H, $^3$J=9.8 Hz, H-4).

$^{13}$C-NMR (DMSO-d$_6$, 75 MHz): δ/ppm (TMS)=25.15 and 26.18 (5-O—CH$_2$(CH$_2$)$_2$CH$_2$—O—C$_6$H$_3$—(OCH$_3$)$_2$); 55.05 (—(OCH$_3$)$_2$); 67.10 and 72.20 (5-O—CH$_2$(CH$_2$)$_2$CH$_2$—O—C$_6$H$_3$—(OCH$_3$)$_2$); 92.79 (C-4"); 93.12 (C-8); 93.21 (C-2" and C-6"); 105.61 (C-4'); 105.94 (C-4-a); 112.22 (C-3); 112.86 (C-6); 139.40 (C-4); 145.84 (C-5'); 148.68 (C-5); 152.09 (C-8a); 157.61 (C-7); 160.05 (C-2); 160.34 (C-1"); 161.09 (C-3" and C-5").

IR (KBr): ν/cm$^{-1}$=3158, 2954, 1716, 1600, 1456, 1354, 1152.

MS (EI): m/z (%)=410 M$^+$ (12), 209 [C$_{12}$H$_{17}$O$_3$]$^+$ (100), 202 [M-C$_{12}$H$_{17}$O$_3$]$^+$ (5), 167 [(CH$_3$—O)$_2$—C$_6$H$_3$O—CH$_2$] (75), 137 [CH$_3$—O—C$_6$H$_4$—CH$_2$]$^+$ (34), 122 (15), 107 [C$_6$H$_5$O—CH$_2$]$^+$ (10), 77 [C$_6$H$_5$]$^+$ (11), 55 [C$_4$H$_7$]$^+$ (46), 41 (6).

Example 15

5-(4-[4-Nitrophenoxy]butoxy)psoralen (AS78)

4-(4-[4-Nitrophenoxy]butoxy)-7H-furo[3,2-g][1]benzopyran-7-on

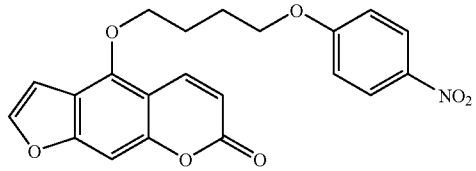

Melting point: 132° C.
Combustion analysis: $C_{21}H_{17}O_7$ (395.34)

| | | | | | |
|---|---|---|---|---|---|
| calculated: | C | 63.80 | H | 4.33 | N | 3.54 |
| found: | C | 63.79 | H | 4.46 | N | 3.60 |

$^1$H-NMR (DMSO-$d_6$, 300 MHz): δ/ppm (TMS)=1.99 (s, 4H, 5-O—CH$_2$(CH$_2$)$_2$CH$_2$—O—C$_6$H$_4$—NO$_2$); 4.05 (s, 2H, 5-O—CH$_2$(CH$_2$)$_2$$\overline{CH}_2$—O—C$_6$H$_4$—NO$_2$); 4.56 (s; 2H, 5-O—$\overline{CH}_2$(CH$_2$)$_2$CH$_2$—O—C$_6$H$_4$—NO$_2$); 6.27 (d, 1H, $^3$J=9.8 Hz, H-3); 7.10 (d, 2H, $^3$J=9.2 Hz, H-2" and H-6"); 7.28 (s, 1H, H-8); 7.30 (d, 1H, $^3$J=1.9 Hz, H-4'); 8.00 (d, 1H, $^3$J=2.1 Hz, H-5'); 8.15 (d, 1H, $^3$J=9.6 Hz, H-4); 8.16 (d, 2H, $^3$J=9.1 Hz, H-3" and H-5").

$^{13}$C-NMR (DMSO-$d_6$, 75 MHz): δ/ppm (TMS)=24.95 and 25.96 (5-O—CH$_2$(CH$_2$)$_2$CH$_2$—O—C$_6$H$_4$—NO$_2$); 68.25 and 72.04 (5-O—$\overline{CH}_2$(CH$_2$)$_2$CH$_2$—O—C$_6$H$_4$—NO$_2$); 93.07 (C-8); 105.56 ($\overline{C}$-4'); 105.84 (C-4a); 112.17 (C-3); 112.78 (C-6); 114.87 and 125.74 (C-2", C-3", C-5" and C-6"); 139.28 (C-4); 140.65 (C-4"); 145.80 (C-5'); 148.58 (C-5); 152.03 (C-8a); 157.57 (C-7); 159.99 (C-2); 163.80 (C-1").

IR (KBr): ν/cm$^{-1}$=2960, 2881, 1728, 1593, 1498, 1455, 1327, 1270.

MS (EI): m/z (%)=395 M$^+$(25), 202 [M-C$_{10}$H$_{14}$O$_3$N]$^+$ (30), 194 [C$_{10}$H$_{12}$O$_3$N]$^+$ (100), 174 [202-CO]$^+$ (26), 152 [O$_2$N—C$_6$H$_4$O—CH$_2$]$^+$ (82), 133 (17), 106 (17), 89 (13), 75 (12), 55 [C$_4$H$_7$]$^+$ (84), 41 (11).

Example 16

5-(4-[4-Chlorphenoxy]butoxy)psoralen (AS84)

4-(4-[4-Chlorphenoxy]butoxy)-7H-furo[3,2-g][1]benzopyran-7-on

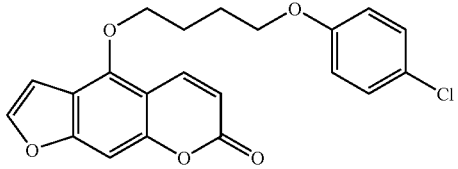

Melting point: 142.5° C.
Combustion analysis: $C_{21}H_{17}ClO_5$ (384.82)

| | | | | |
|---|---|---|---|---|
| calculated: | C | 65.55 | H | 4.45 |
| found: | C | 65.23 | H | 4.57 |

$^1$H-NMR (DMSO-$d_6$, 300 MHz): δ/ppm (TMS)=1.95-1.96 (m, 4H, 5-O—CH$_2$(CH$_2$)$_2$CH$_2$—O—C$_6$H$_4$—Cl); 4.05 (m, 2H, 5-O—CH$_2$(CH$_2$)$_2$$\overline{CH}_2$—O—C$_6$H$_4$—Cl); 4.55 (m, 2H, 5-O—$\overline{CH}_2$(CH$_2$)$_2$CH$_2$—O—C$_6$H$_4$—Cl); 6.28 (d, 1H, $^3$J=9.8 Hz, H-3); 6.93 (d, 2H, $^3$J=8.9 Hz, H-2" and H-6"); 7.29 (d, 2H, $^3$J=8.9 Hz, H-3" and H-5"); 7.31 (s, 2H, H-8 and H-4'); 8.01 (d, 1H, $^3$J=2.0 Hz, H-5'); 8.15 (d, 1H, $^3$J=9.8 Hz, H-4).

$^{13}$C-NMR (DMSO-$d_6$, 75 MHz): δ/ppm (TMS)=25.12 and 26.08 (5-O—CH$_2$(CH$_2$)$_2$CH$_2$—O—C$_6$H$_4$—Cl); 67.44 and 72.17 (5-O—$\overline{CH}_2$(CH$_2$)$_2$CH$_2$—O—C$_6$H$_4$—Cl); 93.10 (C-8); 105.59 ($\overline{C}$-4'); 105.89 (C-4a); 112.21 (C-3); 112.83 (C-6); 116.14 (C-2" and C-6"); 124.08 (C-4"); 129.13 (C-3" and C-5"); 139.34 (C-4); 145.83 (C-5'); 148.65 (C-5); 152.07 (C-8a); 157.32 (C-7); 157.60 (C-1"); 160.03 (C-2).

IR (KBr): ν/cm$^{-1}$=3090, 2929, 2882, 1718, 1618, 1577, 1491, 1346, 1246.

MS (EI): m/z (%)=384 M$^+$ (10), 202 [M-C$_{10}$H$_{14}$ClO]$^+$ (14), 183 [C$_{10}$H$_{12}$OCl]$^+$ (80), 174 [202-CO]$^+$ (11), 141 [C$_1$-C$_6$H$_4$O—CH$_2$]$^+$ (100), 113 (18), 111 (23), 89 (7), 77 [C$_6$H$_5$]$^+$ (9), 55 [C$_4$H$_7$]$^+$ (72), 41 (5).

Example 17

5-(4-[4-Phenoxyphenoxy]butoxy)psoralen (AS85)

4-(4-[4-Phenoxyphenoxy]butoxy)-7H-furo[3,2-g][1]benzopyran-7-on

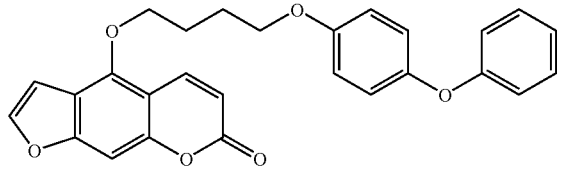

Melting point: 137° C.
Combustion analysis: $C_{27}H_{22}O_6$ (442.47)

| | | | | |
|---|---|---|---|---|
| calculated: | C | 73.29 | H | 5.01 |
| found: | C | 73.24 | H | 5.09 |

$^1$H-NMR (DMSO-$d_6$, 300 MHz): δ/ppm (TMS)=1.97 (s, 4H, 5-O—CH$_2$(CH$_2$)$_2$CH$_2$—O—C$_6$H$_4$—O—C$_6$H$_5$); 4.05 (s, 2H, 5-O—CH$_2$($\overline{CH}_2$)$_2$CH$_2$—O—C$_6$H$_4$—O—C$_6$H$_5$); 4.57 (s, 2H, 5-O—$\overline{CH}_2$(CH$_2$)$_2$CH$_2$—O—C$_6$H$_4$—O—C$_6$H$_5$); 6.29 (d, 1H, $^3$J=9.7 Hz, H-3); 6.89-6.96 (m, 6H, —O—C$_6$H$_4$—O—C$_6$H$_5$); 7.06 (t, 1H, H-4'''); 7.31-7.35 (m, 4H, H-8, $\overline{H}$-4' and —$\overline{O}$—C$_6$H$_4$—O—C$_6$$\underline{H}_5$); 8.02 (s, 1H, H-5'); 8.17 (d, 1H, $^3$J=9.8 Hz, $\overline{H}$-4).

$^{13}$C-NMR (DMSO-$d_6$, 75 MHz): δ/ppm (TMS)=25.28 and 26.14 (5-O—CH$_2$(CH$_2$)$_2$CH$_2$—O—C$_6$H$_4$—O—C$_6$H$_5$); 67.46 and 72.23 (5-O—$\overline{CH}_2$(CH$_2$)$_2$CH$_2$—O—C$_6$H$_4$—O—C$_6$H$_5$); 93.11 (C-8); 105.59 (C-4'); 105.91 (C-4a); 112.22 (C-3); 112.85 (C-6); 139.36 (C-4); 145.83 (C-5'); 148.67 (C-5); 152.07 (C-8a); 157.60 (C-7); 160.03 (C-2); 115.60, 117.23, 120.57, 122.49, 129.78, 149.32, 154.85 and 157.92 (—O—$\underline{C}_6$H$_4$—O—$\underline{C}_6$H$_5$).

IR (KBr): ν/cm$^{-1}$=3119, 2930, 1724, 1626, 1578, 1506, 1456, 1349, 1221.

MS (EI): m/z (%)=442 M$^+$ (25), 257 (16), 241 [C$_6$H$_5$—OC$_{10}$H$_{12}$O]$^+$ (100), 215 (12), 199 [C$_6$H$_5$—OC$_8$H$_8$O]$^+$ (100), 186 [C$_6$H$_5$—OC$_7$H$_5$O]$^+$ (100), 171 (12), 148 (38), 129 (13), 115 (17), 93 (10), 77 [C$_6$H$_5$]$^+$ (49), 55 [C$_4$H$_7$]$^+$ (70), 41 (7).

Example 18

5-(4-[4-Methylphenoxy]butoxy)psoralen (AS96)

4-(4-[4-Methylphenoxy]butoxy)-7H-furo[3,2-g][1]benzopyran-7-on

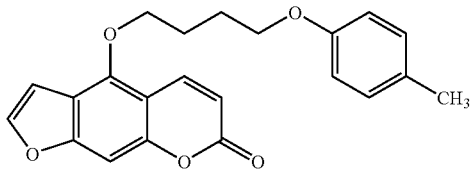

Melting point: 128° C.
Combustion analysis: C$_{22}$H$_{20}$O$_5$ (364.40)

| calculated: | C | 72.51 | H | 5.53 |
| --- | --- | --- | --- | --- |
| found: | C | 72.59 | H | 5.65 |

$^1$H-NMR (DMSO-d$_6$, 300 MHz): δ/ppm (TMS)=1.92-2.01 (m, 4H, 5-O—CH$_2$(CH$_2$)$_2$CH$_2$—O—C$_6$H$_4$—CH$_3$); 2.22 (s, 3H, —CH$_3$); 4.02 (t, 2H, $^3$J=5.7 Hz, 5-O—CH$_2$(CH$_2$)$_2$CH$_2$—O—C$_6$H$_4$—CH$_3$); 4.56 (t, 2H, $^3$J=5.6 Hz, 5-O—CH$_2$(CH$_2$)$_2$CH$_2$—O—C$_6$H$_4$—CH$_3$); 6.28 (d, 1H, $^3$J=9.8 Hz, H-3); 6.80 (d, 2H, $^3$J=8.5 Hz, H-3" and H-5"); 7.06 (d, 2H, $^3$J=8.4 Hz, H-2" and H-6"); 7.31 (s, 2H, H-8 and H-4'); 8.02 (d, 1H, $^3$J=2.1 Hz, H-5'); 8.15 (d, 1H, $^3$J=9.8 Hz, H-4).

$^{13}$C-NMR (DMSO-d$_6$, 75 MHz): δ/ppm (TMS)=19.97 (—CH$_3$); 25.25 and 26.16 (5-O—CH$_2$(CH$_2$)$_2$CH$_2$—O—C$_6$H$_4$—CH$_3$); 66.96 and 72.21 (5-O—CH$_2$(CH$_2$)$_2$CH$_2$—O—C$_6$H$_4$—CH$_3$); 93.06 (C-8); 105.56 (C-4'); 105.87 (C-4a); 112.16 (C-3); 112.79 (C-6); 114.19 (C-3" and C-5"); 128.95 (C-4"); 129.69 (C-2" and C-6"); 139.32 (C-4); 145.78 (C-5'); 148.63 (C-5); 152.05 (C-8a); 156.33 (C-1"); 157.57 (C-7); 160.01 (C-2).

IR (KBr): ν/cm$^{-1}$=3091, 2915, 1717, 1619, 1576, 1509, 1456, 1346, 1244.

MS (EI): m/z (%)=364 M$^+$ (10), 202 [M-C$_{11}$H$_{13}$O]$^+$ (5), 163 [C$_{11}$H$_{15}$O]$^+$ (87), 121 [CH$_3$—C$_6$H$_4$O—CH$_2$]$^+$ (100), 91 [C$_7$H$_7$]$^+$ (33), 65 (9), 55 [C$_4$H$_7$]$^+$ (35), 41 (4).

Example 19

5(4-[4-Ethylphenoxy]butoxy)psoralen (AS106)

4-(4-[4-Ethylphenoxy]butoxy)-7H-furo[3,2-g][1]benzopyran-7-on

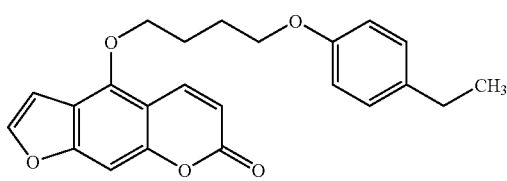

Melting point: 104° C.
Combustion analysis: C$_{23}$H$_{22}$O$_5$ (378.43)

| calculated: | C | 73.00 | H | 5.86 |
| --- | --- | --- | --- | --- |
| found: | C | 71.74 | H | 5.89 |

$^1$H-NMR (DMSO-d$_6$, 300 MHz): δ/ppm (TMS)=1.14 (t, 3H, $^3$J=7.6 Hz, —CH$_2$CH$_3$); 1.95-1.99 (m, 4H, 5-O—CH$_2$(CH$_2$)$_2$CH$_2$—O—C$_6$H$_4$—CH$_2$CH$_3$); 2.52 (q, 2H, $^3$J=7.6 Hz —CH$_2$CH$_3$); 4.03 (t, 2H, $^3$J=5.7 Hz, 5-O—CH$_2$(CH$_2$)$_2$CH$_2$—O—C$_6$H$_4$—CH$_2$CH$_3$); 4.57 (t, 2H, $^3$J=5.7 Hz, 5-O—CH$_2$(CH$_2$)$_2$CH$_2$—O—C$_6$H$_4$—CH$_2$CH$_3$); 6.28 (d, 1H, $^3$J=9.8 Hz, H-3); 6.82 (d, 2H, $^3$J=8.6 Hz, H-3" and H-5"); 7.09 (d, 2H, $^3$J=8.5 Hz, H-2" and H-6"); 7.33 (s, 2H, H-8 and H-4'); 8.02 (d, 1H, $^3$J=2.3 Hz, H-5'); 8.18 (d, 1H, $^3$J=9.8 Hz, H-4).

$^{13}$C-NMR (DMSO-d$_6$, 75 MHz): δ/ppm (TMS)=15.82 (—CH$_3$); 25.27 and 26.17 (5-O—CH$_2$(CH$_2$)$_2$CH$_2$—O—C$_6$H$_4$—C$_2$H$_5$); 27.20 (—CH$_2$CH$_3$); 66.98 and 72.26 (5-O—CH$_2$(CH$_2$)$_2$CH$_2$—O—C$_6$H$_4$—C$_2$H$_5$); 93.13 (C-8); 105.59 (C-4'); 105.93 (C-4a); 112.22 (C-3); 112.87 (C-6); 114.22 (C-3" and C-5"); 128.51 (C-4"); 135.55 (C-2" and C-6"); 139.38 (C-4); 145.84 (C-5'); 148.68 (C-5); 152.08 (C-8a); 156.51 (C-1"); 157.60 (C-7); 160.03 (C-2).

IR (KBr): ν/cm$^{-1}$=3088, 2928, 1720, 1618, 1576, 1512, 1456, 1346, 1250.

MS (EI): m/z (%)=378 M$^+$ (9), 202 [M-C$_{12}$H$_{15}$O]$^+$ (5), 177 [CH$_2$H$_{17}$O]$^+$ (92), 135 [CH$_3$—CH$_2$C$_6$H$_4$O—CH$_2$]$^+$ (100), 107 [C$_8$H$_{11}$]$^+$ (26), 79 (22), 55 [C$_4$H$_7$]$^+$ (44).

Example 20

5-(4-[4-Fluorphenoxy]butoxy)psoralen (AS111)

4-(4-[4-Fluorphenoxy]butoxy)-7H-furo[3,2-g][1]benzopyran-7-on

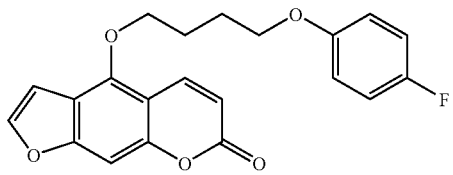

Melting point: 121° C.
Combustion analysis: C$_{21}$H$_{17}$FO$_5$ (368.37)

| calculated: | C | 68.47 | H | 4.65 |
| --- | --- | --- | --- | --- |
| found: | C | 68.15 | H | 4.65 |

$^1$H-NMR (DMSO-d$_6$, 300 MHz): δ/ppm (TMS)=1.94-1.96 (m, 4H, 5-O—CH$_2$(CH$_2$)$_2$CH$_2$—O—C$_6$H$_4$—F); 4.01-4.05 (m, 2H, 5-O—CH$_2$(CH$_2$)$_2$CH$_2$—O—C$_6$H$_4$—F); 4.53-4.55 (m, 2H, 5-O—CH$_2$(CH$_2$)$_2$CH$_2$—O—C$_6$H$_4$—F); 6.27 (d, 1H, $^3$J=9.8 Hz, H-3); 6.89-6.94 (m, 2H, 5-O—CH$_2$(CH$_2$)$_2$CH$_2$—O—C$_6$H$_4$—F); 7.30 (s, 2H, H-4' and H-8); 8.01 (d, 1H, $^3$J=2.0 Hz, H-5'); 8.14 (d, 1H, $^3$J=9.8 Hz, H-4).

¹³C-NMR (DMSO-d₆, 75 MHz): δ/ppm (TMS)=25.20 and 26.10 (5-O—CH₂(CH₂)₂CH₂—O—C₆H₄—F); 67.60 and 72.17 (5-O—CH₂(CH₂)₂CH₂—O—C₆H₄—F); 93.07 (C-8); 105.56 (C-4'); 105.87 (C-4a); 112.18 (C-3); 112.80 (C-6); 115.53, 115.63 and 115.83 (C-2", C-3", C-5" and C-6"); 139.32 (C-4); 145.80 (C-5'); 148.63 (C-5); 152.05 (C-8a); 154.79 (C-5"); 157.58 (C-7); 157.91 (C-1"); 160.02 (C-2).

IR (KBr): ν/cm⁻¹=2947, 1722, 1625, 1503, 1457, 1346, 1203.

MS (EI): m/z (%)=368 M⁺ (11), 202 [M-C₁₀H₁₄FO]⁺ (11), 174 [202-CO]⁺ (11), 167 [C₁₀H₁₂OF] (83), 125 [F—C₆H₄O—CH₂]⁺ (100), 95 (23), 89 (5), 55 [C₄H₇]⁺ (46), 41 (3).

Example 21

5-(4-[3-Trifluormethylphenoxy]butoxy)psoralen (AS118)

4-(4-[3-Trifluormethylphenoxy]butoxy)-7H-furo[3,2-g][1]benzopyran-7-on

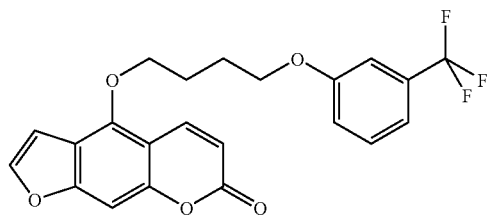

Melting point: 118° C.
Combustion analysis: $C_{22}H_{17}F_3O_5$ (418.37)

| calculated: | C | 63.16 | H | 4.10 |
| --- | --- | --- | --- | --- |
| found: | C | 63.19 | H | 4.09 |

¹H-NMR (DMSO-d₆, 300 MHz): δ/ppm (TMS)=1.98 (s, 4H, 5-O—CH₂(CH₂)₂CH₂—O—C₆H₄—CF₃); 4.15 (s, 2H, 5-O—CH₂(CH₂)₂CH₂—O—C₆H₄—CF₃); 4.57 (s, 2H, 5-O—CH₂(CH₂)₂CH₂—O—C₆H₄—CF₃); 6.26 (d, 1H, ³J=9.8 Hz, H-3); 7.18-7.32 (m, 5H, H-2", H-4", H-6", H-8 and H-4'); 7.49 (t, 1H, ³J=7.93 Hz, H-5"); 8.01 (d, 1H, ³J=2.3 Hz, H-5'); 8.15 (d, 1H, ³J=9.8 Hz, H-4).

¹³C-NMR (DMSO-d₆, 75 MHz): δ/ppm (TMS)=25.05 and 26.04 (5-O—CH₂(CH₂)₂CH₂—O—C₆H₄—CF₃); 67.56 and 72.10 (5-O—CH₂(CH₂)₂CH₂—O—C₆H₄—CF₃); 93.06 (C-8); 105.58 (C-4'); 105.84 (C-4a); 110.78, 110.84, 116.86, 116.91 and 130.58 (5-O—CH₂(CH₂)₂CH₂—O—C₆H₄—CF₃); 112.16 (C-3); 112.78 (C-6); 118.64 (—CF₃); 139.30 (C-4); 145.78 (C-5'); 148.63 (C-5); 152.06 (C-8a); 157.59 (C-7); 158.76 (C-1"); 160.00 (C-2).

IR (KBr): ν/cm⁻¹=2960, 1724, 1626, 1590, 1456, 1348, 1328, 1130.

MS (EI): m/z (%)=418 M⁺ (14), 217 (79), 202 [M-C₁₁H₁₄O₂]⁺ (19), 175 [C₁₂H₁₅O]⁺ (100), 145 (37), 127 (7), 109 (14), 89 (6), 55 [C₄H₇]⁺ (75), 41 (4).

Example 22

5-(4-[1-Naphthyloxy]butoxy)psoralen (AS119)

4-(4-[1-Naphthyloxy]butoxy)-7H-furo[3,2-g][1]benzopyran-7-on

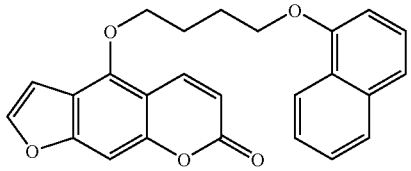

Melting point: 119° C.
Combustion analysis: $C_5H_{20}O_5$ (400.44)

| calculated: | C | 74.99 | H | 5.30 |
| --- | --- | --- | --- | --- |
| found: | C | 74.91 | H | 5.16 |

¹H-NMR (DMSO-d₆, 300 MHz): δ/ppm (TMS)=2.10 (s, 4H, 5-O—CH₂(CH₂)₂CH₂—O—C₁₀H₇); 4.25 (s, 2H, 5-O—CH₂(CH₂)₂CH₂—O—C₁₀H₇); 4.63 (s, 2H, 5-O—CH₂(CH₂)₂CH₂—O—C₁₀H₇); 6.22 (d, 1H, ³J=9.8 Hz, H-3); 6.95 (d, 1H, ³J=7.2 Hz, 5-O—CH₂(CH₂)₂CH₂—O—C₁₀H₇); 7.30-7.52 (m, 6H, H-8, H-4' and 5-O—CH₂(CH₂)₂CH₂—O—C₁₀H₇); 7.84 (d, 1H, ³J=8.1 Hz, 5-O—CH₂(CH₂)₂CH₂—O—C₁₀H₇); 8.00 (d, 1H, ³J=2.2 Hz, H-5'); 8.08 (d, 1H, ³J=8.3, 5-O—CH₂(CH₂)₂CH₂—O—C₁₀H₇); Hz 8.16 (d, 1H, ³J=9.8 Hz, H-4).

¹³C-NMR (DMSO-d₆, 75 MHz): δ/ppm (TMS)=25.28 and 26.39 (5-O—CH₂(CH₂)₂CH₂—O—C₁₀H₇); 67.37 and 72.20 (5-O—CH₂(CH₂)₂CH₂—O—C₁₀H₇); 93.06 (C-8); 105.07, 119.73, 121.28, 124.86, 125.03, 126.13, 126.29, 127.36 and 133.95 (5-O—CH₂(CH₂)₂CH₂—O—C₁₀H₇); 105.61 (C-4'); 105.87 (C-4a); 112.14 (C-3); 112.78 (C-6); 139.34 (C-4); 145.79 (C-5'); 148.61 (C-5); 152.06 (C-8a); 157.60 (C-7); 153.88 (C-1"); 160.02 (C-2).

IR (KBr): ν/cm⁻¹=2956, 1728, 1624, 1578, 1456, 1344, 1268, 1128.

MS (EI): m/z (%)=400 M⁺ (35), 257 (42), 215 (26), 199 [C₁₄H₁₅O]⁺ (100), 157 [C₁₁H₉O]⁺ (96), 127 (40), 89 (12), 55 [C₄H₇]⁺ (97).

Example 23

5-(4-[2-Naphthyloxy]butoxy)psoralen (AS120)

4-(4-[2-Naphthyloxy]butoxy)-7H-furo[3,2-g][1]benzopyran-7-on

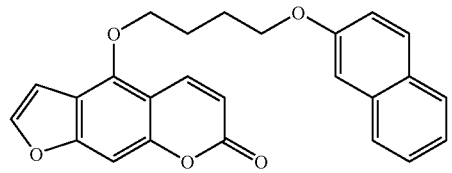

Melting point: 122° C.
Combustion analysis: $C_{25}H_{20}O_5$ (400.44)

| calculated: | C | 74.99 | H | 5.30 |
| --- | --- | --- | --- | --- |
| found: | C | 75.28 | H | 5.22 |

$^1$H-NMR (DMSO-$d_6$, 300 MHz): δ/ppm (TMS)=2.04 (s, 4H, 5-O—CH$_2$(CH$_2$)$_2$CH$_2$—O—C$_{10}$H$_7$); 4.21 (s, 2H, 5-O—CH$_2$(CH$_2$)$_2$CH$_2$—O—C$_{10}$H$_7$); 4.60 (s, 2H, 5-O—CH$_2$(CH$_2$)$_2$CH$_2$—O—C$_{10}$H$_7$); 6.22 (d, 1H, $^3$J=9.8 Hz, H-3); 7.14 (dd, 1H, $^3$J=8.9 Hz, $^5$J=2.4 Hz, H-3"); 7.27-7.36 (m, 4H, H-8, H-4' and 5-O—CH$_2$(CH$_2$)$_2$CH$_2$—O—C$_{10}$H$_7$); 7.45 (t, 1H, $^3$J=7.5 Hz, 5-O—CH$_2$(CH$_2$)$_2$CH$_2$—O—C$_{10}$H$_7$); 7.76-7.83 (m, 3H, 5-O—CH$_2$(CH$_2$)$_2$CH$_2$—O—C$_{10}$H$_7$); 8.00 (d, 1H, $^3$J=2.3 Hz, H-5'); Hz 8.17 (d, 1H, $^3$J=9.8 Hz, H-4).

$^{13}$C-NMR (DMSO-$d_6$, 75 MHz): δ/ppm (TMS)=25.21 and 26.22 (5-O—CH$_2$(CH$_2$)$_2$CH$_2$—O—C$_{10}$H$_7$); 67.16 and 72.26 (5-O—CH$_2$(CH$_2$)$_2$CH$_2$—O—C$_{10}$H$_7$); 93.13 (C-8); 105.65 (C-4'); 105.92 (C-4a); 106.74, 118.64, 123.47, 126.32, 126.58, 127.45, 128.41, 129.22 and 134.27 (5-O—CH$_2$(CH$_2$)$_2$CH$_2$—O—C$_{10}$H$_7$); 112.21 (C-3); 112.86 (C-6); 139.38 (C-4); 145.86 (C-5'); 148.71 (C-5); 152.11 (C-8a); 156.38 (C-1"); 157.64 (C-7); 160.04 (C-2).

IR (KBr): ν/cm$^{-1}$=1732, 1626, 1600, 1460, 1354, 1260.

MS (EI): m/z (%)=400 M$^+$ (20), 257 (5), 215 (5), 199 [C$_{14}$H$_{15}$O]$^+$ (97), 157 [C$_{11}$H$_{9O}$]$^+$ (100), 127 (49), 89 (8), 55 [C$_4$H$_7$]$^+$ (72).

Example 24

5-[3-(4-Methoxyphenoxy)propoxy]psoralen (AS79)

4-[3-(4-Methoxyphenoxy)propoxy]-7H-furo[3,2-g][1]benzopyran-7-on

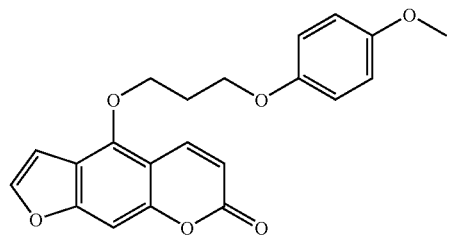

Melting point: 139.5° C.
Combustion analysis: C$_{21}$H$_{18}$O$_6$ (366.37)

| calculated: | C | 68.85 | H | 4.95 |
| --- | --- | --- | --- | --- |
| found: | C | 68.56 | H | 5.07 |

$^1$H-NMR (DMSO-$d_6$, 300 MHz): δ/ppm (TMS)=2.24 (t, 2H, $^3$J=6.0 Hz, 5-O—CH$_2$CH$_2$CH$_2$—O—C$_6$H$_4$—OCH$_3$); 3.68 (s, 3H, —OCH$_3$); 4.15 (t, 2H, $^3$J=6.0 Hz, 5-O—CH$_2$CH$_2$CH$_2$—O—C$_6$H$_4$—OCH$_3$); 4.63 (t, 2H, $^3$J=5.9 Hz, 5-O—CH$_2$CH$_2$CH$_2$—O—C$_6$H$_4$—OCH$_3$); 6.28 (d, 1H, $^3$J=9.8 Hz, H-3); 6.82-6.90 (m, 4H, 5-O—CH$_2$CH$_2$CH$_2$—O—C$_6$H$_4$—OCH$_3$); 7.31-7.32 (m, 2H, H-8 and H-4'); 8.02 (s, 1H, H-5'); 8.20 (d, 1H, $^3$J=9.8 Hz, H-4).

$^{13}$C-NMR (DMSO-$d_6$, 75 MHz): δ/ppm (TMS)=29.30 (5-O—CH$_2$CH$_2$CH$_2$—O—C$_6$H$_4$OCH$_3$); 55.29 (—OCH$_3$); 64.55 and 69.52 (5-O—CH$_2$CH$_2$CH$_2$—O—C$_6$H$_4$OCH$_3$); 93.33 (C-8); 105.38 (C-4'); 106.08 (C-4a); 112.30 (C-3); 113.02 (C-6); 114.56 and 115.35 (C-2", C-3", C-5" and C-6"); 139.42 (C-4); 145.96 (C-5'); 148.54 (C-5); 152.05 (C-8a); 152.40 and 153.37 (C-1" and C-4"); 157.55 (C-7); 160.02 (C-2).

IR (KBr): ν/cm$^{-1}$=3125, 2952, 2828, 1721, 1622, 1508, 1456, 1352, 1233, 1129.

MS (EI): m/z (%)=366 M$^+$ (32), 243 (18), 215 (17), 202 [C$_{11}$H$_6$O$_4$]$^+$ (18), 165 [C$_{10}$H$_{13}$O$_2$]$^+$ (100), 145 (10), 137 [CH$_3$—O—C$_6$H$_4$O—CH$_2$]$^+$ (94), 109 (30), 92 (17), 77 [C$_6$H$_5$]$^+$ (35), 51 (14), 44 (40).

Example 25

5-[3-(3-Methoxyphenoxy)propoxy]psoralen (AS64)

4-[3-(3-Methoxyphenoxy)propoxy]-7H-furo[3,2-g][1]benzopyran-7-on

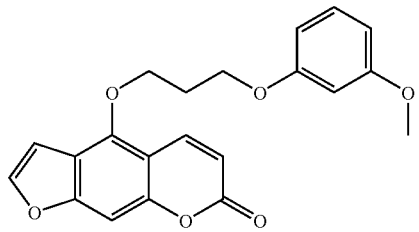

Melting point: 154.5° C.
Combustion analysis: O$_{21}$H$_{18}$O$_6$ (366.37)

| calculated: | C | 68.85 | H | 4.95 |
| --- | --- | --- | --- | --- |
| found: | C | 68.57 | H | 5.05 |

$^1$H-NMR (DMSO-$d_6$, 300 MHz): δ/ppm (TMS)=2.27 (quint, 2H, $^3$J=6.1 Hz, 5-O—CH$_2$CH$_2$CH$_2$—O—C$_6$H$_4$—OCH$_3$); 3.72 (s, 6H, —OCH$_3$); 4.22 (t, 2H, $^3$J=6.2 Hz, 5-O—CH$_2$CH$_2$CH$_2$—O—C$_6$H$_4$—OCH$_3$); 4.66 (t, 2H, $^3$J=6.0 Hz, 5-O—CH$_2$CH$_2$CH$_2$—O—C$_6$H$_4$—OCH$_3$); 6.30 (d, 1H, $^3$J=9.8 Hz, H-3); 6.50-6.55 (m, 3H, H-2", H-4" and H-6"); 7.17 (t, 1H, $^3$J=8.5 Hz, H-5"); 7.33 (d, 1H, $^3$J=2.2 Hz, H-4'); 7.36 (s, 1H, H-8); 8.04 (d, 1H, $^3$J=2.2 Hz, H-5'); 8.24 (d, 1H, $^3$J=9.8 Hz, H-4).

$^{13}$C-NMR (DMSO-$d_6$, 75 MHz): δ/ppm (TMS)=29.20 (5-O—CH$_2$CH$_2$CH$_2$—O—C$_6$H$_4$—OCH$_3$); 55.01 (—OCH$_3$); 64.10 and 69.49 (5-O—CH$_2$CH$_2$CH$_2$—O—C$_6$H$_4$—OCH$_3$); 93.35 (C-8); 100.70 (C-5"); 105.41 (C-4'); 106.09 (C-4a); 106.30 and 106.61 (C-4" and C-6"); 112.31 (C-3); 113.01 (C-6); 129.91 (C-2"); 139.49 (C-4); 145.99 (C-5'); 148.55 (C-5); 152.06 (C-8a); 157.56 (C-7); 159.65 and 160.46 (C-1" and C-3"); 160.02 (C-2).

IR (KBr): λ/cm$^{-1}$=3125, 2956, 1724, 1618, 1455, 1352, 1270, 1175.

MS (EI): m/z (%)=366 M$^+$ (16), 202 [C$_{11}$H$_6$O$_4$]$^+$ (7), 165 [C$_{10}$H$_{13}$O$_2$]$^+$ (100), 137 [CH$_3$—O—C$_6$H$_4$—CH$_2$]$^+$ (80), 124 (8), 107 [C$_6$H$_5$O—CH$_2$]$^+$ (30), 92 (16), 77 [C$_6$H$_5$]$^+$ (32), 64 (8), 51 (10), 41 [C$_3$H$_5$]$^+$ (24).

Example 26

5-[3-(3,5-Dimethoxyphenoxy)porpoxy]psoralen (AS104)

4-[3-(3,5-Dimethoxyphenoxy)propoxy]-7H-furo[3,2-g][1]benzopyran-7-on

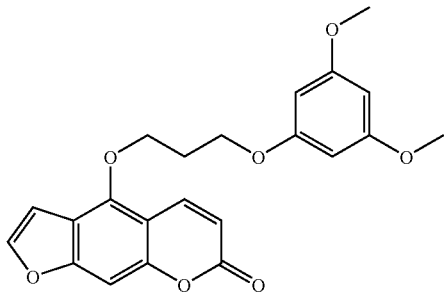

Melting point: 154.5° C.
Combustion analysis: $C_{22}H_{20}O_7$ (396.40)

| calculated: | C | 66.66 | H | 5.09 |
|---|---|---|---|---|
| found: | C | 66.43 | H | 5.06 |

$^1$H-NMR (DMSO-$d_6$, 300 MHz): δ/ppm (TMS)=1.97 (t, 2H, $^3$J=5.7 Hz, 5-O—CH$_2$CH$_2$CH$_2$—O—C$_6$H$_3$—(OCH$_3$)$_2$); 3.70 (s, 3H, —(OCH$_3$)$_2$); 4.20 (t, 2H, $^3$J=5.8 Hz, 5-O—CH$_2$CH$_2$CH$_2$—O—C$_6$H$_3$—(OCH$_3$)$_2$); 4.65 (t, 2H, $^3$J=5.6 Hz, 5-O—CH$_2$CH$_2$CH$_2$—O—C$_6$H$_3$—(OCH$_3$)$_2$); 6.09-6.12 (m, 3H, H-2", H-4" and H-6"); 6.29 (d, 1H, $^3$J=9.8 Hz, H-3); 7.33 (s, 2H, H-8 and H-4'); 8.03 (s, 1H, H-5'); 8.24 (d, 1H, $^3$J=9.8 Hz, H-4).

$^{13}$C-NMR (DMSO-$d_6$, 75 MHz): δ/ppm (TMS)=29.17 (5-O—CH$_2$CH$_2$CH$_2$—O—C$_6$H$_3$—(OCH$_3$)$_2$); 55.07 (—(OCH$_3$)$_2$); 64.16 and 69.44 (5-O—CH$_2$CH$_2$CH$_2$—O—C$_6$H$_3$—(OCH$_3$)$_2$); 92.92 (C-8); 93.29 (C-2", C-4" and C-6"); 105.40 (C-4'); 106.05 (C-4a); 112.26 (C-3); 112.96 (C-6); 139.48 (C-4); 145.95 (C-5'); 148.53 (C-5); 152.05 (C-8a); 157.56 (C-7); 160.01 (C-2); 160.27 (C-1"); 161.11 (C-3" and C-5").

IR (KBr): ν/cm$^{-1}$=3082, 2939, 1727, 1605, 1456, 1387, 1156.

MS (EI): m/z (%)=396 M$^+$ (12), 202 [C$_{11}$H$_6$O$_4$]$^+$ (3), 195 [C$_{11}$H$_{15}$O$_{31}$]$^+$ (100), 167 [(CH$_3$—O)$_2$—C$_6$H$_3$O—CH$_2$]$^+$ (53), 154 (11), 137 [CH$_3$—O—C$_6$H$_4$O—CH$_2$]$^+$ (19), 122 (13), 107 [C$_6$H$_5$O—CH$_2$]$^+$ (7), 77 [C$_6$H$_5$]$^+$ (9), 51 (6), 41 [C$_3$H$_5$]$^+$ (6).

Example 27

5-[3-(4-Nitrophenoxy)propoxy]psoralen (AS92)

4-[3-(4-Nitrophenoxy)propoxy]-7H-furo[3,2-g][1]benzopyran-7-on

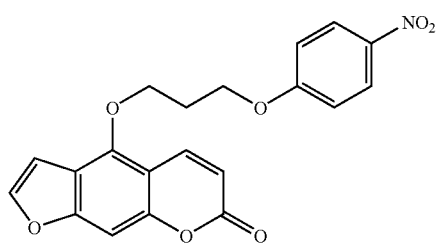

Melting point: 179° C.
Combustion analysis: $C_{20}H_{15}NO_7$ (381.35)

| Calculated: | C | 62.99 | H | 3.96 | N | 3.67 |
|---|---|---|---|---|---|---|
| Found: | | | | | | |

$^1$H-NMR (DMSO-$d_6$, 300 MHz): δ/ppm (TMS)=2.32-2.36 (m, 2H, 5-O—CH$_2$CH$_2$CH$_2$—O—C$_6$H$_4$—NO$_2$); 4.40 (t, 2H, $^3$J=6.1 Hz, 5-O—CH$_2$CH$_2$CH$_2$—O—C$_6$H$_4$—NO$_2$); 4.68 (t, 2H, $^3$J=5.7 Hz, 5-O—CH$_2$CH$_2$CH$_2$—O—C$_6$H$_4$—NO$_2$); 6.31 (d, 1H, $^3$J=9.8 Hz, H-3); 7.18 (d, 2H, $^3$J=9.0 Hz, 5-O—CH$_2$CH$_2$CH$_2$—O—C$_6$H$_4$—NO$_2$); 7.34 (s, 2H, H-8 and H-4'); 8.04 (s, 1H, H-5'); 8.19-8.27 (m, 3H, H-4 and 5-O—CH$_2$CH$_2$CH$_2$—O—C$_6$H$_4$—NO$_2$).

$^{13}$C-NMR (DMSO-$d_6$, 75 MHz): δ/ppm (TMS)=28.93 (5-O—CH$_2$CH$_2$CH$_2$—O—C$_6$H$_4$—NO$_2$); 65.44 and 69.29 (5-O—CH$_2$CH$_2$CH$_2$—O—C$_6$H$_4$—NO$_2$); 93.36 (C-8); 105.40 (C-4'); 106.05 (C-4-a); 112.33 (C-3); 112.96 (C-6); 114.99 (C-2" and C-6"); 125.82 (C-3" and C-5"); 139.48 (C-4); 140.80 (C-4"); 146.00 (C-5'); 148.46 (C-5); 152.04 (C-8a); 157.55 (C-7); 160.01 (C-2); 163.72 (C-1").

IR (KBr): ν/cm$^{-1}$=3153, 2945, 2358, 1716, 1520, 1352, 1266, 1132.

MS (EI): m/z (%)=381 M$^+$ (49), 202 [C$_{11}$H$_6$O$_4$]$^+$ (100), 174 [202-CO]$^+$ (31), 152 [O$_2$N—C$_6$H$_4$O—CH$_2$]$^+$ (52), 119 (35), 106 (16), 75 (23), 51 (26), 41 [C$_3$H$_5$]$^+$ (55).

Example 28

5-[3-(4-Chlorphenoxy)propoxy]psoralen (AS132)

4-[3-(4-Chlorphenoxy)propoxy]-7H-furo[3,2-g][1]benzopyran-7-on

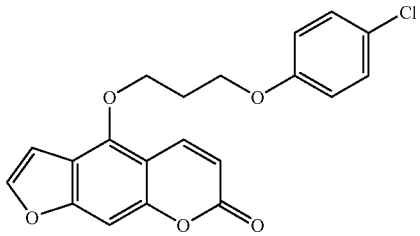

Melting point: 137.5° C.
Combustion analysis: $C_{20}H_{15}ClO_5$ (370.79)

| calculated.: | C | 64.79 | H | 4.08 |
|---|---|---|---|---|
| found.: | C | 64.47 | H | 4.18 |

$^1$H-NMR (DMSO-$d_6$, 300 MHz): δ/ppm (TMS)=2.28 (quint, 2H, $^3$J=6.1 Hz, 5-O—CH$_2$CH$_2$CH$_2$—O—C$_6$H$_4$—Cl); 4.23 (t, 2H, $^3$J=6.2 Hz, 5-O—CH$_2$CH$_2$CH$_2$—O—C$_6$H$_4$—Cl); 4.65 (t, 2H, $^3$J=6.1 Hz, 5-O—CH$_2$CH$_2$CH$_2$—O—C$_6$H$_4$—Cl); 6.30 (d, 1H, $^3$J=9.8 Hz, H-3); 6.96-7.02 (m, 2H, 5-O—CH$_2$CH$_2$CH$_2$—O—C$_6$H$_4$—Cl); 7.29-7.34 (m, 4H, H-8, H-4' and 5-O—CH$_2$CH$_2$CH$_2$—O—C$_6$H$_4$—Cl); 8.03 (d, 1H, $^3$J=2.4 Hz, H-5'); 8.23 (d, 1H, $^3$J=9.7 Hz, H-4).

$^{13}$C-NMR (DMSO-d$_6$, 75 MHz): δ/ppm (TMS)=29.09 (5-O—CH$_2$CH$_2$CH$_2$—O—C$_6$H$_4$—Cl); 64.54 and 69.40 (5-O—CH$_2$CH$_2$CH$_2$—O—C$_6$H$_4$—Cl); 93.33 (C-8); 105.37 (C-4'); 106.05 (C-4a); 112.30 (C-3); 112.98 (C-6); 116.17 (0-2" and C-6"); 124.23 (C-4"); 129.16 (C-3" and C-5"); 139.44 (C-4); 145.96 (C-5'); 148.49 (C-5); 152.03 (C-8a); 157.24 (C-7); 157.54 (C-1"); 159.99 (C-2).

IR (KBr): ν/cm$^{-1}$=3129, 2953, 1716, 1621, 1578, 1492, 1353, 1251.

MS (EI): m/z (%)=370 M$^+$ (38), 202 [C$_{11}$H$_6$O$_4$]$^+$ (88), 169 [C$_9$H$_{10}$OCl]$^+$ (69), 141 [C$_1$-C$_6$H$_4$O—CH$_2$]$^+$ (100), 111 (39), 75 (23), 41 [C$_3$H$_5$]$^+$ (88).

Example 29

5-[3-(4-Phenoxyphenoxy)propoxy]psoralen (AS122)

4-[3-(4-Phenoxyphenoxy)propoxy]-7H-furo[3,2-g][1]benzopyran-7-on

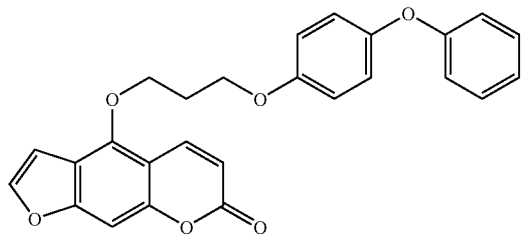

Melting point: 133.5° C.
Combustion analysis: C$_{26}$H$_{20}$O$_6$ (428.45)

| calculated: | C | 72.89 | H | 4.71 |
| found: | C | 73.23 | H | 4.81 |

$^1$H-NMR (DMSO-d$_6$, 300 MHz): δ/ppm (TMS)=2.29 (quint, 2H, $^3$J=6.0 Hz, 5-O—CH$_2$CH$_2$CH$_2$—O—C$_6$H$_4$—O—C$_6$H$_5$); 4.23 (t, 2H, $^3$J=6.1 Hz, 5-O—CH$_2$CH$_2$CH$_2$—O—C$_6$H$_4$—O—C$_6$H$_5$); 4.67 (t, 2H, $^3$J=6.0 Hz, 5-O—CH$_2$CH$_2$CH$_2$—O—C$_6$H$_4$—O—C$_6$H$_5$); 6.30 (d, 1H, $^3$J=9.7 Hz, H-3); 6.91 (d, 2H, $^3$J=8.1 Hz, —O—C$_6$H$_4$—O—C$_6$H$_5$); 6.96-7.02 (m, 4H, 5-O—CH$_2$CH$_2$CH$_2$—O—C$_6$H$_4$—O—C$_6$H$_5$); 7.07 (t, 1H, $^3$J=7.3 Hz, H-4'''); 7.32-7.37 (m, 4H, H-8, H-4' and —O—C$_6$H$_4$—O—C$_6$H$_5$); 8.04 (d, 1H, $^3$J=1.9 Hz, H-5'); 8.24 (d, 1H, $^3$J=9.8 Hz, H-4).

$^{13}$C-NMR (DMSO-d$_6$, 75 MHz): δ/ppm (TMS)=29.24 (5-O—CH$_2$CH$_2$CH$_2$—O—C$_6$H$_4$—O—C$_6$H$_5$); 64.52 and 69.47 (5-O—CH$_2$CH$_2$CH$_2$—O—C$_6$H$_4$—O—C$_6$H$_5$); 93.33 (C-8); 105.42 (C-4'); 106.06 (C-4a); 112.31 (C-3); 112.98 (C-6); 139.47 (C-4); 145.97 (C-5'); 148.54 (C-5); 152.06 (C-8a); 157.57 (C-7); 160.02 (C-2); 115.68, 117.23, 120.62, 122.52, 129.80, 149.45, 154.76 and 157.91 (—O—C$_6$H$_4$—O—C$_6$H$_5$).

IR (KBr): ν/cm$^{-1}$=3124, 2954, 1716, 1578, 1506, 1456, 1348, 1222.

MS (EI): m/z (%)=428 M$^+$ (50), 227 (19), 199 (57), 171 (6), 134 (100), 77 [C$_6$H$_5$]$^+$ (43), 51 (15).

Example 30

5-[3(4-Methylphenoxy)propoxy]psoralen (AS127)

4-[3-(4-Methylphenoxy)propoxy]-7H-furo[3,2-g][1]benzopyran-7-on

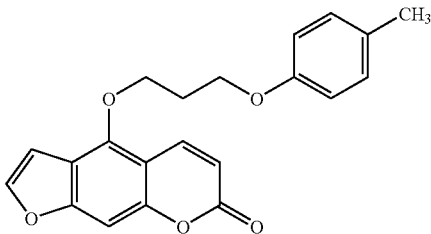

Melting point: 126.5° C.
Combustion analysis: C$_{21}$H$_{18}$O$_5$ (350.37)

| calculated: | C | 71.99 | H | 5.18 |
| found: | C | 72.27 | H | 5.24 |

$^1$H-NMR (DMSO-d$_6$, 300 MHz): δ/ppm (TMS)=2.22-2.30 (m, 5H, 5-O—CH$_2$CH$_2$CH$_2$—O—C$_6$H$_4$—CH$_3$ and —CH$_3$); 4.18 (t, 2H, $^3$J=6.2 Hz, 5-O—CH$_2$CH$_2$CH$_2$—O—C$_6$H$_4$—CH$_3$); 4.63 (t, 2H, $^3$J=6.1 Hz, 5-O—CH$_2$CH$_2$CH$_2$—O—C$_6$H$_4$—CH$_3$); 6.28 (d, 1H, $^3$J=9.8 Hz, H-3); 6.80 (d, 2H, $^3$J=8.5 Hz, H-3" and H-5"); 7.07 (d, 2H, $^3$J=8.3 Hz, H-2" and H-6"); 7.31 (d, 1H, $^3$J=2.3 Hz, H-4'); 7.33 (s, 1H, H-8); 8.02 (d, 1H, $^3$J=2.4 Hz, H-5'); 8.15 (d, 1H, $^3$J=9.8 Hz, H-4).

$^{13}$C-NMR (DMSO-d$_6$, 75 MHz): δ/ppm (TMS)=20.01 (—CH$_3$); 29.27 (5-O—CH$_2$CH$_2$CH$_2$—O—C$_6$H$_4$—CH$_3$); 64.06 and 69.54 (5-O—CH$_2$CH$_2$CH$_2$—O—C$_6$H$_4$—CH$_3$); 93.35 (C-8); 105.39 (C-4'); 106.1T (C-4a); 112.33 (C-3); 113.04 (C-6); 114.29 (C-3" and C-5"); 129.20 (C-4"); 129.78 (C-2" and C-6"); 139.45 (C-4); 145.98 (C-5'); 148.55 (C-5); 152.07 (C-8a); 156.30 (C-1"); 157.57 (C-7); 160.04 (C-2).

IR (KBr): ν/cm$^{-1}$=3126, 2954, 1720, 1622, 1511, 1454, 1351, 1240, 1129.

MS (EI): m/z (%)=350 M$^+$ (37), 215 (5), 202 [C$_{10}$H$_6$O$_4$]$^+$ (38), 174 (6), 149 [C$_{10}$H$_{13}$O]$^+$ (87), 121 [CH$_3$—C$_6$H$_4$O—CH$_2$]$^+$ (100), 91 [C$_7$H$_7$]$^+$ (58), 41 [C$_3$H$_5$]$^+$ (22).

Example 31

5-[3-(4-Ethylphenoxy)propoxy]psoralen (AS123)

4-[3-(4-Ethylphenoxy)propoxy]-7H-furo[3,2-g][1]benzopyran-7-on

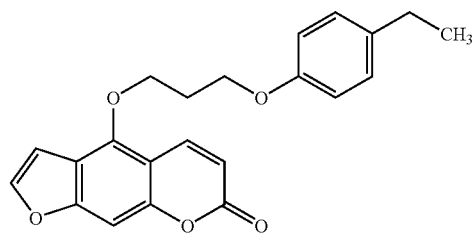

Melting point: 122° C.
Combustion analysis: C$_{22}$H$_{20}$O$_5$ (364.40)

| calculated: | C | 72.51 | H | 5.53 |
|---|---|---|---|---|
| found: | C | 72.50 | H | 5.62 |

$^1$H-NMR (DMSO-$d_6$, 300 MHz): δ/ppm (TMS)=1.14 (t, 3H, $^3$J=7.6 Hz, —CH$_2$CH$_3$); 2.27 (quint, $^3$J=7.6 Hz, 2H, 5-O—CH$_2$CH$_2$CH$_2$—O—C$_6$H$_4$—CH$_2$CH$_3$); 2.53 (q, 2H, $^3$J=7.7 Hz, —CH$_2$CH$_3$); 4.20 (t, 2H, $^3$J=6.2 Hz, 5-O—CH$_2$CH$_2$CH$_2$—O—C$_6$H$_4$—CH$_2$CH$_3$); 4.65 (t, 2H, $^3$J=6.0 Hz, 5-O—CH$_2$CH$_2$CH$_2$—O—C$_6$H$_4$—CH$_2$CH$_3$); 6.30 (d, 1H, $^3$J=9.8 Hz, H-3); 6.87 (d, 2H, $^3$J=8.4 Hz, H-3" and H-5"); 7.10 (d, 2H, $^3$J=8.4 Hz, H-2" and H-6"); 7.33 (d, 1H, $^3$J=1.4 Hz, H-4'); 7.35 (s, 1H, H-8); 8.04 (d, 1H, $^3$J=2.2 Hz, H-5'); 8.23 (d, 1H, $^3$J=9.8 Hz, H-4).

$^{13}$C-NMR (DMSO-$d_6$, 75 MHz): δ/ppm (TMS)=15.80 (—CH$_3$); 27.17 (—CH$_2$CH$_3$); 29.21 (5-O—CH$_2$CH$_2$CH$_2$—O—C$_6$H$_4$—C$_2$H$_5$); 64.00 and 69.49 (5-O—CH$_2$CH$_2$CH$_2$—O—C$_6$H$_4$—C$_2$H$_5$); 93.31 (C-8); 105.36 (C-4'); 106.06 (C-4a); 112.28 (C-3); 112.98 (C-6); 114.26 (C-3" and C-5"); 128.53 (C-2" and C-6"); 135.73 (C-4"); 139.42 (C-4); 145.94 (C-5'); 148.51 (C-5); 152.02 (C-8a); 156.41 (C-1"); 157.52 (C-7); 159.98 (C-2).

IR (KBr): ν/cm$^{-1}$=3124, 2952, 1724, 1622, 1512, 1454, 1350, 1238.

MS (EI): m/z (%)=364 M$^+$ (28), 243 (3), 202 [C$_{11}$H$_{16}$O$_4$]$^+$ (32), 163 [C$_{11}$H$_{15}$O]$^+$ (68), 135 [CH$_3$—CH$_2$C$_6$H$_4$O—CH$_2$]$^+$ (100), 107 [C$_8$H$_{11}$]$^+$ (43), 79 (34), 41 [C$_3$H$_5$]$^+$ (19).

Example 32

5-[3-(4-Fluorphenoxy)propoxy]psoralen (AS133)

4-[3-(4-Fluorphenoxy)propoxy]-7H-furo[3,2-g][1]benzopyran-7-on

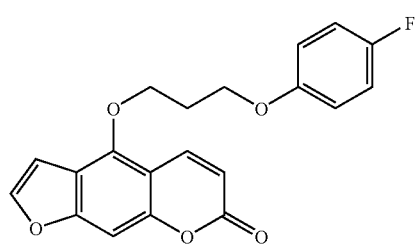

Melting point: 123° C.
Combustion analysis: C$_{20}$H$_{15}$FO$_5$ (354.34)

| calculated: | C | 67.79 | H | 4.27 |
|---|---|---|---|---|
| found: | C | 68.04 | H | 4.42 |

$^1$H-NMR (DMSO-$d_6$, 300 MHz): δ/ppm (TMS)=2.28 (quint, 2H, $^3$J=6.1 Hz, 5-O—CH$_2$CH$_2$CH$_2$—O—C$_6$H$_4$—F); 4.21 (t, 2H, $^3$J=6.2 Hz, 5-O—CH$_2$CH$_2$CH$_2$—O—C$_6$H$_4$—F); 4.65 (t, 2H, $^3$J=6.0 Hz, 5-O—CH$_2$CH$_2$CH$_2$—O—C$_6$H$_4$—F); 6.30 (d, 1H, $^3$J=9.8 Hz, H-3); 6.95-7.00 (m, 2H, 5-O—CH$_2$CH$_2$CH$_2$—O—C$_6$H$_4$—F); 7.07-7.14 (m, 2H, 5-O—CH$_2$CH$_2$CH$_2$—O—C$_6$H$_4$—F); 7.33 (d, 1H, $^3$J=2.1 Hz, H-4'); 7.35 (s, 1H, H-8); 8.04 (d, 1H, $^3$J=2.3 Hz, H-5'); 8.23 (d, 1H, $^3$J=9.8 Hz, H-4).

$^{13}$C-NMR (DMSO-$d_6$, 75 MHz): δ/ppm (TMS)=29.18 (5-O—CH$_2$CH$_2$CH$_2$—O—C$_6$H$_4$—F); 64.71 and 69.45 (5-O—CH$_2$CH$_2$CH$_2$—O—C$_6$H$_4$—F); 93.34 (C-8); 105.38 (C-4'); 106.07 (C-4a); 112.31 (C-3); 113.00 (0-6); 115.60, 115.72 and 115.90 (C-2", C-3", C-5" and C-6"); 139.45 (C-4); 145.97 (C-5'); 148.51 (C-5); 152.04 (C-8a); 154.72 (C-4"); 157.55 (C-7); 158.01 (C-1"); 160.01 (C-2).

IR (KBr): ν/cm$^{-1}$=3128, 2954, 1717, 1620, 1508, 1455, 1353, 1213.

MS (EI): m/z (%)=354 M$^+$ (26), 202 [C$_{11}$H$_6$O$_4$]$^+$ (46), 153 [C$_{10}$H$_{12}$OF]$^+$ (48), 125 [F—C$_6$H$_4$O—CH$_2$]$^+$ (100), 95 (36), 83 (13), 41 [C$_3$H$_5$]$^+$ (64).

Example 33

5-[3-(3-Trifluormethylphenoxy)propoxy]psoralen (AS124)

4-[3-(3-Trifluormethylphenoxy)propoxy]-7H-furo[3,2-g][1]benzopyran-7-on

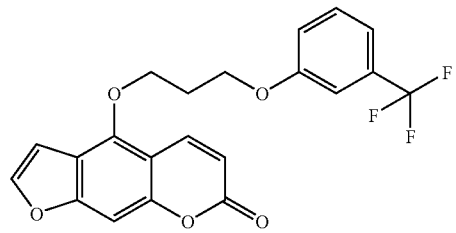

Melting point: 137° C.
Combustion analysis: C$_{21}$H$_{15}$F$_3$O$_5$ (404.35)

| calculated: | C | 62.38 | H | 3.47 |
|---|---|---|---|---|
| found: | C | 62.13 | H | 3.78 |

$^1$H-NMR (DMSO-$d_6$, 300 MHz): δ/ppm (TMS)=2.30 (t, 2H, $^3$J=5.5 Hz, 5-O—CH$_2$CH$_2$CH$_2$—O—C$_6$H$_4$—CF$_3$); 4.32 (s, 2H, 5-O—CH$_2$CH$_2$CH$_2$—O—C$_6$H$_4$—CF$_3$); 4.67 (s, 2H, 5-O—CH$_2$CH$_2$CH$_2$—O—C$_6$H$_4$—CF$_3$); 6.27 (d, 1H, $^3$J=9.6 Hz, H-3); 7.23-7.33 (m, 5H, H-2", H-4", H-6", H-8 and)H-4'); 7.51 (t, 1H, $^3$J=7.7 Hz, H-5"); 8.03 (s, 1H, H-5'); 8.23 (d, 1H, $^3$J=10.0 Hz, H-4).

$^{13}$C-NMR (DMSO-$d_6$, 75 MHz): δ/ppm (TMS)=29.08 (5-O—CH$_2$CH$_2$CH$_2$—O—C$_6$H$_4$—CF$_3$); 64.75 and 69.36 (5-O—CH$_2$CH$_2$CH$_2$—O—C$_6$H$_4$—CF$_3$); 93.31 (C-8); 105.44 (C-4'); 106.02 (C-4a); 110.93, 110.98, 117.06, 117.06, 130.48 and 130.67 (5-O—CH$_2$(CH$_2$)$_2$CH$_2$—O—C$_6$H$_4$—CF$_3$); 112.26 (C-3); 112.94 (C-6); 118.73 (—CF$_3$); 139.51 (C-4); 145.97 (C-5'); 148.53 (C-5); 152.06 (C-8a); 157.58 (C-7); 158.72 (C-1"); 160.01 (C-2).

IR (KBr): ν/cm$^{-1}$=3126, 2924, 1724, 1622, 1454, 1342, 1242, 1130.

MS (EI): m/z (%)=404 M$^+$ (56), 216 (2), 175 [C$_{12}$H$_{15}$O]$^+$ (100), 145 (56), 127 (12), 89 (14), 41 [C$_3$H$_5$]$^+$ (84).

Example 34

5-[3-(1-Naphthyloxy)propoxy]psoralen (AS135)

4-[3-(1-Naphthyloxy)propoxy]-7H-furo[3,2-g][1]benzopyran-7-on

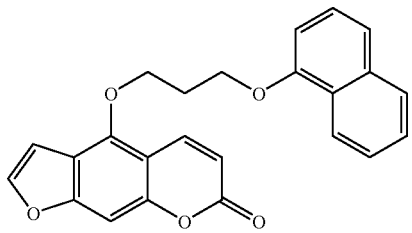

Melting point: 140° C.
Combustion analysis: $C_{24}H_{18}O_5$ (386.41)

| calculated: | C | 74.60 | H | 4.70 |
|---|---|---|---|---|
| found: | C | 75.33 | H | 4.81 |

$^1$H-NMR (DMSO-$d_6$, 300 MHz): δ/ppm (TMS)=2.43 (quint, 2H, $^3J$=6.1 Hz, 5-O—CH$_2$CH$_2$CH$_2$—O—C$_{10}$H$_7$); 4.43 (t, 2H, $^3J$=6.0 Hz, 5-O—CH$_2$C$\overline{H}_2$CH$_2$—O—C$_{10}$H$_7$); 4.79 (t, 2H, $^3J$=6.0 Hz, 5-O—CH$_2$CH$_2$C$\overline{H}_2$—O—C$_{10}$H$_7$); 6.21 (d, 1H, $^3J$=9.8 Hz, H-3); 7.03 (d, 1H, $^3J$=7.3 Hz, H-2''); 7.34 (s, 1H, H-8); 7.36 (d, 1H, $^3J$=2.2 Hz, H-4'); 7.39-7.53 (m, 4H, 5-O—CH$_2$CH$_2$CH$_2$—O—C$_{10}$H$_7$); 7.86 (d, 1H, $^3J$=7.9 Hz, H-5''); 8.03 (d, 1H, $^3J$=2.3 Hz, $\overline{H}$-5'); 8.14 (d, 1H, $^3J$=8.1 Hz, H-8''); 8.24 (d, 1H, $^3J$=9.8 Hz, H-4).

$^{13}$C-NMR (DMSO-$d_6$, 75 MHz): δ/ppm (TMS)=29.25 (5-O—CH$_2$CH$_2$CH$_2$—O—C$_{10}$H$_7$); 64.45 and 69.66 (5-O—CH$_2$CH$_2$C$\overline{H}_2$—O—C$_{10}$H$_7$); 93.32 (C-8); 105.07 (C-2''); 105.39 ($\overline{C}$-4'); 106.06 (C-4a); 112.20 (C-3); 113.01 (C-6); 119.73 (C-4''); 121.28 (C-8''); 124.86, 125.03, 126.13, 126.29 and 127.36 (C-3'', C-5'', C-6'', C-7'' and C-8a''); 133.95 (C-4a''); 139.39 (C-4); 145.94 (C-5''); 148.55 (C-5); 152.03 (C-8a); 153.84 (C-1''); 157.54 (C-7); 159.97 (C-2).

IR (KBr): ν/cm$^{-1}$=3126, 2949, 1721, 1622, 1580, 1454, 1351, 1129.

MS (EI): m/z (%)=386 M$^+$ (63), 243 (25), 215 (24), 185 [$C_{13}H_{13}O$]$^+$ (100), 157 [$C_{11}H_9O$]$^+$ (65), 115 (36), 89 (12), 41 [$C_3H_5$]$^+$ (13).

Example 35

5-[3-(2-Naphthyloxy)propoxy]psoralen (AS137)

4-[3-(2-Naphthyloxy)propoxy]-7H-furo[3,2-g][1]benzopyran-7-on

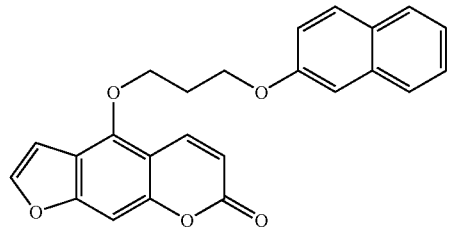

Melting point: 151° C.
Combustion analysis: $C_{25}H_{20}O_5$ (400.44)

| calculated: | C | 74.60 | H | 4.70 |
|---|---|---|---|---|
| found: | C | 75.11 | H | 4.81 |

$^1$H-NMR (DMSO-$d_6$, 300 MHz): δ/ppm (TMS)=2.35 (quint, 2H, $^3J$=6.1 Hz, 5-O—CH$_2$CH$_2$CH$_2$—O—C$_{10}$H$_7$); 4.35 (t, 2H, $^3J$=6.2 Hz, 5-O—CH$_2$C$\overline{H}_2$CH$_2$—O—C$_{10}$H$_7$); 4.68 (t, 2H, $^3J$=6.0 Hz, 5-O—CH$_2$CH$_2$C$\overline{H}_2$—O—C$_{10}$H$_7$); 6.25 (d, 1H, $^3J$=9.8 Hz, H-3); 7.17 (dd, 1H, $^3J$=9.0 Hz, $^4J$=2.4 Hz, H-3''); 7.30-7.35 (m, 4H, H-8, H-4' and 5-O—CH$_2$CH$_2$CH$_2$—O—C$_{10}$H$_7$); 7.44 (t, 1H, $^3J$=7.0 Hz, H-7''); 7.76-7.82 (m, 3H, 5-O—CH$_2$CH$_2$CH$_2$—O—C$_{10}$H$_7$); 8.01 (d, 1H, $^3J$=2.2 Hz, H-5'); 8.22 (d, 1H, $^3J$=9.8 Hz, $\overline{H}$-4).

$^{13}$C-NMR (DMSO-$d_6$, 75 MHz): δ/ppm (TMS)=29.22 (5-O—CH$_2$CH$_2$CH$_2$—O—C$_{10}$H$_7$); 64.26 and 69.52 (5-O—CH$_2$CH$_2$C$\overline{H}_2$—O—C$_{10}$H$_7$); 93.31 (C-8); 105.42 (C-4'); 106.05 ($\overline{C}$-4a); 106.80 (C-1''); 112.28 (C-3); 112.96 (C-6); 118.60 (C-3''); 123.53 (C-6''); 126.33, 126.60, 127.44, 128.46 and 129.27 (C-4'', C-4a'', C-5'', C-7'' and C-8''); 134.23 (C-8a''); 139.45 (C-4); 145.96 (C-5'); 148.52 (C-5); 152.06 (C-8a); 156.32 (C-2''); 157.57 (C-7); 160.02 (C-2).

IR (KBr): ν/cm$^{-1}$=3133, 3046, 1720, 1452, 1349, 1130.

MS (EI): m/z (%)=386 M$^+$ (59), 215 (6), 185 [$C_{13}H_{13}O$]$^+$ (100), 157 [$C_{11}H_9O$]$^+$ (59), 127 (41), 89 (8), 41 [$C_3H_5$]$^+$ (8).

Example 36

5-(5-Phenoxypentoxy)psoralen (AS121)

4-(5-Phenoxypentoxy)-7H-furo[3,2-g][1]benzopyran-7-on

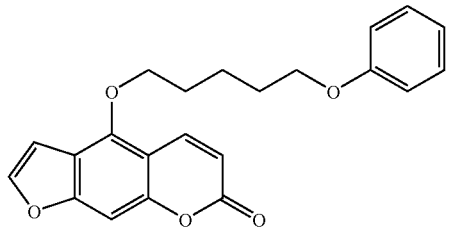

Melting point: 91° C.
Combustion analysis: $C_{22}H_{20}O_5$ (364.40)

| calculated: | C | 72.51 | H | 5.53 |
|---|---|---|---|---|
| found: | C | 72.74 | H | 5.68 |

$^1$H-NMR (DMSO-$d_6$, 300 MHz): δ/ppm (TMS)=1.63-1.71 (m, 2H, 5-O—CH$_2$CH$_2$CH$_2$CH$_2$CH$_2$—O—C$_6$H$_5$); 1.77-1.93 (m, 4H, 5-O—CH$_2$CH$_2$CH$_2$CH$_2$CH$_2$—O—C$_6$H$_5$); 4.00 (t, 2H, $^3J$=6.2 Hz, 5-O—$\overline{C}$H$_2$CH$_2$CH$_2$CH$_2$CH$_2$—O—C$_6$H$_5$); 4.52 (t, 2H, $^3J$=6.0 Hz, 5-O—CH$_2$CH$_2$CH$_2$C$\overline{H}_2$CH$_2$—O—C$_6$H$_5$); 6.30 (d, 1H, $^3J$=9.7 Hz, H-3); 6.90-6.93 (m, 3H, 5-O—CH$_2$CH$_2$CH$_2$CH$_2$CH$_2$—O—C$_6$H$_5$); 7.25-7.33 (m, 4H, H-8, H-4' and 5-O—CH$_2$CH$_2$CH$_2$C$\overline{H}_2$CH$_2$—O—C$_6$H$_5$); 8.02 (s, 1H, H-5'); 8.19 (d, 1H, $^3J$=9.7 Hz, H-4).

$^{13}$C-NMR (DMSO-d$_6$, 75 MHz): δ/ppm (TMS)=22.02 (5-O—CH$_2$CH$_2$CH$_2$CH$_2$CH$_2$—O—C$_6$H$_5$); 28.31 and 29.01 (5-O—CH$_2$CH$_2$CH$_2$CH$_2$CH$_2$—O—C$_6$H$_5$); 67.06 and 72.49 (5-O—CH$_2$CH$_2$CH$_2$CH$_2$CH$_2$—O—C$_6$H$_5$); 93.20 (C-8); 105.55 (C-4'); 106.04 (C-4a); 112.30 (C-3); 113.01 (C-6); 114.34 (C-3" and C-5"); 120.32 (C-4"); 129.39 (C-2" and C-6"); 139.38 (C-4); 145.88 (C-5'); 148.74 (C-5); 152.08 (C-8a); 157.59 (C-1"); 158.58 (C-7); 160.05 (C-2).

IR (KBr): ν/cm$^{-1}$=3130, 2946, 2872, 1716, 1602, 1496, 1350, 1242, 1134.

MS (EI): m/z (%)=364 M$^+$ (9), 202 [C$_{11}$H$_6$O$_4$]$^+$ (22), 163 [C$_{11}$H$_{15}$O]$^+$ (44), 107 [C$_6$H$_5$O—CH$_2$]$^+$ (40), 69 [C$_5$H$_9$]$^+$ (100), 41 [C$_3$H$_5$]$^+$ (52).

Example 37

5-[3-(4-Methoxyphenoxy)pentoxy]psoralen (AS125)

4-[5-(4-Methoxyphenoxy)pentoxy]-7H-furo[3,2-g][1]benzopyran-7-on

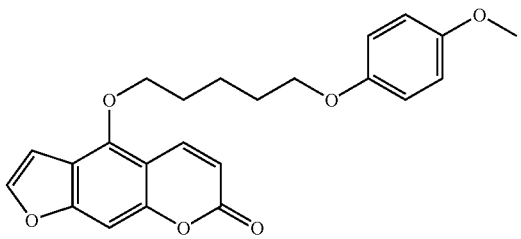

Melting point: 87.5° C.
Combustion analysis: C$_{23}$H$_{22}$O$_6$ (394.43)

| calculated: | C | 70.04 | H | 5.62 |
| --- | --- | --- | --- | --- |
| found: | C | 69.32 | H | 5.63 |

$^1$H-NMR (DMSO-d$_5$, 300 MHz): δ/ppm (TMS)=1.61-1.93 (m, 6H, 5-O—CH$_2$CH$_2$CH$_2$CH$_2$CH$_2$—O—C$_6$H$_4$—OCH$_3$); 3.68 (s, 3H, —OCH$_3$); 3.93 (t, 2H, $^3$J=6.1 Hz, 5-O—CH$_2$CH$_2$CH$_2$CH$_2$CH$_2$—O—C$_6$H$_4$—OCH$_3$); 4.52 (t, 2H, $^3$J=6.2 Hz, 5-O—CH$_2$CH$_2$CH$_2$CH$_2$CH$_2$—O—C$_6$H$_4$—OCH$_3$); 6.31 (d, 1H, $^3$J=9.8 Hz, H-3); 6.84 (s, 4H, 5-O—CH$_2$CH$_2$CH$_2$CH$_2$CH$_2$—O—C$_6$H$_4$—OCH$_3$); 7.32 (d, 1H, $^3$J=2.3 Hz, H-4'); 7.35 (s, 1H, H-8); 8.03 (d, 1H, $^3$J=2.4 Hz, H-5'); 8.20 (d, 1H, $^3$J=9.8 Hz, H-4).

$^{13}$C-NMR (DMSO-d$_6$, 75 MHz): δ/ppm (TMS)=22.03 (5-O—CH$_2$CH$_2$CH$_2$CH$_2$CH$_2$—O—C$_6$H$_4$—OCH$_3$); 28.39 and 29.03 (5-O—CH$_2$CH$_2$CH$_2$CH$_2$CH$_2$—O—C$_6$H$_4$—OCH$_3$); 55.31 (—OCH$_3$); 64.55 and 69.52 (5-O—CH$_2$CH$_2$CH$_2$CH$_2$CH$_2$—O—C$_6$H$_4$—OCH$_3$); 93.24 (C-8); 105.57 (C-4'); 106.08 (C-4a); 112.34 (C-3); 113.05 (C-6); 114.54 and 115.26 (C-2", C-3", C-5" and C-6"); 139.42 (C-4); 145.91 (C-5'); 148.77 (C-5); 152.10 (C-8a); 152.61 and 153.22 (C-1" and C-4"); 157.61 (C-7); 160.08 (C-2).

IR (KBr): ν/cm$^{-1}$=3123, 2932, 2866, 1725, 1628, 1508, 1457, 1343, 1232, 1130.

Example 38

5-[5-(3,5-Dimethoxyphenoxy)pentoxy]psoralen (AS126)

4-[5-(3,5-Dimethoxyphenoxy)pentoxy]-7H-furo[3,2-g][1]benzopyran-7-on

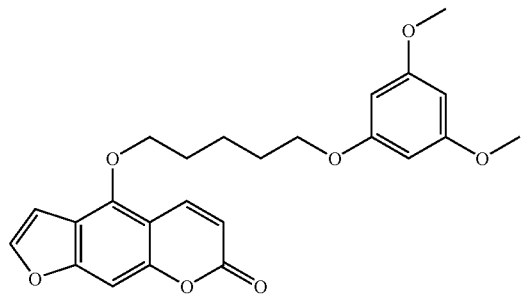

Melting point: 134.5° C.
Combustion analysis: C$_{24}$H$_{24}$O$_7$ (424.45)

| calculated: | C | 67.92 | H | 5.66 |
| --- | --- | --- | --- | --- |
| found: | C | 68.30 | H | 5.85 |

$^1$H-NMR (DMSO-d$_6$, 300 MHz):
δ/ppm (TMS)=1.64-1.86 (m, 6H, 5-O—CH$_2$CH$_2$CH$_2$CH$_2$CH$_2$—O—C$_6$H$_3$—(OCH$_3$)$_2$); 3.69 (s, 6H, —(OCH$_3$)$_2$); 3.96 (s, 2H, 5-O—CH$_2$CH$_2$CH$_2$CH$_2$CH$_2$—O—C$_6$H$_3$—(OCH$_3$)$_2$); 4.51 (t, 2H, 5-O—CH$_2$CH$_2$CH$_2$CH$_2$CH$_2$—O—C$_6$H$_3$—(OCH$_3$)$_2$); 6.07 (s, 3H, H-2", H-4" and H-6"); 6.30 (d, 1H, $^3$J=9.3 Hz, H-3); 7.33 (s, 2H, H-8 and H-4'); 8.02 (s, 1H, H-5'); 8.19 (d, 1H, $^3$J=9.2 Hz, H-4).

$^{13}$C-NMR (DMSO-d$_6$, 75 MHz): δ/ppm (TMS)=22.01 (5-O—CH$_2$CH$_2$CH$_2$CH$_2$CH$_2$—O—C$_6$H$_3$—(OCH$_3$)$_2$); 28.26 and 29.00 (5-O—CH$_2$CH$_2$CH$_2$CH$_2$CH$_2$—O—C$_6$H$_3$—(OCH$_3$)$_2$); 55.06 (—(OCH$_3$)$_2$); 67.24 and 72.48 (5-O—CH$_2$CH$_2$CH$_2$CH$_2$CH$_2$—O—C$_6$H$_3$—(OCH$_3$)$_2$); 92.76 (C-8); 93.20 (C-2", C-4" and C-6"); 105.56 (C-4'); 106.04 (C-4a); 112.30 (C-3); 113.01 (C-6); 139.39 (C-4); 145.88 (C-5'); 148.75 (C-5); 152.09 (C-8a); 157.60 (C-7); 160.05 (C-2); 160.48 (C-1"); 161.10 (C-3" and C-5").

IR (KBr): ν/cm$^{-1}$=3120, 2956, 1720, 1602, 1456, 1354,
MS (EI): m/z (%)=424 M$^+$ (27), 270 (6), 223 [C$_{13}$H$_{19}$O$_3$]$^+$ (100), 202 [C$_{11}$H$_6$O$_4$]$^+$ (19), 155 (81), 137 [CH$_3$—O—C$_6$H$_4$O—CH$_2$]$^+$ (28), 69 (82), 41 [C$_3$H$_5$]$^+$ (70).

Example 39

5-[5(4-Nitrophenoxy)pentoxy]psoralen (AS139)

4-[5-(4-Nitrophenoxy)pentoxy]-7H-furo[3,2-g][1]benzopyran-7-on

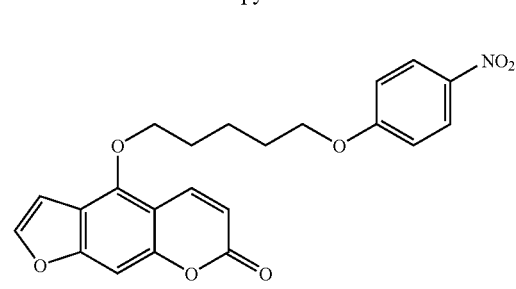

Melting point: 126.5° C.
Combustion analysis: C$_{22}$H$_{19}$NO$_7$ (409.40) 1208.

| calculated: | C | 64.54 | H | 4.86 | N | 3.42 |

$^1$H-NMR (DMSO-d$_6$, 300 MHz): δ/ppm (TMS)=1.52-1.57 (m, 2H, 5-O—CH$_2$CH$_2$CH$_2$CH$_2$CH$_2$—O—C$_6$H$_4$—NO$_2$); 1.66-1.68 (m, 4H, 5-O—CH$_2$CH$_2$CH$_2$CH$_2$CH$_2$—O—C$_6$H$_4$—NO$_2$); 4.17 (s, 2H, 5-O—CH$_2$CH$_2$CH$_2$CH$_2$CH$_2$—O—C$_6$H$_4$—NO$_2$); 4.52 (s, 2H, 5-O—CH$_2$CH$_2$CH$_2$CH$_2$CH$_2$—O—C$_6$H$_4$—NO$_2$); 6.32 (d, 1H, $^3$J=9.9 Hz, H-3); 7.14 (d, 2H, $^3$J=7.7 Hz, 5-O—CH$_2$CH$_2$CH$_2$CH$_2$CH$_2$—O—C$_6$H$_4$—NO$_2$); 7.32 (s, 2H, H-8 and H-4'); 8.02 (s, 1H, H-5'); 8.17-8.20 (m, 3H, H-4 and 5-O—CH$_2$CH$_2$CH$_2$CH$_2$CH$_2$—O—C$_6$H$_4$—NO$_2$).

$^{13}$C-NMR (CDCl$_3$, 75 MHz): δ/ppm (TMS)=22.66 (5-O—CH$_2$CH$_2$CH$_2$CH$_2$CH$_2$—O—C$_6$H$_4$—NO$_2$); 28.78 and 29.76 (5-O—CH$_2$CH$_2$CH$_2$CH$_2$CH$_2$—O—C$_6$H$_4$—NO$_2$); 68.47 and 72.66 (5-O—CH$_2$CH$_2$CH$_2$CH$_2$CH$_2$—O—C$_6$H$_4$—NO$_2$); 94.02 (C-8); 105.06 (C-4'); 106.80 (C-4a); 112.68 (C-3); 113.35 (C-6); 114.39 (C-2" and C-6"); 125.95 (C-3" and C-5"); 139.18 (C-4); 141.54 (C-4"); 144.89 (C-5'); 148.91 (C-5); 152.75 (C-8a); 158.29 (C-7); 161.13 (C-2); 164.00 (C-1").

IR (KBr): ν/cm$^{-1}$=3126, 2959, 1729, 1594, 1507, 1339, 1264.

MS (EI): m/z (%)=409 M$^+$ (19), 202 [C$_{11}$H$_6$O$_4$]$^+$ (58), 174 [202-CO]$^+$ (21), 152 [O$_2$N—C$_6$H$_4$O—CH$_2$]$^+$ (17), 69 (100), 41 [C$_3$H$_5$]$^+$ (79).

Example 40

5-[5-(4-Chlorphenoxy)pentoxy]psoralen (AS131)

4-[5-(4-Chlorphenoxy)pentoxy]-7H-furo[3,2-g][1]benzopyran-7-on

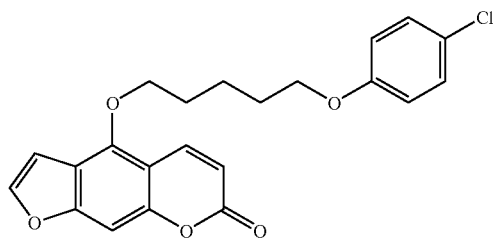

Melting point: 126.5° C.
Combustion analysis: C$_{22}$H$_{19}$ClO$_5$ (398.85)

| calculated: | C | 66.25 | H | 4.80 |
| found: | C | 66.62 | H | 4.91 |

$^1$H-NMR (DMSO-d$_6$, 300 MHz): δ/ppm (TMS)=1.58-1.68 (m, 2H, 5-O—CH$_2$CH$_2$CH$_2$CH$_2$CH$_2$—O—C$_6$H$_4$—Cl); 1.75-1.92 (m, 4H, 5-O—CH$_2$CH$_2$CH$_2$CH$_2$CH$_2$—O—C$_6$H$_4$—Cl); 3.99 (t, 2H, $^3$J=6.3 Hz, 5-O—CH$_2$CH$_2$CH$_2$CH$_2$CH$_2$—O—C$_6$H$_4$—Cl); 4.50 (t, 2H, $^3$J=6.2 Hz, 5-O—CH$_2$CH$_2$CH$_2$CH$_2$CH$_2$—O—C$_6$H$_4$—Cl); 6.30 (d, 1H, $^3$J=9.8 Hz, H-3); 6.92-6.95 (m, 2H, 5-O—CH$_2$CH$_2$CH$_2$CH$_2$CH$_2$—O—C$_6$H$_4$—Cl); 7.28-7.32 (m, 4H, H-8, H-4' and 5-O—CH$_2$CH$_2$CH$_2$CH$_2$CH$_2$—O—C$_6$H$_4$—Cl); 8.01 (d, 1H, $^3$J=2.3 Hz, H-5'); 8.17 (d, 1H, $^3$J=9.8 Hz, H-4).

$^{13}$C-NMR (DMSO-d$_6$, 75 MHz): δ/ppm (TMS)=21.93 (5-O—CH$_2$CH$_2$CH$_2$CH$_2$CH$_2$—O—C$_6$H$_4$—Cl); 28.17 and 28.96 (5-O—CH$_2$CH$_2$CH$_2$CH$_2$CH$_2$—O—C$_6$H$_4$—Cl); 67.59 and 72.43 (5-O—CH$_2$CH$_2$CH$_2$CH$_2$CH$_2$—O—C$_6$H$_4$—Cl); 93.16 (C-8); 105.53 (C-4'); 106.00 (C-4a); 112.27 (C-3); 112.97 (C-6); 116.09 (C-2" and C-6"); 123.99 (C-4"); 129.11 (C-3" and C-5"); 139.34 (C-4); 145.84 (C-5'); 148.70 (C-5); 152.06 (C-8a); 157.42 (C-7); 157.57 (C-1"); 160.03 (C-2).

IR (KBr): ν/cm$^{-1}$=3155, 2940, 1719, 1622, 1579, 1451, 1350, 1246.

MS (EI): m/z (%)=398 M$^+$ (10), 197 [C$_{11}$H$_{14}$OCl]$^+$ (30), 174 (11), 141 [C$_1$-C$_6$H$_4$O—CH$_2$]$^+$ (22), 111 (10), 69 [C$_5$H$_9$]$^+$ (100), 41 [C$_3$H$_5$]$^+$ (50).

Example 41

5-[5-(4-Phenoxyphenoxy)pentoxy]psoralen (AS138)

4-[5-(4-Phenoxyphenoxy)pentoxy]-7H-furo[3,2-g][1]benzopyran-7-on

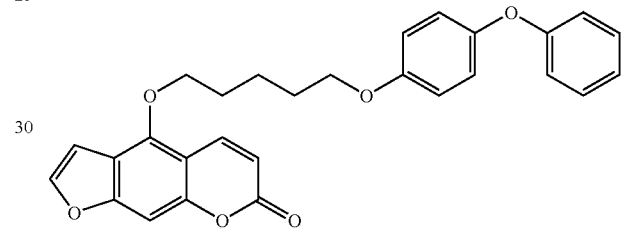

Melting point: 100° C.
Combustion analysis: C$_{28}$H$_{24}$O$_6$ (456.50)

| calculated: | C | 73.67 | H | 5.30 |
| found: | C | 73.49 | H | 5.36 |

$^1$H-NMR (DMSO-d$_6$, 300 MHz): δ/ppm (TMS)=1.61-1.68 (m, 2H, 5-O—CH$_2$CH$_2$CH$_2$CH$_2$CH$_2$—O—C$_6$H$_4$—O—C$_6$H$_5$); 1.77-1.94 (m, 4H, 5-O—CH$_2$CH$_2$CH$_2$CH$_2$CH$_2$—O—C$_6$H$_4$—O—C$_6$H$_5$); 4.00 (t, 2H, $^3$J=6.2 Hz, 5-O—CH$_2$CH$_2$CH$_2$CH$_2$CH$_2$—O—C$_6$H$_4$—O—C$_6$H$_5$); 4.52 (t, 2H, $^3$J=6.2 Hz, 5-O—CH$_2$CH$_2$CH$_2$CH$_2$CH$_2$—O—C$_6$H$_4$—O—C$_6$H$_5$); 6.31 (d, 1H, $^3$J=9.8 Hz, H-3); 6.91-7.00 (m, 6H, —O—C$_6$H$_4$—O—C$_6$H$_5$); 7.07 (t, 1H, $^3$J=7.4 Hz, H-4'''); 7.31-7.37 (m, 4H, H-8, H-4' and —O—C$_6$H$_4$—O—C$_6$H$_5$); 8.02 (d, 1H, $^3$J=2.2 Hz, H-5'); 8.18 (d, 1H, $^3$J=9.8 Hz, H-4).

$^{13}$C-NMR (DMSO-d$_6$, 75 MHz): δ/ppm (TMS)=22.01 (5-O—CH$_2$CH$_2$CH$_2$CH$_2$CH$_2$—O—C$_6$H$_4$—O—C$_6$H$_5$); 28.34 and 29.01 (5-O—CH$_2$CH$_2$CH$_2$CH$_2$CH$_2$—O—C$_6$H$_4$—O—C$_6$H$_5$); 67.63 and 72.46 (5-O—CH$_2$CH$_2$CH$_2$CH$_2$CH$_2$—O—C$_6$H$_4$—O—C$_6$H$_5$); 93.16 (C-8); 105.54 (C-4'); 106.01 (C-4a); 112.27 (C-3); 112.97 (C-6); 139.33 (C-4); 145.84 (C-5'); 148.71 (C-5); 152.07 (C-8a); 157.58 (C-7); 160.04 (C-2); 115.57, 117.23, 120.58, 122.48, 129.79, 149.28, 154.97 and 157.95 (—O—C$_6$H$_4$—O—C$_6$H$_5$).

IR (KBr): ν/cm$^{-1}$=2949, 1725, 1626, 1580, 1340, 1223.

MS (EI): m/z (%)=456 M$^+$ (39), 255 (28), 199 (27), 186 (32), 141 (13), 69 [C$_5$H$_9$]$^+$ (100), 41 [C$_3$H$_5$]$^+$ (65).

Example 42

5-[5-(4-Methylphenoxy)pentoxy]psoralen (AS129)

4-[5-(4-Methylphenoxy)pentoxy]-7H-furo[3,2-g][1]benzopyran-7-on

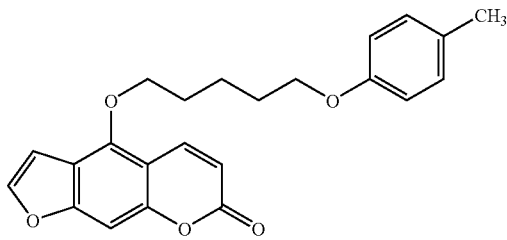

Melting point: 83° C.
Combustion analysis: $C_{23}H_{22}O$ (378.43)

| | | | | |
|---|---|---|---|---|
| calculated: | C | 73.01 | H | 5.86 |
| found: | C | 73.41 | H | 6.09 |

$^1$H-NMR (DMSO-$d_6$, 300 MHz): δ/ppm (TMS)=1.64-1.69 (m, 2H, 5-O—CH$_2$CH$_2$CH$_2$CH$_2$CH$_2$—O—C$_6$H$_4$—CH$_3$); 1.75-1.90 (m, 4H, 5-O—CH$_2$CH$_2$CH$_2$CH$_2$CH$_2$—O—C$_6$H$_4$—CH$_3$); 2.51 (s, 3H, —CH$_3$); 3.95 (t, 2H, $^3$J=6.2 Hz, 5-O—CH$_2$CH$_2$CH$_2$CH$_2$CH$_2$—O—C$_6$H$_4$—CH$_3$); 4.51 (t, 2H, $^3$J=6.1 Hz, 5-O—CH$_2$CH$_2$CH$_2$CH$_2$CH$_2$—O—C$_6$H$_4$—CH$_3$); 6.30 (d, 1H, $^3$J=9.8 Hz, H-3); 6.80 (d, 2H, $^3$J=8.4 Hz, H-3" and H-5"); 7.06 (d, 2H, $^3$J=8.2 Hz, H-2" and H-6"); 7.31 (d, 1H, $^3$J=1.6 Hz, H-4'); 7.33 (s, 1H, H-8); 8.02 (d, 1H, $^3$J=2.2 Hz, H-5'); 8.18 (d, 1H, $^3$J=9.8 Hz, H-4).

$^{13}$C-NMR (DMSO-$d_6$, 75 MHz): δ/ppm (TMS)=19.98 (—CH$_3$); 22.00 (5-O—CH$_2$CH$_2$CH$_2$CH$_2$CH$_2$—O—C$_6$H$_4$—CH$_3$); 28.32 and 29.00 (5-O—CH$_2$CH$_2$CH$_2$CH$_2$CH$_2$—O—C$_6$H$_4$—CH$_3$); 67.12 and 72.47 (5-O—CH$_2$CH$_2$CH$_2$CH$_2$CH$_2$—O—C$_6$H$_4$—CH$_3$); 93.17 (C-8); 105.54 (C-4'); 106.02 (C-4a); 112.28 (C-3); 112.99 (C-6); 114.18 (C-3" and C-5"); 128.90 (C-4"); 129.69 (C-2" and C-6"); 139.36 (C-4); 145.85 (C-5'); 148.72 (C-5); 152.07 (C-8a); 156.45 (C-1"); 157.58 (C-7); 160.03 (C-2).

IR (KBr): ν/cm$^{-1}$=3154, 2939, 1722, 1625, 1511, 1457, 1345, 1243, 1131.

MS (EI): m/z (%)=378 M$^+$ (12), 202 [$C_{11}H_6O_4$]$^+$ (14), 177 [$C_{12}H_{17}O$]$^+$ (53), 121 [CH$_3$—C$_6$H$_4$O—CH$_2$]$^+$ (49), 69 [$C_5H_9$]$^+$ (100), 41 [$C_3H_5$]$^+$ (45).

Example 43

5-[5-(4-Ethylphenoxy)pentoxy]psoralen (AS93)

4-[5-(4-Ethylphenoxy)pentoxy]-7H-furo[3,2-g][1]benzopyran-7-on

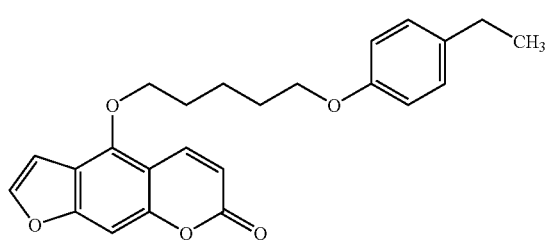

Melting point: 88° C.
Combustion analysis: $C_{24}H_{24}O_5$ (392.46)

| | | | | |
|---|---|---|---|---|
| calculated: | C | 73.45 | H | 6.16 |
| found: | C | 73.36 | H | 6.28 |

$^1$H-NMR (DMSO-$d_6$, 300 MHz): δ/ppm (TMS)=1.14 (t, 3H, $^3$J=7.6 Hz, —CH$_2$CH$_3$); 1.61-1.69 (m, 2H, 5-O—CH$_2$CH$_2$CH$_2$CH$_2$CH$_2$—O—C$_6$H$_4$—CH$_2$CH$_3$); 1.75-1.93 (m, 4H, 5-O—CH$_2$CH$_2$CH$_2$CH$_2$CH$_2$—O—C$_6$H$_4$—CH$_2$CH$_3$); 2.54 (q, 2H, $^3$J=7.5 Hz, —CH$_2$CH$_3$); 3.96 (t, 2H, $^3$J=6.3 Hz, 5-O—CH$_2$CH$_2$CH$_2$CH$_2$CH$_2$—O—C$_6$H$_4$—CH$_2$CH$_3$); 4.52 (t, 2H, $^3$J=6.2 Hz, 5-O—CH$_2$CH$_2$CH$_2$CH$_2$CH$_2$—O—C$_6$H$_4$—CH$_2$CH$_3$); 6.30 (d, 1H, $^3$J=9.8 Hz, H-3); 6.82 (d, 2H, $^3$J=8.6 Hz, H-3" and H-5"); 7.10 (d, 2H, $^3$J=8.5 Hz, H-2" and H-6"); 7.32 (d, 1H, $^3$J=1.5 Hz, H-4'); 7.34 (s, 1H, H-8); 8.01 (d, 1H, $^3$J=2.3 Hz, H-5'); 8.20 (d, 1H, $^3$J=9.8 Hz, H-4).

$^{13}$C-NMR (DMSO-$d_6$, 75 MHz): δ/ppm (TMS)=15.82 (—CH$_3$); 22.01 (5-O—CH$_2$CH$_2$CH$_2$CH$_2$CH$_2$—O—C$_6$H$_4$—C$_2$H$_5$); 27.21 (—CH$_2$CH$_3$); 28.33 and 29.00 (5-O—CH$_2$CH$_2$CH$_2$CH$_2$CH$_2$—O—C$_6$H$_4$—C$_2$H$_5$); 67.12 and 72.46 (5-O—CH$_2$CH$_2$CH$_2$CH$_2$CH$_2$—O—C$_6$H$_4$—C$_2$H$_5$); 93.15 (C-8); 105.53 (C-4'); 106.00 (C-4a); 112.26 (C-3); 112.97 (C-6); 114.19 (C-3" and C-5"); 128.50 (C-2" and C-6"); 135.49 (C-4"); 139.34 (C-4); 145.84 (C-5'); 148.71 (C-5); 152.07 (C-8a); 156.63 (C-1"); 157.58 (C-7); 160.03 (C-2).

IR (KBr): ν/cm$^{-1}$=3150, 2933, 2866, 1721, 1626, 1511, 1458, 1344, 1241.

MS (EI): m/z (%)=392 M$^+$ (13), 191 [$C_{13}H_{19}O$]$^+$ (52), 135 [CH$_3$—CH$_2$C$_6$H$_4$O—CH$_2$]$^+$ (45), 107 [$C_8H_{11}$]$^+$ (24), 69 [$C_5H_9$]$^+$ (100), 41 [$C_3H_5$]$^+$ (48).

Example 44

5-[5-(4-Fluorphenoxy)pentoxy]psoralen (AS128)

4-[5-(4-Fluorphenoxy)pentoxy]-7H-furo[3,2-g][1]benzopyran-7-on

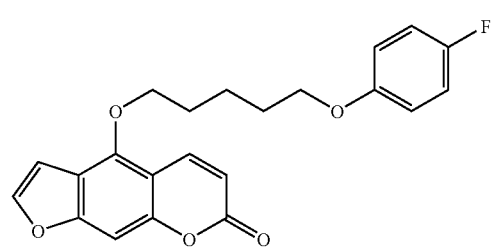

Melting point: 109° C.
Combustion analysis: $C_{22}H_{19}FO_5$ (382.39)

| | | | | |
|---|---|---|---|---|
| calculated: | C | 69.10 | H | 5.01 |
| found: | C | 69.47 | H | 5.14 |

$^1$H-NMR (DMSO-$d_6$, 300 MHz): δ/ppm (TMS)=1.60-1.66 (m, 2H, 5-O—CH$_2$CH$_2$CH$_2$CH$_2$CH$_2$—O—C$_6$H$_4$—F); 1.76-1.91 (m, 4H, 5-O—CH$_2$CH$_2$CH$_2$CH$_2$CH$_2$—O—C$_6$H$_4$—F); 3.96 (t, 2H, $^3$J=6.2 Hz, 5-O—CH$_2$CH$_2$CH$_2$CH$_2$CH$_2$—O—C$_6$H$_4$—F); 4.50 (t, 2H, $^3$J=6.2 Hz, 5-O—CH$_2$CH$_2$CH$_2$CH$_2$CH$_2$—O—C$_6$H$_4$—F); 6.29 (d, 1H, $^3$J=9.8 Hz, H-3); 6.89-6.95 (m, 2H, 5-O—CH$_2$CH$_2$CH$_2$CH$_2$CH$_2$—O—C$_6$H$_4$—F); 7.04-7.12 (m, 2H, 5-O—CH$_2$CH$_2$CH$_2$CH$_2$CH$_2$—O—C$_6$H$_4$—F); 7.29 (d, 1H, $^3$J=2.3 Hz, H-4'); 7.31 (s, 1H, H-8); 8.01 (d, 1H, $^3$J=2.3 Hz, H-5'); 8.17 (d, 1H, $^3$J=9.8 Hz, H-4).

$^{13}$C-NMR (DMSO-$d_6$, 75 MHz): δ/ppm (TMS)=21.97 (5-O—CH$_2$CH$_2$CH$_2$CH$_2$CH$_2$—O—C$_6$H$_4$—F); 28.27 and 28.99 (5-O—CH$_2$CH$_2$CH$_2$CH$_2$CH$_2$—O—C$_6$H$_4$—F); 67.78 and 72.44 (5-O—CH$_2$CH$_2$CH$_2$CH$_2$CH$_2$—O—C$_6$H$_4$—F); 93.15 (C-8); 105.53 (C-4'); 105.99 (C-4a); 112.27 (C-3); 112.96 (C-6); 115.49, 115.52, 115.59 and 115.83 (C-2'', C-3'', C-5'' and C-6''); 139.33 (C-4); 145.84 (C-5'); 148.70 (C-5); 152.06 (C-8a); 154.77 (C-4''); 157.58 (C-7); 157.89 (C-1''); 160.03 (C-2).

IR (KBr): ν/cm$^{-1}$=3136, 2944, 2872, 1720, 1626, 1504, 1452, 1351, 1134.

MS (EI): m/z (%)=382 M$^+$ (8), 202 [C$_{11}$H$_6$O$_4$]$^+$ (21), 181 [C$_{12}$H$_{16}$OF]$^+$ (37), 125 [F—C$_6$H$_4$O—CH$_2$]$^+$ (30), 69 [C$_5$H$_9$]$^+$ (100), 41 [C$_3$H$_5$]$^+$ (42).

Example 45

5-[5-(1-Naphthyloxy)pentoxy]psoralen (AS136)

4-[5-(1-Naphthyloxy)pentoxy]-7H-furo[3,2-g][1]benzopyran-7-on

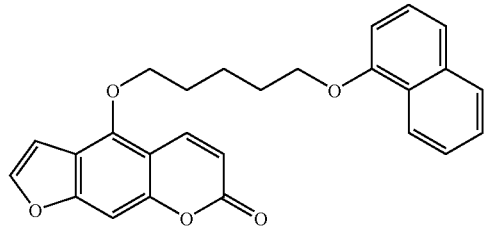

Melting point: 103° C.
Combustion analysis: C$_{26}$H$_{22}$O$_5$ (414.46)

| calculated: | C | 75.35 | H | 5.35 |
| found: | C | 75.56 | H | 5.43 |

$^1$H-NMR (DMSO-$d_6$, 300 MHz): δ/ppm (TMS)=1.71-1.81 (m, 2H, 5-O—CH$_2$CH$_2$CH$_2$CH$_2$CH$_2$—O—C$_{10}$H$_7$); 1.89-2.00 (m, 1H, 5-O—CH$_2$CH$_2$CH$_2$CH$_2$CH$_2$—O—C$_{10}$H$_7$); 4.18 (t, 2H, $^3$J=6.1 Hz, 5-O—CH$_2$CH$_2$CH$_2$CH$_2$CH$_2$—O—C$_{10}$H$_7$); 4.54 (t, 2H, $^3$J=6.0 Hz, 5-O—CH$_2$CH$_2$CH$_2$CH$_2$CH$_2$—O—C$_{10}$H$_7$); 6.21 (d, 1H, $^3$J=9.8 Hz, H-3); 6.94 (d, 1H, $^3$J=7.2 Hz, H-2''); 7.30 (s, 2H, H-8 and H-4'); 7.36-7.53 (m, 4H, 5-O—CH$_2$CH$_2$CH$_2$CH$_2$CH$_{12}$—O—C$_{10}$H$_7$); 7.84 (d, 1H, $^3$J=7.7 Hz, H-5''); 8.00 (d, 1H, $^3$J=2.2 Hz, H-5'); 8.14 (d, 1H, $^3$J=8.0 Hz, H-8''); 8.16 (d, 1H, $^3$J=9.8 Hz, H-4).

$^{13}$C-NMR (DMSO-$d_6$, 75 MHz): δ/ppm (TMS)=22.23 (5-O—CH$_2$CH$_2$CH$_2$CH$_2$CH$_2$—O—C$_{10}$H$_7$); 28.33 and 29.05 (5-O—CH$_2$CH$_2$CH$_2$CH$_2$CH$_2$—O—C$_{10}$H$_7$); 67.48 and 72.43 (5-O—CH$_2$CH$_2$CH$_2$CH$_2$CH$_2$—O—C$_{10}$H$_7$); 93.12 (C-8); 105.01 (C-2''); 105.57 (C-4'); 105.93 (C-4a); 112.20 (C-3); 112.89 (C-6); 119.69 (C-4''); 121.35 (C-8''); 124.91, 125.08, 126.17, 126.30 and 127.39 (C-3'', C-5'', C-6'', C-7'' and C-8a''); 133.97 (C-4a''); 139.30 (C-4); 145.82 (C-5'); 148.73 (C-5); 152.07 (C-8a); 154.02 (C-1''); 157.60 (C-7); 160.02 (C-2).

IR (KBr): ν/cm$^{-1}$=2946, 2870, 1733, 1591, 1458, 1345.

MS (EI): m/z (%)=414 M$^+$ (82), 271 (28), 213 [C$_{15}$H$_{17}$O]$^+$ (54), 144 (58), 115 (36), 69 [C$_5$H$_9$]$^+$ (100), 41 [C$_3$H$_5$]$^+$ (85).

Example 46

5-[5-(2-Naphthyloxy)pentoxy]psoralen (AS134)

4-[5-(2-Naphthyloxy)pentoxy]-7H-furo[3,2-g][1]benzopyran-7-on

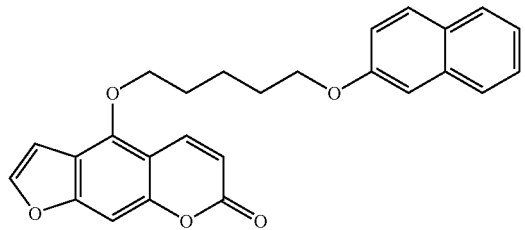

Melting point: 118° C.
Combustion analysis: O$_{26}$H$_{22}$O$_5$ (414.46)

| calculated: | C | 75.35 | H | 5.35 |
| found: | C | 75.00 | H | 5.52 |

$^1$H-NMR (DMSO-$d_6$, 300 MHz): δ/ppm (TMS)=1.66-1.75 (m, 2H, 5-O—CH$_2$CH$_2$CH$_2$CH$_2$CH$_2$—O—C$_{10}$H$_7$); 1.84-1.96 (m, 1H, 5-O—CH$_2$CH$_2$CH$_2$CH$_2$CH$_2$—O—C$_{10}$H$_7$); 4.14 (t, 2H, $^3$J=6.3 Hz, 5-O—CH$_2$CH$_2$CH$_2$CH$_2$CH$_2$—O—C$_{10}$H$_7$); 4.53 (t, 2H, $^3$J=6.1 Hz, 5-O—CH$_2$CH$_2$CH$_2$CH$_2$CH$_2$—O—C$_{10}$H$_7$); 6.31 (d, 1H, $^3$J=9.8 Hz, H-3); 7.15 (dd, 1H, $^3$J=8.9 Hz, $^4$J=2.4 Hz, H-3''); 7.31-7.36 (m, 4H, H-8, H-4' and 5-O—CH$_2$CH$_2$CH$_2$CH$_2$CH$_2$—O—C$_{10}$H$_7$); 7.45 (t, 1H, $^3$J=7.2 Hz, H-7''); 7.77-7.82 (m, 3H, 5-O—CH$_2$CH$_2$CH$_2$CH$_2$CH$_2$—O—C$_{10}$H$_7$); 8.02 (d, 1H, $^3$J=2.3 Hz, H-5'); 8.20 (d, 1H, $^3$J=9.8 Hz, H-4).

$^{13}$C-NMR (DMSO-$d_6$, 75 MHz): δ/ppm (TMS)=22.05 (5-O—CH$_2$CH$_2$CH$_2$CH$_2$CH$_2$—O—C$_{10}$H$_7$); 28.26 and 29.02 (5-O—CH$_2$CH$_2$CH$_2$CH$_2$CH$_2$—O—C$_{10}$H$_7$); 67.29 and 72.47 (5-O—CH$_2$CH$_2$CH$_2$CH$_2$CH$_2$—O—C$_{10}$H$_7$); 93.17 (C-8); 105.54 (C-4'); 106.02 (C-4a); 106.60 (C-1''); 112.28 (C-3); 112.99 (C-6); 118.62 (C-3''); 123.39 (C-6''); 126.26, 126.55, 127.41, 128.35 and 129.16 (C-4'', C-4a'', C-5'', C-7'' and C-8''); 134.25 (C-8a''); 139.35 (C-4); 145.85 (C-5'); 148.72 (C-5); 152.07 (C-8a); 156.48 (C-2''); 157.58 (C-7); 160.03 (C-2).

IR (KBr): ν/cm$^{-1}$=3155, 3087, 2949, 2864, 1716, 1626, 1546, 1342, 1259.

MS (EI): m/z (%)=414 M$^+$ (20), 271 (3), 213 [C$_{15}$H$_{17}$O]$^+$ (45), 202 [C$_{11}$H$_6$O$_4$]$^+$ (13), 157 (45), 127 (31), 69 [C$_5$H$_9$]$^+$ (100), 41 [C$_3$H$_5$]$^+$ (62)

Example 47

5-{4-(1-N-Pyrazolyl)butoxy}psoralen (PH 1)

4-{4-(1-N-Pyrazolyl)butoxy}-7H-furo[3,2-g][1]benzopyran-7-on

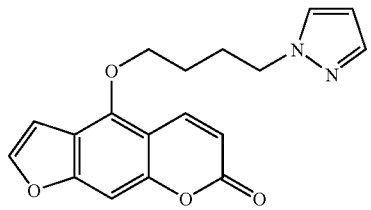

500 mg (2.473 mmol) of 5-hydroxypsoralen and 893 mg (4.088 mmol) of 4-iodo-1-chlorobutane were stirred at 25° C. in 30 ml of anhydrous acetone in the presence of an excess (2.0 g) of anhydrous potassium carbonate for 28 hours. The progress of the reaction was monitored by thin layer chromatography. After 28 hours the reaction mixture was concentrated under reduced pressure and distilled off the solvent almost completely. The oily residue was cooled and diluted with water. The aqueous solution was then acidified with concentrated hydrochloric acid to pH 1. The slurry was stirred for 15-20 min and filtered. The solids were washed with water to neutral pH and dried. The dried solids were suspended in petroleum ether, filtered and dried under vacuum. To the solids were added 400 mg (5.875 mmol) of pyrazole, 2.0 g anhydrous potassium carbonate, catalytic amounts of potassium iodide, 30 ml of 2-butanone and the reaction mixture was refluxed for 50 hours. After 50 hours the reaction mixture was concentrated under vacuum. The residue was diluted with water and acidified to pH 1 with concentrated hydrochloric acid. The separated oily organic layer was extracted with 3×50 ml of dichloromethane. The dichloromethane layer was then washed with 0.75% aqueous sodium hydroxide to separate the un-reacted 5-hydroxypsoralen followed by washing with acidic water. The dichloromethane layer was dried over anhydrous sodium sulfate and concentrated. The residue was dissolved in an acetone-methanol mixture, treated with charcoal and re-crystallized from an ethyl acetate-petroleum ether (20:80) mixture.

Yield: 108.6 mg (13.54%)

Melting point: 145.6° C.

$^1$H-NMR (500 MHz, DMSO-$d_6$): δ [ppm]=8.17 (d, 1H, $^3$J=9.1 Hz, 3-H), 8.02 (s, 1H, 2'-H), 7.74 (s, 1H, 5-OCH$_2$CH$_2$CH$_2$CH$_2$C$_3$H$_3$N$_2$), 7.43 (s, 1H, 5-OCH$_2$CH$_2$CH$_2$CH$_2$—$\overline{C_3H_3N_2}$), 7.34 (s, 1H, 8-H), 7.29 (s, 1H, 3'-H), 6.32 (d, 1H, $^3$J=9.1 Hz, 4-H), 4.47 (s, 2H, 5-OCH$_2$CH$_2$CH$_2$CH$_2$C$_3$H$_3$N$_2$), 4.20 (s, 2H, 5-OCH$_2$CH$_2$CH$_2$C$\overline{H_2}$C$_3$H$_3$N$_2$), 2.0 (s, 2H, OCH$_2$CH$_2$CH$_2$CH$_2$C$_3$H$_3$N$_2$), 1.75 (s, 2H, 5-OCH$_2$CH$_2$CH$_2$CH$_2$C$_3$H$_3$$\overline{N_2}$).

MS (70 eV) m/z: 324 (29%, M$^+$), 202 (6%, [M-C$_{10}$H$_{12}$O]$^+$), 174 (6%, [202-CO]$^+$), 123 (99%), 81 (26%), 69 (13%).

Combustion analysis: (FW: 324.34) % C, 65.83; % H, 4.96; % N, 7.36

(Calc. % C, 66.66; % H, 4.97; % N, 8.64)

Example 48

5-{4-N-(4-Pyridinyl)aminobutoxy}psoralen (PH 3)

4-{4-(4-N-Pyridinyl)aminobutoxy}-7H-furo[3,2-g][1]benzopyran-7-on

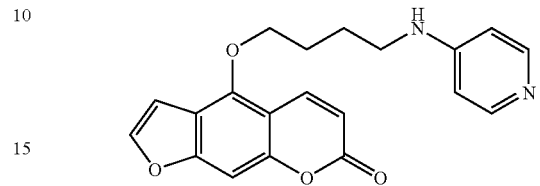

390 mg (1.334 mmol) of 5-(4-chlorobutoxy)psoralen and 628 mg (6.67 mmol) of 4-aminopyridine were refluxed in 20 ml of anhydrous acetonitrile in the presence of catalytic amounts of potassium iodide for 45 hours. The progress of the reaction was monitored by thin layer chromatography. After 45 hours the reaction mixture was concentrated under reduced pressure. The oily residue was cooled, diluted with water and acidified with 10% aqueous hydrochloric acid to pH 7-7.5. The slurry was stirred for 15-20 min and filtered. The solids were dissolved in methanol, treated with charcoal and re-crystallized from 2% acidic acetone.

Yield: 171.5 mg (30.37%)

Melting point: 133.9° C.

$^1$H-NMR (500 MHz, DMSO-$d_6$): δ [ppm]=8.272 (s, 1H, 5-OCH$_2$CH$_2$CH$_2$CH$_2$NHC$_5$H$_4$N), 8.25 (d, 2H, $^3$J=7.41 Hz, 5-OCH$_2$CH$_2$CH$_2$CH$_2$N$\overline{H}$C$_5$H$_4$N), 8.18 (d, 1H, $^3$J=9.8 Hz, 3-H), 8.05 (d, 1H, $^3$J=2.6 Hz, $\overline{2}$'-H), 7.36 (s, 1H, 8-H), 7.33 (d, 1H, $^3$J=2.3 Hz, 3'-H), 6.85 (d, 2H, $^3$J=7.32 Hz, 5-OCH$_2$CH$_2$CH$_2$CH$_2$NHC$_5$H$_4$N), 6.32 (d, 1H, $^3$J=9.8 Hz, 4-H), 4.514 (t, 2$\overline{H}$, $^3$J=6.06 Hz, 5-OCH$_2$CH$_2$CH$_2$CH$_2$NHC$_5$H$_4$N), 4.22 (t, 2H, $^3$J=6.98 Hz, $\overline{5}$-OCH$_2$CH$_2$CH$_2$CH$_2$NHC$_5$H$_4$N), 1.99 (p, 2H, 5-OCH$_2$CH$_2$CH$_2$CH$_2$NHC$_5$$\overline{H_4}$N), 1.77 (p, 2H, 5-OCH$_2$CH$_2$C$\overline{H_2}$CH$_2$NHC$_5$H$_4$N).

MS (70 eV) m/z: 350 (12%, M$^+$), 202 (99%, [M-C$_9$H$_{12}$N$_2$]$^+$), 174 (60%, [202-CO]$^+$), 184 (20%), 145 (11%), 123 (15%), 107 (46%), 94 (7%, C$_5$H$_6$N$_2$).

Combustion analysis: (FW: 423.38) % C, 56.69; % H, 4.94; % N, 6.38

(Calc. % C, 56.68; % H, 4.72; % N, 6.61)

Example 49

5-{4-(5"-Methyl-1",3",4"-thiadiazol-2"-thiolyl)butoxy}psoralen(PH 4)

4-{4-(5"-Methyl-1",3",4"-thiadiazol-2"-thiolyl)butoxy}-7H-furo[3,2-g][1]benzopyran-7-on

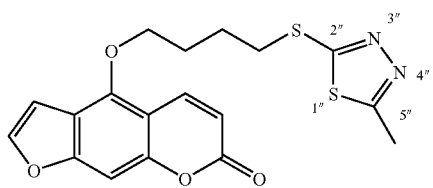

500 mg (1.708 mmol) of 5-(4-chlorobutoxy)psoralen and 361 mg (2.733 mmol) of 2-mercapto-1,3,4-thiadiazole were refluxed in 30 ml of 2-butanone in the presence of an excess of anhydrous potassium carbonate (2.0 gm) and catalytic amounts of potassium iodide for 66 hours. The progress of the reaction was monitored by thin layer chromatography. After 66 hours the reaction mixture was concentrated under reduced pressure and distilled off the solvent almost completely. The oily residue was cooled, diluted with water and acidified with concentrated hydrochloric acid to pH 1. The slurry was stirred for 15-20 min and extracted with 100 ml of dichloromethane. The dichloromethane layer was washed with 30 ml of 2% hydrochloric acid solution, dried over anhydrous sodium sulfate and concentrated. The oily residue obtained was dissolved in methanol, treated with charcoal and re-crystallized from a petroleum ether-ethyl acetate (80:20) mixture.

Yield: 107 mg (16.13%)
Melting point: 92.1° C.
$^1$H-NMR (500 MHz, CDCl$_3$): δ [ppm]=8.15 (d, 1H, $^3$J=9.79 Hz, 3-H), 7.59 (d, 1H, $^3$J=2.48 Hz, 2'-H), 7.16 (s, 1H, 8-H), 6.95 (d, 1H, $^3$J=2.45 Hz, 3'-H), 6.29 (d, 1H, $^3$J=9.76 Hz, 4-H), 4.51 (t, 2H, $^3$J=5.81 Hz, 5-OCH$_2$CH$_2$CH$_2$CH$_2$S—), 3.43 (t, 2H, $^3$J=6.88 Hz, 5-OCH$_2$CH$_2$CH$_2$CH$_2$S—), 2.74 (s, 3H, 5"-CH$_3$), 2.09 (m, 4H, $^3$J=3.00 Hz, 5-OCH$_2$CH$_2$CH$_2$CH$_2$S—).

MS (70 eV) m/z: 388 (62%, M$^+$), 202 (14%, [M-C$_7$H$_{10}$N$_2$S$_2$]$^+$), 187 (96%, C$_7$H$_{11}$N$_2$S$_2$), 174 (12%, [202-CO]$^+$), 145 (10%), 133 (32%), 99 (34%, C$_3$H$_3$N$_2$S), 87 (8%, C$_4$H$_7$S), 55 (28%, C$_4$H$_7$).

Combustion analysis: (FW: 388.47) % C, 53.44; % H, 4.45; % N, 7.59; % S, 16.77
(Calc. % C, 55.65; % H, 4.15; % N, 7.21; % S, 16.51)

Example 50

5-{4-(7-Coumarinyloxy)butoxy}psoralen (PH 5)

4-{4-(7-Coumarinyloxy)butoxy}-7H-furo[3,2-g][1]benzopyran-7-on

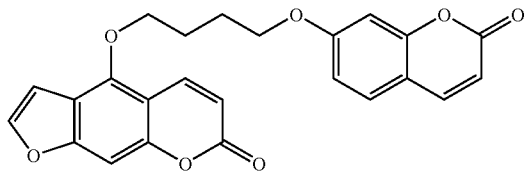

500 mg (1.708 mmol) of 5-(4-chlorobutoxy)psoralen and 443 mg (2.733 mmol) of 7-hydroxycoumarin were refluxed in 30 ml of 2-butanone in the presence of an excess of anhydrous potassium carbonate (2.0 g) and catalytic amounts of potassium iodide for 68 hours. The progress of the reaction was monitored by thin layer chromatography. After 68 hours the reaction mixture was concentrated under reduced pressure. The oily residue was cooled, diluted with water and acidified with concentrated hydrochloric acid to pH 1. The slurry was stirred for 15-20 min and extracted with 3×50 ml of dichloromethane. The dichloromethane layer was extracted with 3×25 ml of 1% sodium hydroxide to separate the un-reacted 7-hydroxycoumarin. The dichloromethane layer was washed with 30 ml of 2% hydrochloric acid, dried over anhydrous sodium sulfate and concentrated. The resulting oily residue was dissolved in methanol, treated with charcoal and re-crystallized from a methanol-acetone (70:30) mixture.

Yield: 134.0 mg (18.75%)
Melting point: 147° C.
$^1$H-NMR (500 MHz, CDCl$_3$): δ [ppm]=8.15 (d, 1H, $^3$J=9.80 Hz, 3-H), 7.64 (d, 1H, $^3$J=9.5 Hz, 5-OCH$_2$CH$_2$CH$_2$CH$_2$OC$_9$H$_5$O$_2$), 7.61 (d, 1H, $^3$J=2.1 Hz, 2'-H), 7.36 (dd, 1H, $^3$J=8.6 Hz, $^5$J=2.5 Hz, 5-OCH$_2$CH$_2$CH$_2$CH$_2$OC$_9$H$_5$O$_2$), 7.16 (s, 1H, 8-H), 6.99 (d, 1H, $^3$J=2.1 Hz, 3'-H), 6.83 (m, 2H, 5-OCH$_2$CH$_2$CH$_2$OC$_9$H$_5$O$_2$), 6.26 (d, 1H, $^3$J=9.50 Hz, 4-H), 6.20 (d, 1H, $^3$J=9.8 Hz, 5-OCH$_2$CH$_2$CH$_2$CH$_2$OC$_9$H$_5$O$_2$), 4.57 (t, 2H, $^3$J=5.4 Hz, 5-OCH$_2$CH$_2$CH$_2$CH$_2$OC$_9$H$_5$O$_2$), 4.15 (t, 2H, $^3$J=5.0 Hz, 5-OCH$_2$CH$_2$CH$_2$CH$_2$OC$_9$H$_5$O$_2$), 2.11 (m, 4H, $^3$J=2.6 Hz, 5-OCH$_2$CH$_2$CH$_2$CH$_2$OC$_9$H$_5$O$_2$).

MS (70 eV) m/z: 418 (34%, M$^+$), 378 (68%), 217 (89%), 202 (20%, [M-C$_{13}$H$_{12}$O$_3$]$^+$), 175 (100%), 174 (14%, [202-CO]$^+$), 187 (16%), 145 (32%), 134 (26%), 89 (30%), 55 (48%, C$_4$H$_7$)

Combustion analysis: (FW: 418.41) % C, 69.08; % H, 4.46. (Calc. % C, 68.9.0; % H, 4.34)

Example 51

5-{4(5-Methoxy-1,3-benzothiazol-2-thiolyl)butoxy}psoralen(PH 8)

4-{4-(5-Methoxy-1,3-benzothiazol-2-thiolyl)butoxy}-7H-furo[3,2-g][1]benzopyran-7-on

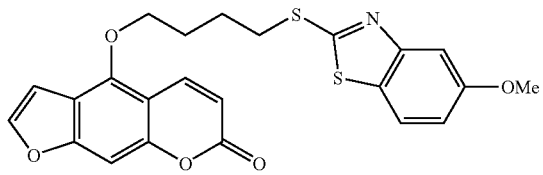

539 mg (2.733 mmol) of 2-mercapto-5-methoxy-1,3-benzothiazole and 161 mg (2.869 mmol) of potassium hydroxide were refluxed in 25 ml of methanol until a clear solution was obtained. The solution was concentrated to dryness under vacuum. To the solid potassium salt was added 20 ml of anhydrous acetonitrile, 500 mg (1.708 mmol) of 5-(4-chlorobutoxy)psoralen, 333 mg (2.221 mmol) of sodium iodide and the resulting mixture was refluxed for 69 hours. The progress of the reaction was monitored by thin layer chromatography. After 69 hours the reaction mixture was concentrated under reduced pressure. The oily residue was cooled, diluted with water and acidified with concentrated hydrochloric acid to pH 1. The slurry was stirred for 15-20 min and extracted with 100 ml of dichloromethane. The dichloromethane layer was washed with 30 ml of 1% sodium hydroxide to separate the un-reacted 2-mercaptobenzothiazole followed by 30 ml of 2% hydrochloric acid, dried over anhydrous sodium sulfate and concentrated. The resulting oily residue was dissolved in methanol, treated with charcoal and re-crystallized from a petroleum ether-acetone (80:20) mixture.

Yield: 599.8 mg (77.09%)
Melting point: 134.8° C.
$^1$H-NMR (500 MHz, CDCl$_3$): δ [ppm]=8.09 (d, 1H, $^3$J=9.76 Hz, 3-H), 7.61 (d, 1H, $^3$J=8.9 Hz benzothiazole), 7.58 (d, 1H, $^3$J=2.24 Hz, 2'-H), 7.35 (d, 1H, $^4$J=2.2 Hz, benzothiazole), 7.14 (s, 1H, 8-H), 6.97 (dd, 1H, $^3$J=8.9 Hz, $^4$J=2.1 Hz, benzothiazole), 6.95 (d, 1H, $^3J$=2.76 Hz, 3'-H), 6.18 (d, 1H, $^3J$=9.78 Hz, 4-H), 4.53 (t, 2H, $^3J$=5.78 Hz, 5-OCH$_2$CH$_2$CH$_2$CH$_2$S—), 3.87 (s, 3H, O—CH$_3$), 3.48 (t, 2H, $^3J$=6.61 Hz, 5-OCH$_2$CH$_2$CH$_2$CH$_2$S—), 2.11 (m, 4H, 5-OCH$_2$CH$_2$CH$_2$CH$_2$S—).

MS (70 eV) m/z: 455 (6%, M$^+$), 453 (44%), 328 (28%), 252 (100%, C$_{12}$H$_{14}$NOS$_2$), 201 (6%), 196 (12%, C$_8$H$_6$NOS$_2$), 174 (14%, [202-CO]$^+$), 145 (8%), 89 (6%), 55 (28%, C$_4$H$_7$).

Combustion analysis: (FW: 455.56) % C, 60.70; % H, 4.49; % N, 3.09; % S, 13.94

(Calc. % C, 60.70; % H, 4.65; % N, 3.07; % S, 14.08

Example 52

5-{4-(Pyrimidin-2-thiolyl)butoxy}psoralen(PH 9)

4-{4-(Pyrimidin-2-thiolyl)butoxy}-7H-furo[3,2-g][1]benzopyran-7-on

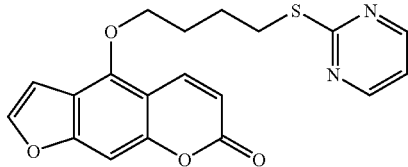

306 mg (2.733 mmol) of 2-mercaptopyrimidine and 163 mg (2.87 mmol) of potassium hydroxide were refluxed in 50 ml methanol until a clear solution was obtained. The solution was concentrated to dryness under reduced pressure. To the solid potassium salt was then added 30 ml of anhydrous acetonitrile, 500 mg (1.708 mmol) of 5-(4-chlorobutoxy)psoralen, 333 mg (2.220 mmol) of sodium iodide and the resulting mixture was refluxed for 67 hours. The progress of the reaction was monitored by thin layer chromatography. After 67 hours the reaction mixture was concentrated under reduced pressure and distilled off the solvent almost completely. The oily residue was cooled and diluted with water and then acidified with concentrated hydrochloric acid to pH 1. The slurry was stirred for 15-20 min and extracted with 100 ml of dichloromethane. The dichloromethane layer was washed with 30 ml of 1% sodium hydroxide to separate the un-reacted 2-mercaptopyrimidine followed by 30 ml of 2% hydrochloric acid, dried over anhydrous sodium sulfate and concentrated. The oily residue was dissolved in methanol, treated with charcoal and re-crystallized from methanol.

Yield: 244 mg (38.78%)

Melting point: 107-107.1° C.

$^1$H-NMR (500 MHz, CDCl$_3$): δ [ppm]=8.51 (d, 2H, pyrimidine), 8.14 (d, 1H, $^3J$=10.1 Hz, 3-H), 7.59 (d, 1H, $^3J$=2.4 Hz, 2'-H), 7.16 (s, 1H, 8-H), 7.0 (t, 1H, $^3J$=4.89 Hz, pyrimidine), 6.96 (d, 1H, $^3J$=1.5 Hz, 3'-H), 6.25 (d, 1H, $^3J$=9.8 Hz, 4-H), 4.52 (t, 2H, $^3J$=5.8 Hz, 5-OCH$_2$CH$_2$CH$_2$CH$_2$S—), 3.29 (t, 2H, $^3J$=6.8 Hz, 5-OCH$_2$CH$_2$CH$_2$CH$_2$S—), 2.01 (m, 4H, 5-OCH$_2$CH$_2$CH$_2$CH$_2$S—).

MS (70 eV) m/z: 368 (27%, M$^+$), 202 (8%, M-C$_8$H$_{10}$N$_2$S), 167 (100%, C$_8$H$_{11}$N$_2$S), 125 (34%), 113 (37%), 55 (26%, C$_4$H$_7$).

Combustion analysis: (FW: 368.41) % C, 61.55; % H, 4.24; % N, 7.41; % S, 8.46

(Calc. % C, 61.94; % H, 4.38; % N, 7.60; % S, 8.70)

Example 53

5-(3-Cyanopropoxy)psoralen [ACP 1]

4-(3-Cyanopropoxy)-7H-furo[3,2-g][1]benzopyran-7-on

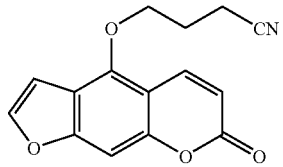

800 mg (3.956 mmol) of 5-hydroxypsoralen and 0.7 ml (655.5 mg, 6.33 mmol) of 4-chlorobutyronitrile were refluxed in 50 ml of 2-butanone in the presence of an excess (2.6 g) of anhydrous potassium carbonate and catalytic amounts of potassium iodide for 48 hours. The progress of the reaction was monitored by thin layer chromatography. After 48 hours the reaction mixture was concentrated under reduced pressure. The residual oily layer was cooled, diluted with water and acidified with concentrated hydrochloric acid to pH 1. The slurry was stirred for 15-20 min and then filtered. The solids were washed with water to neutral pH, dried by suction and then further washed with petroleum ether. The dried solids were dissolved in refluxing methanol, treated with charcoal and recrystallized from methanol.

Yield: 710.2 mg (66.67%)

Melting point: 155.2° C.

$^1$H-NMR (500 MHz, CDCl$_3$): δ [ppm]=8.13 (d, 1H, $^3J$=9.8 Hz, 3-H), 7.63 (d, 1H, $^3J$=2.0 Hz, 2'-H), 7.21 (s, 1H, 8-H), 6.98 (d, 1H, $^3J$=2.0 Hz, 3'-H), 6.32 (d, 1H, $^3J$=9.5 Hz, 4-H), 4.58 (t, 2H, $^3J$=5.8 Hz, 5-OCH$_2$CH$_2$CH$_2$CN), 2.72 (t, 2H, $^3J$=5.7 Hz, 5-OCH$_2$CH$_2$CH$_2$CN), 2.26 (p, 2H, $^3J$=6.3 Hz, 5-OCH$_2$CH$_2$CH$_2$CN).

MS (70 eV) ink: 269 (100%, M$^+$), 202 (74%, [M-C$_4$H$_5$N]$^+$), 174 (63%, [202-CO]$^+$), 145 (26%), 118 (7%), 89 (14%).

Combustion analysis: (FW: 269.26) % C, 66.52; % H, 4.03; % N, 5.01

(Calc. % C, 66.91; % H, 4.12; % N, 5.01)

Example 54

5-(4-Phenyl-3-oxobutoxy)psoralen (KP 1)

4-(4-Phenyl-3-oxobutoxy)-7H-furo[3,2-g][1]benzopyran-7-on

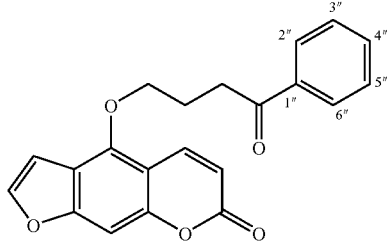

497 mg (2.720 mmol) of 4-chlorobutyrophenone and 445 mg (2.968 mmol) of sodium iodide were refluxed in 30 ml acetone for 1.5 hours to obtain the iodo derivative. The reaction was monitored by TLC and also visually by the precipitation of sodium chloride. To this slurry was added 500 mg (2.473 mmol) of 5-hydroxypsoralen, an excess (2 g) of anhydrous potassium carbonate and it was refluxed for 140 hours. The progress of the reaction was monitored by thin layer chromatography. After 140 hours the reaction mixture was concentrated under reduced pressure. The oily residue was cooled and diluted with water. The aqueous solution was then acidified with concentrated hydrochloric acid to pH 1. The slurry was stirred for 15-20 min, filtered and washed with water and dried under vacuum. The solids were suspended in 50 ml ethyl acetate and refluxed to separate the un-reacted 5-hydroxypsoralen. The ethyl acetate layer was concentrated, the resulting residue dissolved in 100 ml dichloromethane and extracted with 25 ml of 1% sodium hydroxide to separate the remaining trace amounts of un-reacted 5-hydroxypsoralen. The dichloromethane layer was washed with 30 ml of 2% hydrochloric acid solution, dried over anhydrous sodium sulfate and concentrated. The solid residue obtained was dissolved in a methanol-acetone mixture, treated with charcoal and re-crystallized from a petroleum ether-acetone (90:10) mixture.

Yield: 295.2 mg (34.27%)

Melting point: 129.1° C.

$^1$H-NMR (500 MHz, CDCl$_3$): δ [ppm]=8.13 (d, 1H, $^3$J=9.9 Hz, 3-H), 8.01 (d, 2H, $^3$J=7.9 Hz, $^4$J=0.95 Hz, 2''-H, 6''-H), 7.62 (t, 1H, $^3$J=7.4 Hz, 3''-H, 5''-H), 7.60 (d, 1H, $^3$J=2.4 Hz, 2'-H), 7.50 (t, 2H, $^3$J=7.7 Hz, 4''-H), 7.15 (s, 1H, 8-H), 6.99 (d, 1H, $^3$J=2.5 Hz, 3'-H), 6.26 (d, 1H, $^3$J=9.8 Hz, 4-H) 4.59 (t, 2H, $^3$J=6.2 Hz, 5-OCH$_2$CH$_2$CH$_2$COC$_6$H$_5$), 3.28 (t, 2H, $^3$J=6.8 Hz, 5-OCH$_2$CH$_2$CH$_2$COC$_6$H$_5$), 2.38 (p, 2H, $^3$J=6.5 Hz, 5-OCH$_2$CH$_2$CH$_2$COC$_6$H$_5$).

MS (70 eV) m/z: 348 (34%, M$^+$), 202 (5%, M$^+$-C$_{10}$H$_{10}$O), 147(99%, C$_{10}$H$_{10}$O) 174, (5%, [202-CO]$^+$), 105 (71%, C$_3$H$_6$), 77 (33%, C$_6$H$_5$).

Combustion analysis: (FW: 348.36) % C, 71.68; % H, 5.25 (Calc. % C, 72.41; % H, 4.63)

Example 55

5-(4-Pentynyloxy)psoralen (AP1)

4-(4-Pentynyloxy)-7H-furo[3,2-g][1]benzopyran-7-on

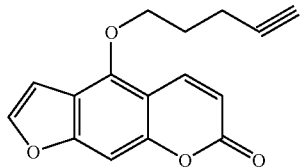

500 mg (2.473 mmol) of 5-hydroxypsoralen and 405.85 mg (3.957 mmol) of 5-chloro-1-pentyne were refluxed in 30 ml of acetonitrile in the presence of an excess of anhydrous potassium carbonate (2.0 gm) and catalytic amounts of potassium iodide for 24 hours. The progress of the reaction was monitored by thin layer chromatography. After 24 hours the reaction mixture was concentrated under reduced pressure. The oily residue was cooled, diluted with water and acidified with concentrated hydrochloric acid to pH 1. The aqueous phase was extracted with dichloromethane. The dichloromethane phase was extracted with 25 ml of 1% sodium hydroxide to separate the un-reacted 5-hydroxypsoralen. The dichloromethane phase was washed with acidic water and then with water to pH~6-7. The organic phase was then dried over anhydrous sodium sulphate and concentrated to dryness. The residue was dissolved in methanol, decolorized with charcoal and re-crystallized from methanol.

Yield: 55 mg (8.29%)

Melting point: 144.9-145.1° C.

$^1$H-NMR (500 MHz, CDCl$_3$): δ [ppm]=8.16 (d, 1H, $^3$J=9.77 Hz, 3-H), 7.60 (d, 1H, $^3$J=2.32 Hz, 2'-H), 7.17 (s, 1H, 8-H), 7.01 (d, 1H, $^3$J=1.53 Hz, 3'-H), 6.29 (d, 1H, $^3$J=9.78 Hz, 4-H), 4.56 (t, 2H, $^3$J=6.06 Hz, 5-OCH$_2$CH$_2$CH$_2$CCH), 2.51 (q, 2H, $^3$J=2.55 Hz, 5-OCH$_2$CH$_2$CH$_2$CCH), 2.09 (p, 2H, $^3$J=6.44 Hz, 5-OCH$_2$CH$_2$CH$_2$CCH), 2.03 (t, 1H, $^4$J=2.59 Hz, 5-OCH$_2$CH$_2$CH$_2$CCH)

MS (70 eV) m/z: 268 (88%, M$^+$), 203 (15%), 202 (100%, [M-C$_5$H$_6$]$^+$), 175 (8%), 174 (11%, [202-CO]$^+$), 173 (14%), 146 (7%), 145 (21%), 118(8%), 89 (10%), 67 (5%, C$_5$H$_7$)

Combustion analysis: (FW: 268.27) % C, 71.25; % H, 4.38 (Calc. % C, 71.64; % H, 4.51)

Example 56

5-[4-(N-Phthalimido)butoxy]psoralen (PP1)

4-[4-(N-Phthalimido)butoxy]-7H-furo[3,2-g][1]benzopyran-7-on

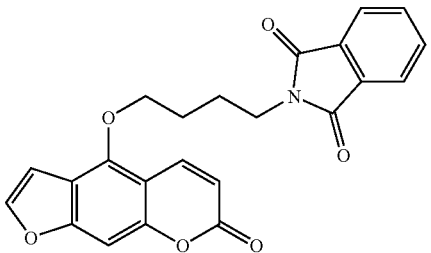

500 mg (2.473 mmol) of 5-hydroxypsoralen and 1.12 g (3.959 mmol) of N-(4-bromobutyl)phthalimide were refluxed in 50 ml of acetonitrile in the presence of an excess (2.2 g) of anhydrous potassium carbonate and catalytic amounts of potassium iodide for 72 hours. The progress of the reaction was monitored by thin layer chromatography. After 72 hours the reaction mixture was concentrated under reduced pressure. The residue was cooled and extracted with methanol. The slurry was filtered and the solids were washed with methanol. The solids were then acidified with 10% aqueous hydrochloric acid to pH~1, filtered and washed with water to neutral pH and dried under vacuum. The solids were dissolved in acetone, treated with charcoal and recrystallized from methanol.

Yield: 260 mg (26.06%)

Melting point: 177.9° C.

$^1$H-NMR (500 MHz, CDCl$_3$): δ [ppm]=8.14 (d, 1H, $^3$J=9.8 Hz, 3-H), 7.8 (dd, 4H, $^3$J=5.4 Hz, $^4$J=3.0 Hz, 5-OCH$_2$CH$_2$CH$_2$CH$_2$NC$_8$H$_4$O$_2$), 7.6 (d, 1H, $^3$J=2.4 Hz, 2'-H), 7.13 (s, 1H, 8-H), 6.95 (d, 1H, $^3$J=1.6 Hz, 3'-H), 6.30 (d, 1H, $^3$J=9.8 Hz, 4-H), 4.5 (t, 2H, $^3$J=5.7 Hz, 5-OCH$_2$CH$_2$CH$_2$CH$_2$NC$_8$H$_4$O$_2$), 3.82 (t, 2H, $^3$J=6.6 Hz, 5-OCH$_2$CH$_2$CH$_2$CH$_2$NC$_8$H$_4$O$_2$), 1.98 (p, 4H, $^3$J=3.2 Hz, 5-OCH$_2$CH$_2$CH$_2$CH$_2$NC$_8$H$_4$O$_2$).

MS (70 eV) m/z: 403 (13%, M$^i$), 202 (72%, [M-C$_{12}$H$_{11}$NO$_2$]$^+$), 202 (72%, C$_{12}$H$_{11}$NO$_2$), 174 (8%, [202-CO]$^+$), 160 (99%), 148 (6%), 130 (14%), 55 (5%, C$_4$H$_7$)

Combustion analysis: (FW: 403.40) % C, 68.17%; % H, 4.32; % N, 3.36
(Calc. % C, 68.48; % H, 4.25; % N, 3.47)

B. Data Comparing Inhibitory Activity On Different Potassium Channels

Appendix A sets forth examples of the inhibitory effects of certain 5-phenoxyalkoxypsoralen compounds of the present invention on various potassium channels. These data indicate that certain of the compounds in the present invention (especially those designated as PAP-1, AS78 and AS85 in Appendix A) are selective for Kv1.3 channels over Kv1.5 channels. As explained above, inhibition of Kv1.5 potassium channels may cause clinically significant cardiac rhythm disturbances. Thus, the selectivity of these compounds for Kv1.3 channels over Kv1.5 channels may render these compounds useable for the treatment or prevention of a broad range of T cell mediated disorders and/or other disorders that may be treated or prevented by inhibition of Kv1.3 channels, with little or no potential for cardiac arrhythmias due to untoward Kv1.5 channel inhibition.

C. Methods for Treating or Preventing Diseases or Disorders

The compositions of the present invention, as described above, and/or pharmaceutically acceptable salts or derivatives thereof, may be administered to human or animal subjects in amount(s), on dosing schedule(s) and by route(s) of administration that are effective to treat or prevent diseases or disorders by inhibiting one or more types of potassium channels. As shown in Appendix A, different compounds of the present invention exhibit different degrees of selectivity for different types of potassium channels and, thus, specific compounds may be selected on the basis of their potassium channel selectivity to treat specific diseases or disorders. Although any suitable dosage may be used, the currently available information indicates that one or more doses of about 0.1 mg/kg through about 10.0 mg/kg of a compound of General Formula I may be administered to humans to treat or prevent a disease or disorder, such as a T cell mediated disease or disorder. The route of administration may vary, depending on the particular compound being given and/or the particular disease or disorder to be treated or prevented.

Example 57

Administration of 5-(4-Phenoxybutoxy)7H-furo[3,2-q][1]benzopyran-7-on (PAP-1) for Systemic Treatment of T Cell Mediated Diseases For example, 5-(4-Phenoxybutoxy)7H-furo[3,2-g][1]benzopyran-7-on (i.e., the compound designated as PAP-1 in Example 1), or a pharmaceutically acceptable salt or derivative thereof, may be administered orally or by injection (subcutaneous, intramuscular, intravenous, etc.) to humans in one or more daily doses of about 0.1 mg/kg through about 10.0 mg/kg to systemically treat a T cell mediated autoimmune disorder. Such systemic treatment may be particularly suited for treatment of diseases and disorders such as Type-1 diabetes, MS, graft vs. host disease or transplant rejection, etc.

Example 58

Administration of 5-(4-Phenoxylbutoxy)7H-furo[3,2-g][1]benzopyran-7-on (PAP-1) for Local Treatment of T Cell Mediated Diseases For example, 5-(4-Phenoxybutoxy)7H-furo[3,2-g][1]benzopyran-7-on (i.e., the compound designated as PAP-1 in Example 1), or a pharmaceutically acceptable salt or derivative thereof, may be administered topically or by local injection (e.g., intradermal, subcutaneous, intramuscular, etc.) to humans in one or more daily doses of about 0.1 mg/kg through about 10.0 mg/kg to locally treat a T cell mediated autoimmune disorder. Such local treatment may be particular suited for T cell mediated diseases that cause cutaneous lesions, such as psoriasis, dermatitis herpetiformis, pemphigus vulgaris, mycosis fungoides, allergic contact dermatitis, atopic dermatitis, lichen planus and PLEVA (pityriasis lichenoides et varioliforms acuta). In cases where the 5-(4-Phenoxybutoxy)7H-furo[3,2-g][1]benzopyran-7-on is administered topically, it may be combined with a pharmaceutically acceptable carrier to from a topical preparation such as an ointment, cream, emulsion, gel, shampoo, liquid, patch, poltus, etc. The concentration of 5-(4-Phenoxybutoxy)7H-furo[3,2-g][1]benzopyran-7-on within the topical preparation may be in the range of about 0.0001% by weight to about 1% by weight, although any suitable concentrations may be used.

It is to be appreciated that the invention has been described here above with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

APPENDIX A

Exemplary compounds and their $EC_{50}$s for $K^+$ channels

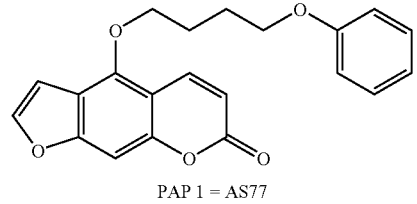

PAP 1 = AS77

| | |
|---|---|
| Kv1.1 | 65 ± 8 nM |
| Kv1.2 | 250 ± 14 nM |
| Kv1.3 | 2.0 ± 0.2 nM ($n_H$ = 1.8) |
| Kv1.4 | 75 ± 5 nM |
| Kv1.5 | 45 ± 3 nM ($n_H$ = 2.3) |
| Kv1.7 | 98 ± 5 5nM |
| HERG | 5 ± 1 μM |
| IKCa1 | 10 ± 1 μM |
| SKCa1 | 5 ± 1 μM |
| SKCa2 | 5 ± 1 μM |
| BK | 1.5 ± 0.7 μM |

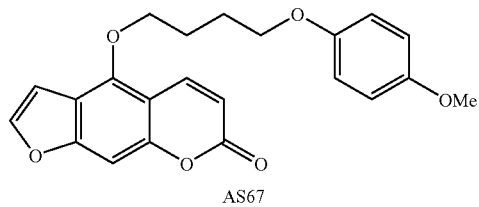

AS67

| | |
|---|---|
| Kv1.3 | 8 ± 1 nM, $n_H$ = 2.1 |
| Kv1.5 | 10 ± 1 nM |

APPENDIX A-continued
Exemplary compounds and their EC$_{50}$s for K$^+$ channels
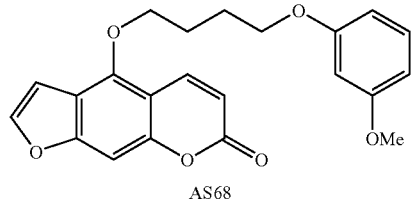
AS68
Kv1.3   21 ± 5 nM
Kv1.5   45 ± 5 nM
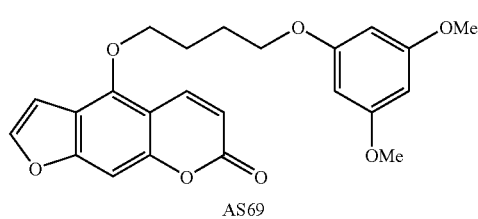
AS69
Kv1.3   120 ± 10 nM
Kv1.5   150 ± 20 nM
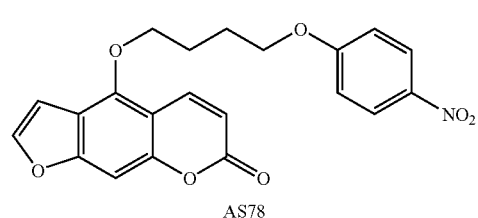
AS78
Kv1.3   7 ± 1 nM, n$_H$ = 1.9
Kv1.5   105 ± 8 nM
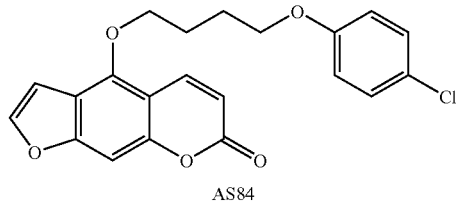
AS84
Kv1.3   5 ± 1 lnM, n$_H$ = 2.0
Kv1.5   10 nM
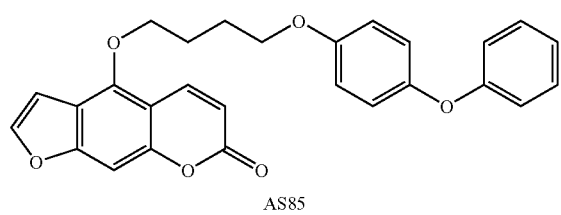
AS85
Kv1.3   16 ± 2 nM
Kv1.5   750 nM
APPENDIX A-continued
Exemplary compounds and their EC$_{50}$s for K$^+$ channels
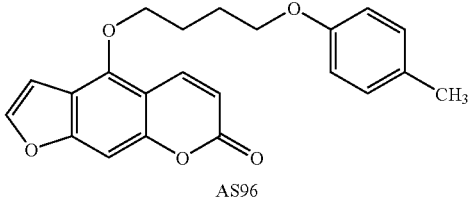
AS96
Kv1.3   7 ± 1 nM, n$_H$ = 2.1
Kv1.5   20 nM
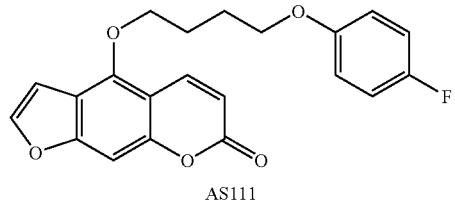
AS111
Kv1.3   12 ± 1 nM, n$_H$ = 2.3
Kv1.5   12 ± 1 nM
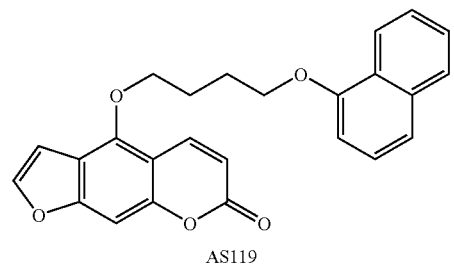
AS119
Kv1.3   20 ± 3 nM, n$_H$ = 2.0
Kv1.5   50 ± 5 nM, n$_H$ = 2.0
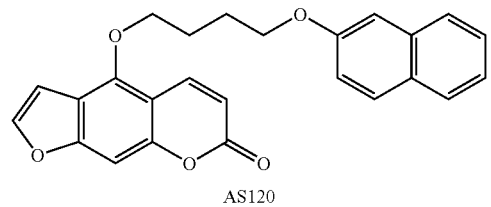
AS120
Kv1.3   12 ± 1 nM, n$_H$ = 2.1
Kv1.5   80 ± 10 nM, n$_H$ = 2.0
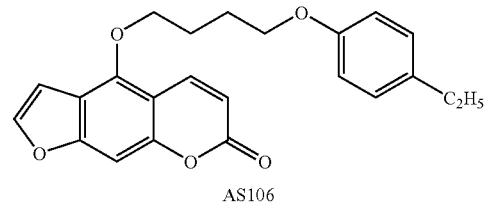
AS106
Kv1.3   13 ± 2 nM, n$_H$ = 2.0
Kv1.5   52 ± 4 nM, n$_H$ = 2.0

APPENDIX A-continued
Exemplary compounds and their EC$_{50}$s for K$^+$ channels
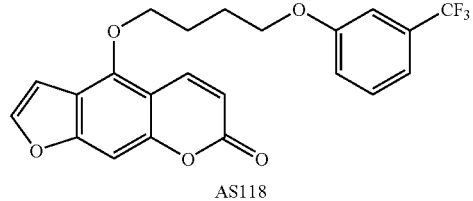
AS118
Kv1.3   65 ± 5nM, n$_H$ = 2.0
Kv1.5   250 nM
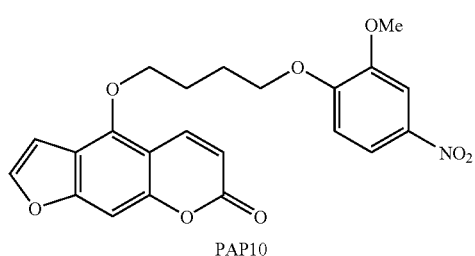
PAP10
Kv1.3   500 nM,
Kv1.5   476 ± 20 nM
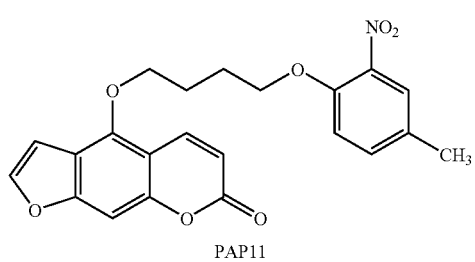
PAP11
Kv1.3   700 nM,
Kv1.5   248 ± 20 nM
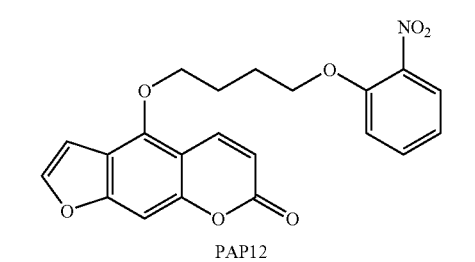
PAP12
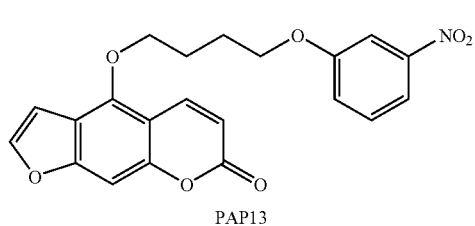
PAP13
APPENDIX A-continued
Exemplary compounds and their EC$_{50}$s for K$^+$ channels
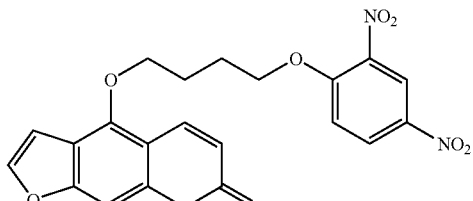
PAP14
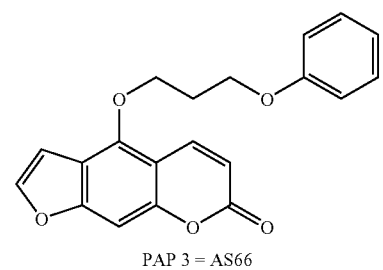
PAP 3 = AS66
Kv1.1   80 ± 10 nM
Kv1.3   15 ± 2 nM
Kv1.4   ~ 500 nM
Kv1.5   100 ± 8 nM
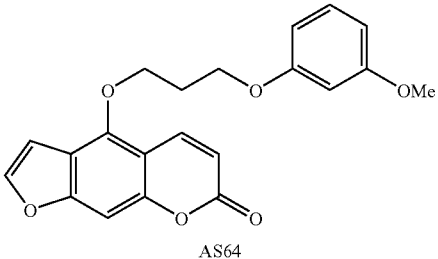
AS64
Kv1.3   45 ± 3 nM, n$_H$ = 2.0
Kv1.5
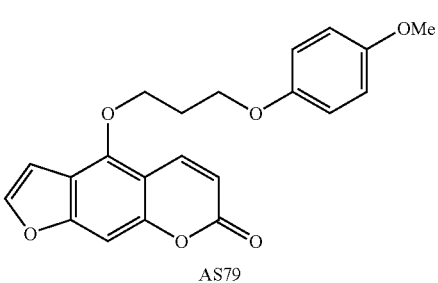
AS79
Kv1.3   42 ± 3 nM, n$_H$ = 2.05
Kv1.5

APPENDIX A-continued
Exemplary compounds and their EC$_{50}$s for K$^+$ channels
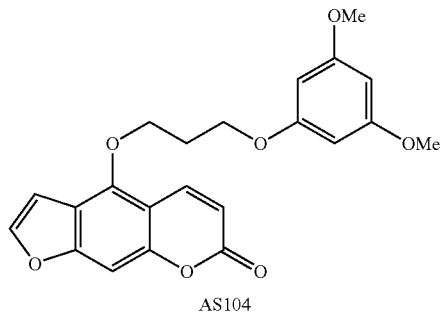
AS104
Kv1.3   75 ± 8 nM, n$_H$ = 2.2
Kv1.5
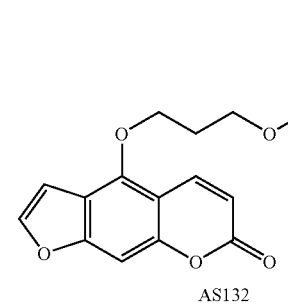
AS132
Kv1.3   10 ± 1 nM, n$_H$ = 2.1
Kv1.5
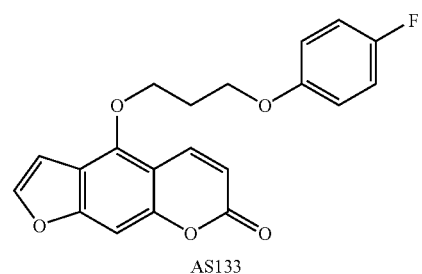
AS133
Kv1.3   20 ± 2, n$_H$ = 2.0
Kv1.5   25 ± 2, n$_H$ = 2.0
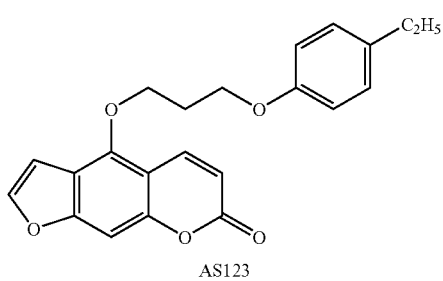
AS123
Kv1.3   14 ± 1 nM
Kv1.5   60 ± 3
APPENDIX A-continued
Exemplary compounds and their EC$_{50}$s for K$^+$ channels
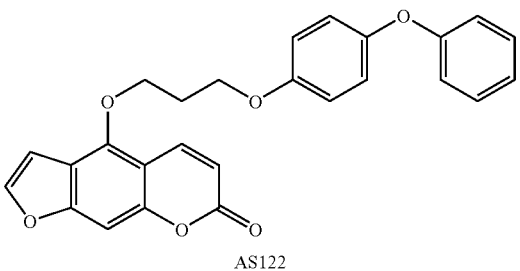
AS122
Kv1.3   25 ± 2 nM, n$_H$ = 1.9
Kv1.5   250 ± 10, n$_H$ = 1.8
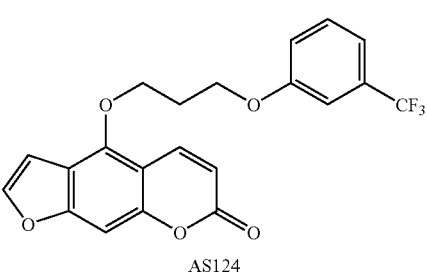
AS124
Kv1.3   30 ± 2 nM, n$_H$ = 1.7
Kv1.5   68 ± 3, n$_H$ = 2.0
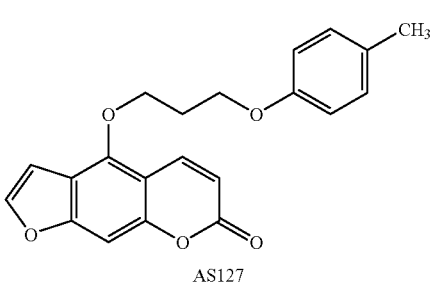
AS127
Kv1.3   24 ± 2 nM, n$_H$ = 2.2
Kv1.5   65 ± 5 nM, n$_H$ = 2.2
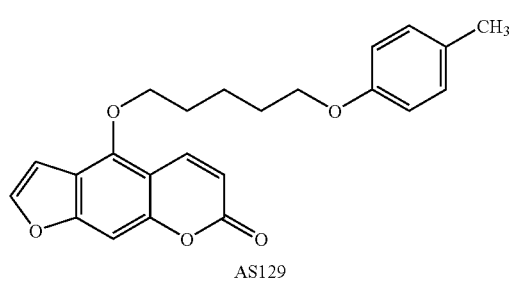
AS129
Kv1.3   20 ± 2 nM, n$_H$ = 2
Kv1.5

APPENDIX A-continued
Exemplary compounds and their EC$_{50}$s for K$^+$ channels
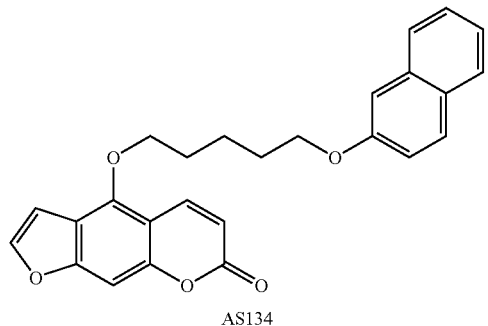
AS134
Kv1.3  18 ± 1 nM, n$_H$ = 2.1
Kv1.5
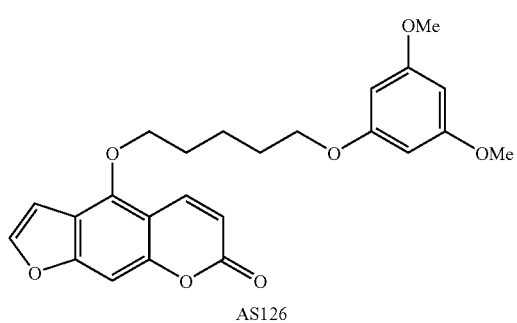
AS126
Kv1.3  32 ± 2 nM, n$_H$ = 2
Kv1.5
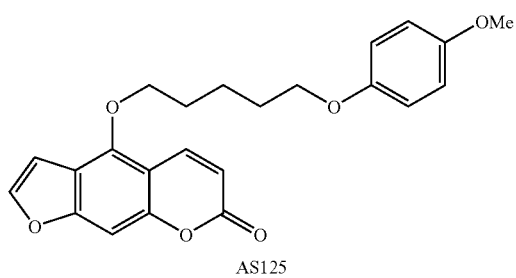
AS125
Kv1.3
Kv1.5
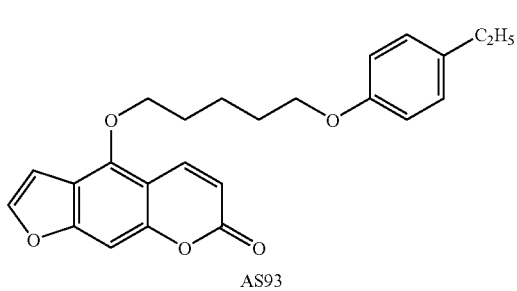
AS93
Kv1.3  35 ± 2 nM, n$_H$ = 2.1
Kv1.5
APPENDIX A-continued
Exemplary compounds and their EC$_{50}$s for K$^+$ channels
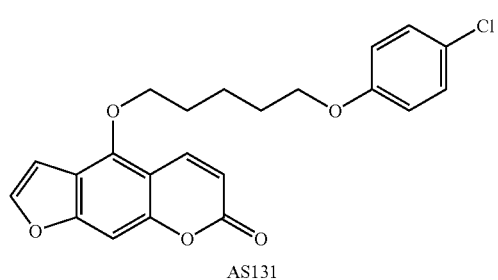
AS131
Kv1.3
Kv1.5
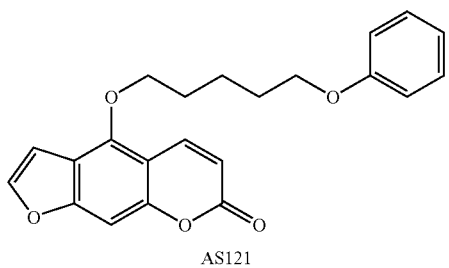
AS121
Kv1.3  15 ± 1 nM, n$_H$ = 2.1
Kv1.5
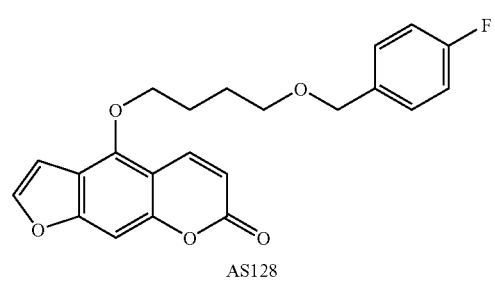
AS128
Kv1.3  16 ± 2 nM, n$_H$ = 2
Kv1.5
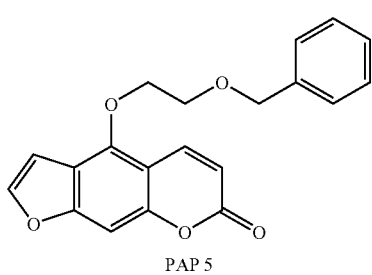
PAP 5
Kv1.1  175 ± 20 nM
Kv1.3  10 ± 1 nM
Kv1.5  110 ± 20 nM APPENDIX A-continued
Exemplary compounds and their EC$_{50}$s for K$^+$ channels
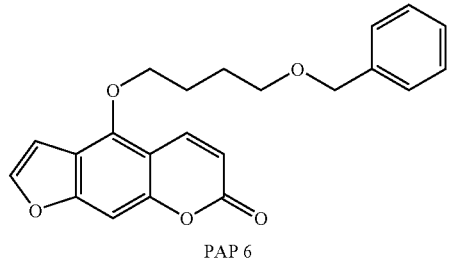
PAP 6
Kv1.3    49 ± 5 nM
Kv1.5    750 ± 40 nM
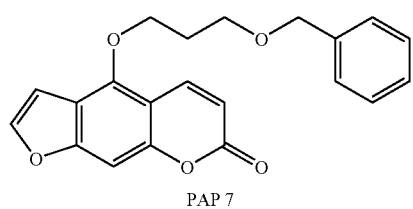
PAP 7
Kv1.3    50 ± 5 nM
Kv1.5    170 ± 20 nM
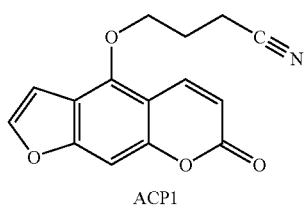
ACP1
Kv1.3    5 µM
Kv1.5    12 µM
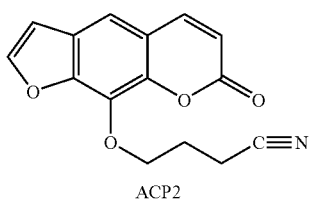
ACP2
Kv1.3    5 µM
Kv1.5    10 µM
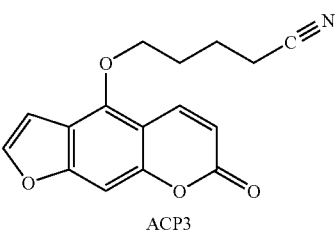
ACP3
Kv1.3    1.3 µM
Kv1.5    5 µM
APPENDIX A-continued
Exemplary compounds and their EC$_{50}$s for K$^+$ channels
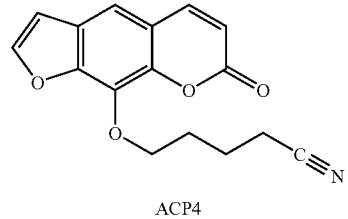
ACP4
Kv1.3    5 µM
Kv1.5    10 µM
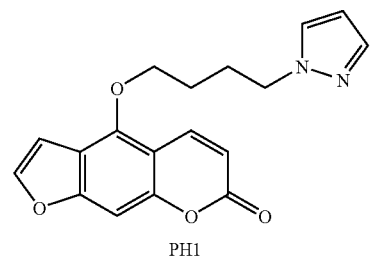
PH1
Kv1.3    450 nM
Kv1.5    5 µM
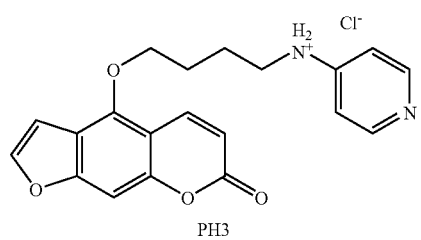
PH3
Kv1.3    5 µM
Kv1.5    5 µM
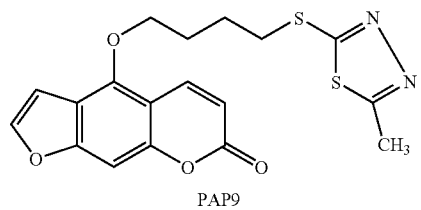
PAP9
Kv1.3
Kv1.5
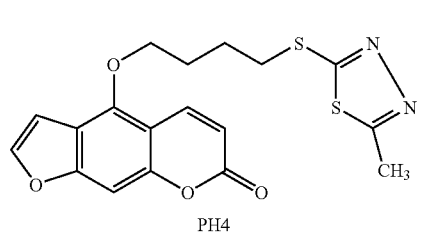
PH4
Kv1.3    175 nM
Kv1.5    1 µM

APPENDIX A-continued

Exemplary compounds and their EC$_{50}$s for K$^+$ channels

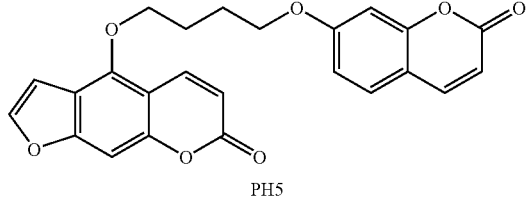

PH5

| Kv1.3 | 125 ± 20 nM |
| --- | --- |
| Kv1.5 | 5 μM |

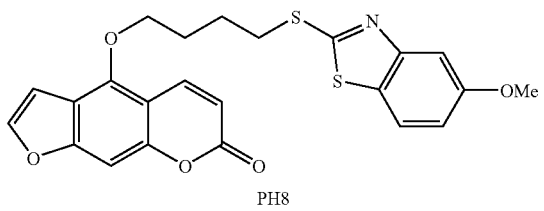

PH8

| Kv1.3 | 35 ± 5 nM |
| --- | --- |
| Kv1.5 | 100 nM |

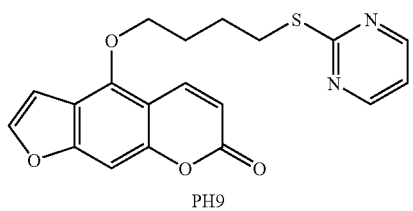

PH9

| Kv1.3 | 50 ± 5 nM |
| --- | --- |
| Kv1.5 | 159 ± 7 nM |

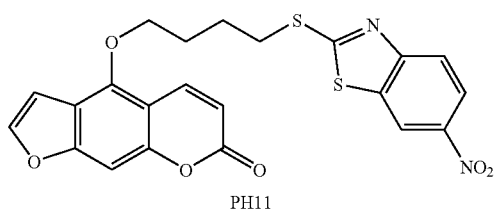

PH11

| Kv1.3 | |
| --- | --- |
| Kv1.5 | |

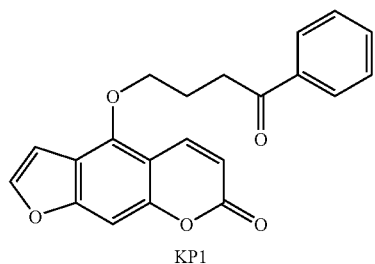

KP1

| Kv1.3 | 31 ± 1 nM |
| --- | --- |
| Kv1.5 | |

What is claimed is:

1. A composition of matter comprising a compound having the formula:

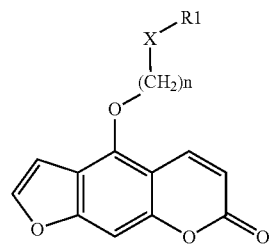

wherein:
n is 1 through 10, cyclic or acyclic and optionally substituted or unsubstituted;
X is C; and
R1 is aryl, heterocyclyl or cycloalkyl and is optionally substituted with one or more substituents selected from alkyl, alkoxy, amino and its alkyl derivatives, acylamino, carboxyl and its alkyl ester, cyano, halo, hydroxy, nitro and sulfonamido groups with the proviso that when R1 is phenyl or cycloalkyl, then it is substituted with one or more substituents selected from alkyl, alkoxy, amino and its alkyl derivatives, acylamino, carboxyl and its alkyl ester, cyano, halo, hydroxy, nitro and sulfonamido groups.

2. A method for treatment of or prophylaxis against a disease or disorder by inhibition of potassium channels, in a human or animal subject, said method comprising the step of administering to the subject, in an amount and form that is effective for treatment of or prophylaxis against the disease or disorder, a composition of matter comprising a compound having the formula:

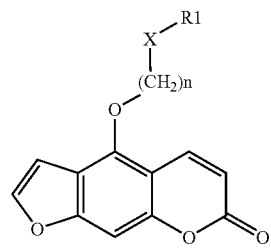

wherein:
n is 1 through 10, cyclic or acyclic and optionally substituted or unsubstituted;
X is C; and
R1 is aryl, heterocyclyl or cycloalkyl and is optionally substituted with one or more substituents selected from alkyl, alkoxy, amino and its alkyl derivatives, acylamino, carboxyl and its alkyl ester, cyano, halo, hydroxy, nitro and sulfonamido groups with the proviso that when R1 is phenyl or cycloalkyl, then it is substituted with one or more substituents selected from alkyl, alkoxy, amino and its alkyl derivatives, acylamino, carboxyl and its alkyl ester, cyano, halo, hydroxy, nitro and sulfonamido groups.

3. A method according to claim 2 wherein the disease or disorder is a T cell mediated autoimmune disease or disorder.

4. A method according to claim 3 wherein the compound inhibits Kv1.3 channels.

5. A method according to claim 4 wherein the compound has a substantially greater affinity for inhibition of Kv1.3 than for inhibition of Kv1.5 channels.

6. A method according to claim 4 wherein the subject does not suffer from atrial fibrillation and wherein the compound inhibits Kv1.3 channels sufficiently to treat or prevent the disease or disorder but does not inhibit Kv1.5 channels sufficiently to cause cardiac arrhythmias.

7. A method according to claim 4 wherein the compound has an affinity for inhibition of Kv1.3 channels that is at least 10 times greater than its affinity for inhibition of Kv1.5 channels.

8. A method according to claim 4 wherein the compound is administered orally.

9. A method according to claim 4 wherein the compound is administered parenterally.

10. A method according to claim 4 wherein the compound is administered topically.

* * * * *